United States Patent [19]
Fisher et al.

[11] Patent Number: 5,851,764
[45] Date of Patent: Dec. 22, 1998

[54] HUMAN PROSTATE TUMOR INDUCING GENE-1 AND USES THEREOF

[75] Inventors: Paul B. Fisher, Scarsdale; Ruoqian Shen, New York, both of N.Y.

[73] Assignee: The Trustees of Columbia University in the City of New York, New York, N.Y.

[21] Appl. No.: 371,377

[22] Filed: Jan. 11, 1995

Related U.S. Application Data

[63] Continuation-in-part of Ser. No. 351,888, Dec. 8, 1994, which is a continuation of Ser. No. 225,493, Apr. 11, 1994, abandoned, which is a continuation of Ser. No. 106,323, Aug. 13, 1993, abandoned, which is a continuation of Ser. No. 603,804, Oct. 25, 1990, abandoned.

[51] Int. Cl.$^6$ ............. C12Q 1/68; C07H 21/04; G01N 33/00; C12N 15/00
[52] U.S. Cl. ............. 324/6; 435/91.1; 436/94; 536/23.5; 536/24.1; 536/24.33; 536/24.31; 536/25.3; 935/8; 935/76; 935/77
[58] Field of Search ............. 435/6, 91.1, 91.2, 435/183, 270; 436/94; 536/23.5, 24.1, 24.33, 24.31, 25.3; 935/76, 77, 78

[56] References Cited

U.S. PATENT DOCUMENTS

| | | | |
|---|---|---|---|
| 4,631,259 | 12/1986 | Clewell et al. | 435/172.3 |
| 4,634,665 | 1/1987 | Axel et al. | 435/68 |
| 4,681,840 | 7/1987 | Stephenson et al. | 435/6 |
| 4,699,877 | 10/1987 | Cline et al. | 435/6 |
| 4,786,718 | 11/1988 | Weinberg et al. | 530/387 |
| 4,871,838 | 10/1989 | Bos et al. | 536/27 |
| 4,892,935 | 1/1990 | Yoshida et al. | 530/387 |
| 4,914,021 | 4/1990 | Toth et al. | 435/7 |
| 4,935,341 | 6/1990 | Bargmann et al. | 435/6 |
| 4,994,558 | 2/1991 | Armour et al. | 530/391 |
| 4,996,298 | 2/1991 | Salem et al. | 530/395 |
| 5,028,420 | 7/1991 | Masegi et al. | 424/85.1 |

FOREIGN PATENT DOCUMENTS 0346702  12/1989  European Pat. Off. .

OTHER PUBLICATIONS

Drebin, J.A., et al. (1984) Monoclonal Antibodies Identify a Cell–Surface Antigen Associated with an Activated Cellular Oncogene, Nature 312:545–548.

Hollingsworth, M.A., et al., (1986) Antigens Expressed on NIH 3T3 Cells Following Transformation with DNA from a Human Pancreatic Tumor, Cancer Res. 46:2482–2487.

Liaw, W.–S., et al., (1987) Transfer of a Malignant Phenotype by Calcium–mediated DNA Transfection from Human Prostatic Carcinoma Cells to a Cloned Rat Embryo Fibroblast.

(CREF) Cell Line, J. Virol., 137:113A, Abstract 38.

Su, Z.–Z., et al., (1992) Transfer of a Dominant–Acting Tumor–Inducing Oncogene from Human Prostatic Carcinoma Cells to Cloned Rat Embryo Fibroblast Cells by DNA–Transfection, Anticancer Res. 12(2):297–304.

*Primary Examiner*—Bradley L. Sisson
*Attorney, Agent, or Firm*—John P. White; Cooper & Dunham LLP

[57] ABSTRACT

This invention provides a method for preparing a hybridoma cell line which produces an antibody capable of specifically binding to a cell surface-expressed protein which expresses on the surface of one cell type but not the other. This invention also provides a method for preparing a hybridoma cell line which produces an antibody capable of specifically binding to a cell surface-expressed protein. This invention provides a method to prepare a hybridoma cell line which specifically recognizes and binds to a tumor associated antigen associated with a neoplastic, human cell. This invention also provides a method of preparing DNA encoding a cell surface antigen associated with a neoplastic, human cell. This invention further provides an isolated mammalian nucleic acid molecule having the sequence of Prostate Carcinoma Tumor Antigen Gene-1. This invention also provides an isolated mammalian nucleic acid molecules having the sequence of Prostate Tumor Inducing Gene-1. This invention provides an isolated mammalian nucleic acid molecules having the sequence of Prostate Tumor Inducing Gene-2. Finally, this invention provides an isolated mammalian nucleic acid molecules having the sequence of Prostate Tumor Inducing Gene-1.

8 Claims, 23 Drawing Sheets

FIGURE 8A

```
1     gtatacgaaatcataaaatctcatagatgtatcctgagtagggcgggcccgtgaaaccctctgaatctgcggccaccaccggtaaggc         90
91    taaatactaatcagacaccggatagtgaactagtgaactacctgtgaggaaaaggtgaaaagaacccgagagaggagtgaaatagattctgaaacc     179
180   attactacaagtggtccattactacaagtgtcagagagcacgttaaagtgatggctgtacatcttgcagtatgggccggcgagttatgt         271
272   taatatgcaaggtctatccatgagcaggttgaagcttagtaaaactaagtggaggaccgagtcgatagggctaaccgtagtattgggg     361
362   caggtgatctatccatgagcaggttgaagcttagtaaaactaagtggaggaccgaaccgtagtattgggctaaaaagtgccggatggactt     451
452   gtggatagtgtgaaattccaatggaatatagcttaaaatagcctggaaatagcttaggggctgtctcttcgaaatagcttaggggctagtcgtagtagtgttaagggggg     543
544   tagagcactgaatggaatggccgcatctagctgtactgactataatcaaactcgaatacattaaaataagctATG CAG TCG             629
                                                                           M   Q   S 630   GAA CGT GGT ATC ACC ATT GAT ATC TCC TTG TGG AAA TTT GAG ACC AGC AAG TAC TAT           686
      E   R   G   I   T   I   D   I   S   L   W   K   F   E   T   S   K   Y   Y 687   GTG ACT ATC ATT GAT GCC CCA GGA CAC AGA GAC TTT ATC CAA AAC ATG ATT ACA GG           742
      V   T   I   I   D   A   P   G   H   R   D   F   I   Q   N   M   I   T   G 743   G ACC TCT CAG GCT GAC TGT GCT GTC CTG ATT GTT GCT GCT GGT GTT GGT GAA TTT GAA G      801
      G   T   S   Q   A   D   C   A   V   L   I   V   A   A   G   V   G   E   F   E 802   CT GGT ATC TCC AAG AAT GGG CAG ACC CGA GAA CAG CAG CCT CTG TAC ACA CTG GG            858
      A   G   I   S   K   N   G   Q   T   R   E   H   A   L   L   A   Y   T   L   G 859   T GTG AAA CAA CTA ATT GTC GGT GTT AAC AAA ATG GAT TCC ACT GAG CCA CCC TAC            914
      V   K   Q   L   I   V   G   V   N   K   M   D   S   T   E   P   P   Y 915   AGC CAG AAG AGA TAT GAG GAA ATT GTT AAG GAA GTC AGC ACT TAC ATT AAG AAA              968
      S   Q   K   R   Y   E   E   I   V   K   E   V   S   T   Y   I   K   K 969   ATT GGC TAC AAC CCC GAC ACA GTA GCA TTT GTG CCA ATT TCT GGT TGG AAT GGT GAC         1025
      I   G   Y   N   P   D   T   V   A   F   V   P   I   S   G   W   N   G   D 1026  AAC ATG CTG GAG CTG GCC AGT AAC ATG GCT GCT CCT TGG TTC AAG GGA TGG AAA GTC ACC CGT 1082
      N   M   L   E   P   S   A   N   M   A   A   P   W   F   K   G   W   K   V   T   R 1083  AAG GAT GGC AAT GCC AGT GGA ACC ACG CTG CTT GAG GCT CTG GAC TGC ATC CTA CCA        1139
      K   D   G   N   A   S   G   T   T   L   L   E   A   L   D   C   I   L   P 1140  CCA ACT CGT CCA ACT GAC AAG CCC TTG GGC CTG CCT CTC CAG GAT GTC TAC AAA ATT         1196
      P   T   R   P   T   D   K   P   L   G   L   P   L   Q   D   V   Y   K   I
```

FIGURE 8B

```
1197 GGT GGT ATT GGT ACT GTT CCT GTT GGC CGA GTG GAG ACT GGT GTT CTC AAA CCC GGT 1253
      G   G   I   G   T   V   P   V   G   R   V   E   T   G   V   L   K   P   G
1254 ATG GTG GTC ACC TTT GGT CCA GTC AAC GTT ACA ACG GAA GTA AAA TCT GTC GAA ATG 1310
      M   V   V   T   F   G   P   V   N   V   T   T   E   V   K   S   V   E   M
1311 CAC CAT GAA GCT TTG GGT GAA GCT CTT CCT GGG GAC AAT GTG GGC TTC AAT GTC AAG 1367
      H   H   E   A   L   G   E   A   L   P   G   D   N   V   G   F   N   V   K
1368 AAT GTG TCT GTC AAG GAT GTT CGT GGC AAC GTT GCT GGT GAC AGC AAA AAT GAC 1424
      N   V   S   V   K   D   V   R   G   N   V   A   G   D   S   K   N   D
1425 CCA CCA ATG GAA GCA GCT GGC TTC CCT GCT CAG GTG ATT ATC CTG AAC CAT CCA GGC 1481
      P   P   M   E   A   A   G   F   P   A   Q   V   I   I   L   N   H   P   G
1482 CAA ATA AGC GCC GGC TAT GCC CCT GTA TTG GAT TGC CAC ACG GCT CAC ATT GCA TGC 1538
      Q   I   S   A   G   Y   A   P   V   L   D   C   H   T   A   H   I   A   C
1539 AAG TTT GCT GAG CTG AAG GAA AAG ATT GAT CGC CGT TCT GGT AAA AAG CTG GAA 1592
      K   F   A   E   L   K   E   K   I   D   R   R   S   G   K   K   L   E
1593 GAT GGC CCT AAA TTC TTG AAG TCT GGT GAT GCT GCC ATT GTT GAT ATG GTT CCT GGC 1649
      D   G   P   K   F   L   K   S   G   D   A   A   I   V   D   M   V   P   G
1650 AAG CCC ATG TGT GTT GAG AGC TTC TCA GAC TAT CCA CCT TTG GGC TGC TTT GCT GTT 1706
      K   P   M   C   V   E   S   F   S   D   Y   P   P   L   G   F   A   V
1707 CGT GAT ATG AGA CAG ACA GTT GCG GTG GGT GTC ATC AAA GCA GTG GAC AAG AAG GCT 1763
      R   D   M   R   Q   T   V   A   V   G   V   I   K   A   V   D   K   K   A
1764 GCT GGA GCT GGC AAG GTC ACC AAG TCT GCC CAG AAA GCT CAG AAG GCT AAA TGA 1817
      A   G   A   G   K   V   T   K   S   A   Q   K   A   Q   K   A   K   ter
1818 atattatccctaatcagtcatcctccccaccctctaatcagtggttggaagaccggtcttcaattggccattaagttttagt 1904
1910 agtaaaagactgtttttaagttgttaatgataacaatgcatcgtaaaacctttcagaaggagaaatgttttgtggaccacgttgttgtttttttgc 1996
1997 gtgtggcagttttaagttattagttttttaaaatcagtactttttaatgaaacaactgacccccaaattgtcacagaattttgggaccat 2089
2090 taaaaaggtaactgggaaaaaaaaaaaaaaaaaa                                                    2123
```

FIGURE 8C

```
(E)1         MGKEKTHINIVVIGH                                                    15

(E)16    YDSGKSTTTGHLIVKCGGIDKRTIEKFEKEAAEMGKGSFKYAWVLDKLKAER                    67
(P)1                                                  MQS                        3
                                     *
(E)68    ERGITDISLWKFETSKYYVTIIDAPGHRDFIKNMITGTSQADCAVLIVAAGV                   120
(P)4     ERGITDISLWKFETSKYYVTIIDAPGHRDFIQNMITGTSQADCAVLIVAAGV                    56

(E)121   GEFEAGISKNGQTREHALLAYTLGVKQLIVGVNKMDSTEPPYSQKRYEEIVKE                  173
(P)57    GEFEAGISKNGQTREHALLAYTLGVKQLIVGVNKMDSTEPPYSQKRYEEIVKE                  109

(E)174   VSTYIKKIGYNPDTVAFVPISGWNGDNMLEPSANMPWFKGWKVTRKDGNA                     223
(P)110   VSTYIKKIGYNPDTVAFVPISGWNGDNMLEPSANMPWFKGWKVTRKDGNA                     159
                                          *
(E)224   SGTTLLEALDCILPPTRPTDKPLRLPLQDVYKIGGIGTVPVGRVETGVLKPGM                  276
(P)160   SGTTLLEALDCILPPTRPTDKPLGLPLQDVYKIGGIGTVPVGRVETGVLKPGM                  212
                                    *
(E)277   VVTFAPVNVTEVKSVEMHHEALSEALPGDNVGFNVKNVSVKDVRRGNV                       325
(P)213   VVTFGPVNVTEVKSVEMHHEALGEALPGDNVGFNVKNVSVKDVRRGNV                       261

(E)326   AGDSKNDPPMEAAGFTAQVIILNHPGQISAGYAPVLDCHTAHIACKFAELK                    376
(P)262   AGDSKNDPPMEAAGFPAQVIILNHPGQISAGYAPVLDCHTAHIACKFAELK                    312
                                                    *
(E)377   EKIDRRSGKKLEDGPKFLKSGDAAIVDMVPGKPMCVESFSDYPPLGRFAVRD                   428
(P)313   EKIDRRSGKKLEDGPKFLKSGDAAIVDMVPGKPMCVESFSDYPPLGCFAVRD                   364

(E)429   MRQTVAVGVIKAVDKKAAGAGKVTKSAQKAQKAK                                     462
(P)365   MRQTVAVGVIKAVDKKAAGAGKVTKSAQKAQKAK                                     398
```

FIGURE 8D

| Human EF-1α | Amino Acid | K (100) | R (247) | A (281) | S (300) | T (341) | R (423) |
|---|---|---|---|---|---|---|---|
| | Codon | AAA | CGC | GCT | AGT | ACT | CGC |
| | Nucleotide | A | C | C | A | A | C |

| PTI-1 | Amino Acid | Q (36) | G (183) | G (217) | G (236) | P (277) | C (359) |
|---|---|---|---|---|---|---|---|
| | Codon | CAA | GGC | GGT | GGT | CCT | TGC |
| | Nucleotide | C | G | G | G | C | T |

FIGURE 13A

```
  1 CGGACCGAGC TCCGTTGCAT TTTGATGAAT CCATAGTCAA ATTAGCGAGA
 51 CACGTTGCGA ATTGAAACAT CTTAGTAGCA ACAGGAAAAG AAAATAAATA
101 ATGATTTCGT CAGTAGTGGC GAGCGAAAGC GAAAGAGCCC AAACCTGTAA
151 AGGGGGGTTG GTAGGACATC TTACATTGAG TTACAAAATT TTATGATAGT
201 AGAAGAAGTT GGGAAAGCTT CAACATAGAA GGTGATATTC CTGTATACGA
251 AATCATAAAA TCTCATAGAT GTATCCTGAG TAGGGCGGGG TACGTGAAAC
301 CCTGTCTGAA TCTGCCCGGG ACCACCCGTA AGGCTAAATA CTAATCAGAC
351 ACCGATAGTG AACTAGTACC GTGAGGGAAA GGTGAAAAGA ACCCGAGAGG
401 GGAGTGAAAT AGATTCTGAA ACCATTTACT TACAAGTAGT CAGAGCACGT
451 TAAAGTGTGA TGGCGTACAT CTTGCAGTAT GGGCCGGCGA GTTATGTTAA
501 TATGCAAGGT TAAGCACGAA AAAGCGGAG CCGTAGGGAA ACCGAGTCTG
551 AATAGGGCGA CTTTAGTATA TTGGCATATA CCCGAAACCA GGTGATCATC
601 CATGAGCAGG TTGAAGCTTA GGTAAAACTA AGTGGAGGAC CGAACCGTAG
651 TACGCTAAAA AGTGCCCGGA TGACTTGTGG ATAGTGGTGA AATTCCAATC
701 GAACCTGGAG ATAGCTGGTT CTCTTCGAAA TAGCTTTAGG GCTAGCGTAT
751 AGTACTGTTT AATGGGGGTA GAGCACTGAA TGTGGAATGG CGGCATCTAG
801 CTGTACTGAC TATAATCAAA CTCCGAATAC CATTAAAATT AAGCTATGCA
851 GTCGGAACGT GGGTGATAAC GTCCACGCTC GCGAGGGAAA CAACCCAGAT
901 CCGTCAGCTA AGGTCCCAAA ATTGTGTTAA GTGAGAAAGG TTGTGGAGAT
951 TTCATAAACA ACTAGGAAGT TGGTTTAGAA GCAGCCACCT TTTAAAGAGT
1001 GCGTAATTGC TCACTAGTCA AGAGATCTTG CGCCAATAAT GTAACGGGAC
1051 TCAAACACAA TACCCAAGCT ACGGGCACAT TATGTGCGTT AGGAGAGCGT
1101 TTTAATTTCG TTGAAGTCAG ACCGTGAGAC TGGTGGAGAG ATTAAAAGTT
1151 CGAGAATGCC GGCATGAGTA ACGATTCGAA GTGAGAATCT TCGACGCCTA
1201 TTGGGAAAGG TTTCCTGGGC AAGGTTCTCC ACCCAGGGTT AGTCAGGGCC
1251 TAAGATGAGG CAGAAATGCA TAGTCGATGG ACAACAGGTT AATATTCCTG
```

FIGURE 13B

```
1301 TACTTGGTAA AAGAATGATG GAGTGACGAA AAAGGATAGT TCTACCACTT
1351 CCACTATGTC CTATCAATAG GAGCTGTATT TGGCATCATA GGAGGCTTCA
1401 TTCACTGATT TCCCCTATTC TCAGGCTACA CCCTAGACCA AACCTACGCC
1451 AAAATCCATT TCACTATCAT ATTCATCGGC GTAAATCTAA CTTTCTTCCC
1501 ACAACACTTT CTCGGCCTAT CCGGAATGAC CCGACCCGAC GTTACTCGGA
1551 CTACCCCGAT GCATACACCA CATGAAACAT CCTATCATCT GTAGGCTCAT
1601 TCATTTCTCT AACAGCAGTA ATATTAATAA TTTTCATGAT TTGAGAAGCC
1651 TTCGCCTTCG AAGCGAAAAG TCCTAATAGT AGAAGAACCC TCCATAAACC
1701 TGGAGTGACT ATATGGATGC CCCCACCCTA CCTCACATTC GAAGAACCCG
1751 TATACATAAA ATCTAGACAA AAAAGGAAGG AAGTGAACGC CCCACAAAAA
1801 AAAAAAAAAA AAAAAAAAA
```

FIGURE 14A

```
   1 AACTAAGTGG AGGACCGAAC CGTAGTACGC TAAAAAGTGC CCGGATGACT
  51 TGTGGATAGT GGTGAAATTC CAATCGAACC TGGAGATAGC TGGTTCTCTT
 101 CGAAATAGCT TTAGGGCTAG CGTATAGTAT TGTTTAATGG GGGTAGAGCA
 151 CTGAATGTGG AATCGGCGGC ATCTAGCTGT ACTGACTATA ATCAAACTCC
 201 GAATACCATT AAAATTAAGC TATGCAGTCG AACGTGGGT GATAACCTCC
 251 ACTCTCGCGA GGGAAACAAC CCAGATCGTC AGCTAAGGTC CCAAAATTGT
 301 GTTAAGTGAG AAAGGTTGTG AGATTTCATA ACAACTAGG AAGTTGGCTT
 351 AGAAGCAGCC ACCTTTTAAA GAGTGCGTAA TTGCTCACTA GTCAAGAGAT
 401 CTTGCGCCAA TAATGTAACG GGACTCAAAC ACAATACCGA AGCTACGGGC
 451 ACATTATGTC GGTTAGGAGA GCGTTTTAAT TTCGTTGAAG TCAGACCGTG
 501 AGACTGGTGG AGAGATTAAA AGTTCGAGAA TGCCCGGCAT GAGTAACGAT
 551 TCGAAGTGAG AATCTTCGAC GCCTATTGGG AAAGGTTTCC TGGGCAAGGT
 601 TCGTCCACCC AGGGTTAGTC AGGGCCTAAG ATGAGGCAGA AATGCATAGT
 651 CGATGGACAA CAGGTTAATA TTCCTGTACT TGGTAAAAGA ATGATGGAGT
 701 GACGAAAAAG GATAGTTCTA CCACTTACTG GATTGTGGGG TAAGCAACAA
 751 GAGAGTTATA TAGGCAAATC CGTATAGCAT AATCTTGAGT TGTGATGCAT
 801 AGTGAAGACT TCGGTCGAGT AACGAATTGA ATCGATTTCA TGTTTCCAAG
 851 AAAAGCTTCT AGTGTTAATT TTTTATCAAC CTGTACCGAG AACGAACACA
 901 CGTTCCCAAG ATGAGTATTC TAAGGCGAGC GAGAAAACCA ATGTTAAGGA
 951 ACTCTGCAAA ATAACCCCGT AAGTTCGCGA GAAGGGGCGC CTATTTTTAA
1001 TAGGCCACAG AAAATAGGGG GGCAACTGTT TATCAAAAAC ACAGCTCTCT
1051 GCTAAGTTGT AAAACGACGT ATAGAGGGTG AAGCCTGCCC AGTCCCGAAG
1101 TTAAACGGAG ATGTTAGCTT ACGCAAAGCA TTAAAGTGAA GCCCGGGTGA
1151 ACGGCGGCCG TAACTATAAC GGTCCTAAGG TAGCGAAATT CCTTGTCAAC
1201 TAATTATTGA CCTGCACGAA AGGCGCAATG ATCTCCCTAC TGTCTCAACA
1251 TTGGACTCGG TGAAATTATG GTACCAGTGA AAACGCAGGT TACCCGCATC
```

FIGURE 14B

1301 AAGACGAAAA GACCCCGTGG AGCTTTACTA TAACTTCGTA TTGAAAATTG

1351 GTTTAGCATG TGTAGGATAG GCGGGAGACT TTGAAGCTGG GACGCTAGTT

1401 CTAGTGGAGT CAACCTTGAA ATACCACCCT TGCTAAATTG ATTTTCTAAC

1451 CCGTTCCCCT TATCTGGAAG GAGACAGTGC GTGGTGGGTA GTTTGACTGG

1501 GCGGTCGCCT CCTAAAGTGT AACGGAGGCG TTCAAAGCTA CACTCAATAT

1551 GGTCAGAAAC CATATGCAGA GCACAAAGGT AAAAGTGTGG TTGACTGCAA

1601 GACTTACAAG TCGAGCAGGT GCGAAAGCAG GACTTAGTGA TCCGGCGGTA

1651 CATTGTGGAA TGGCCGTCGC TCAACGGATA AAAGTCACCC CGGGGATAAC

1701 AGGCTAATCT TCCCCAAGAG ATCACATCGA CGGGAAGGTT TGGCACCTCG

1751 ATGTCGGCTC ATCGCATCCT GGAGCTGGAG TCGGTTCCAA GGGTTTGCTG

1801 TTCGCCAATT AAAGCGGTAC GTGAGCTGGG TTCAGAACGT CGTGAGACAG

1851 TTCGGTCCTC CACTTAGTT

FIGURE 15A

- 1 CGGCACGAGC GGCACGAGAG AAGAGACTCC AATCGACAAG AAGCTGGAAA

- 51 AGAATGATGT TGTCCTTAAA CAACCTACAG AATATCATCT ATAACCCGGT

- 101 AATCCCGTTT GTTGGCACCA TTCCTGATCA GCTGGATCCT GGAACTTTGA

- 151 TTGTGATACG TGGGCATGTT CCTAGTGACG CAGACAGATT CCAGGTGGAT

- 201 CTGCAGAATG GCAGCAGCGT GAAACCTCGA GCCGATGTGG CCTTTCATTT

- 251 CAATCCTCGT TTCAAAAGGG CCGGCTGCAT TGTTTGCAAT ACTTTGATAA

- 301 ATGAAAAATG GGGACGGGAA GAGATCACCT ATGACACGCC TTTCAAAAGA

- 351 GAAAAGTCTT TTGAGATCGT GATTATGGTG CTGAAGGACA AATTCCAGGT

- 401 GGCTGTAAAT GGAAAACATA CTCTGCTCTA TGGCCACAGG ATCGGCCCAG

- 451 AGAAAATAGA CACTCTGGGC ATTTATGGCA AAGTGAATAT TCACTCAATT

- 501 GGTTTTAGCT TCAGCTCGGA CTTACAAAGT ACCCAAGCAT CTAGTCTGGA

- 551 ACTGACAGAG ATAGTTAGAG AAAATGTTCC AAAGTCTGGC ACGCCCCAGC

- 601 TTAGCCTGCC ATTCGCTGCA AGGTTGAACA CCCCCATGGG CCCTGGACGA

- 651 ACTGTCGTCG TTCAAGGAGA AGTGAATGCA AATGCCAAAA GCTTTAATGT

- 701 TGACCTACTA GCAGGAAAAT CAAAGGATAT TGCTCTACAC TTGAACCCAC

- 751 GCCTGAATAT TAAAGCATTT GTAAGAAATT CTTTTCTTCA GGAGTCCTGG

- 801 GGAGAAGAAG AGAGAAATAT TACCTCTTTC CCATTTAGTC CTGGGATGTA

FIGURE 15B

- 851 CTTTGAGATG ATAATTTATT GTGATGTTAG AGAATTCAAG GTTGCAGTAA

- 901 ATGGCGTACA CAGCCTGGAG TACAAACACA GATTTAAAGA GCTCAGCAGT

- 951 ATTGACACGC TGGAAATTAA TGGAGACATC CACTTACTGG AAGTAAGGAG

- 1001 CTGGTAGCCT ACCTACACAG CTGCTACAAA AACCAAAATA CAGAATGGCT

- 1051 TCTGTGATAC TGGCCTTGCT GAAACGCATC TCACTGGTCA TTCTATTGTT

- 1101 TATATTGTTA AAATGAGCTT GTGCACCATT AGGTCCTGCT GGGTGTTCTC

- 1151 AGTCCTTGCC ATGACGTATG GTGGTGTCTA GCACTGAATG GGGAAACTGG

- 1201 GGGCAGCAAC ACTTATAGCC AGTTAAAGCC ACTCTGCCCT CTCTCCTACT

- 1251 TTGGCTGACT CTTCAAGAAT GCCATTCAAC AAGTATTTAT GGAGTACCTA

- 1301 CTATAATACA GTAGCTAACA TGTATTGAGC ACAGATTTTT TTTGGTAAAT

- 1351 CTGTGAGGAG CTAGGATATA TACTTGGTGA AACAAACCAG TATGTTCCCT

- 1401 GTTCTCTTGA GCTTCGACTC TTCTGTGCGC TACTGCTGCG CACTGCTTTT

- 1451 TCTACAGGCA TTACATCAAC TCCTAAGGGG TCCTCTGGGA TTAGTTATGC

- 1501 AGATATTAAA TCACCCGAAG ACACTAACTT ACAGAAGACA CAACTCCTTC

- 1551 CCCAGTGATC ACTGTCATAA CCAGTGCTCT GCCGTATCCC ATCACTGAGG

- 1601 ACTGATGTTG ACTGACATCA TTTTCTTTAT CGTAATAAAC ATGTGGCTCT

- 1651 ATTAGCTGCA AGCTTTACCA AGTAATTGGC ATGACATCTG AGCACAGAAA

- 1701 TTAAGCCAAA AAACCAAAGC AAAACAAATA CATGGTGCTG AAATTAACTT

FIGURE 15C

- 1751 GATGCCAAGC CCAAGGCAGC TGATTTCTGT GTATTTGAAC TTACCCGAAA
- 1801 TCAGAGTCTA CACAGACGCC TACAGAAGTT TCAGGAAGAG CCAAGATGCA
- 1851 TTCAATTTGT AAGATATTTA TGGCCAACAA AGTAAGGTCA GGATTAGACT
- 1901 TCAGGCATTC ATAAGGCAGG CACTATCAGA AAGTGTACGC CAACTAAGGG
- 1951 ACCCACAAAG CAGGCAGAGG TAATGCAGAA ATCTGTTTTG TTCCCATGAA
- 2001 ATCACCAATC AAGGCCTCCG TTCTTCTAAA GATTAGTCCA TCATCATTAG
- 2051 CAACTGAGAT CAAAGCACTC TTCCACTTTA CGTGATTAAA ATCAAACCTG
- 2101 TATCAGCAAG TTAAATGGTT CCATTTCTGT GATTTTTCTA TTATTTGAGG
- 2151 GGAGTTGGCA GAAGTTCCAT GTATATGGGA TCTTTACAGG TCAGATCTTG
- 2201 TTACAGGAAA TTTCAAAGGT TTGGGAGTGG GGAGGGAAAA AAGCTCAGTC
- 2251 AGTGAGGATC ATTCCACATT AGACTGGGGC AGAACTCTGC CAGGATTTAG
- 2301 GAATATTTTC AGAACAGATT TTAGATATTA TTTCTATCCA TATATTGAAA
- 2351 AGGAATACCA TTGTCAATCT TATTTTTTTA AAAGTACTCA GTGTAGAAAT
- 2401 CGCTAGCCCT TAATTCTTTT CCAGCTTTTC ATATTAATGT ATGCAGAGTC
- 2451 TCACCAAGCT CAAAGACACT GGTTGGGGGT GGAGGGTGCC ACAGGGAAAG
- 2501 CTGTAGAAGG CAAGAAGACT CGAGAATCCC CCAGAGTTAT CTTTCTCCAT
- 2551 AAAGACCATC AGAGTGCTTA ACTGAGCTGT TGGAGACTGT GAGGCATTTA
- 2601 GGAAAAAAAT AGCCCACTCA CATCATTCCT TGTAAGTCTT AAGTTCATTT

FIGURE 15D

- 2651 TCATTTTACG TGGAGGAAAA AAATTTAAAA AGCTATTAGT ATTTATTAAT

- 2701 GAATTTTACT GAGACATTTC TTAGAAATAT GCACTTCTAT ACTAGCAAGC

- 2751 TCTGTCTCTA AAATGCAAGT TGGCCTTTTG CTTGCCACAT TTCTGCATTA

- 2801 AACTTCTATA TTAGCTTCAA AGGCTTTTAA TCTCAATGCG AACATTCTAC

- 2851 GGGATGTTCT TAGATGCCTT TAAAAAGGGG GCAAGATCTA ATTTTATTTG

- 2901 AACCCTCACT TTCCAACTTT CACCATGACC CAGTACTAGA GATTAGGGCA

- 2951 CTTCAAAGCA TTGAAAAAAA TCTACTGATA CTTACTTTCT TAGACAAGTA

- 3001 GTTCTTAGTT AACCACCAAT GGAACTGGGT TCATTCTGAA TCCTGGAGGA

- 3051 GCTTCCTCGT GCCACCCAGT GTTTCTGGGC CCTCTGTGTG AGCAGCCAGG

- 3101 TGTGAGCTGT TTTAGAAGCA GCGTGTTGCC TTCATCTCTC CCGTTTCCCA

- 3151 AAAGAACAAA GGATAAAGGT GACAGTCACA CTCCTGGGTT AAAAAAAGCA

- 3201 TTCCAGAACC ACTTCTCTTT ATGGGCACAA CAACAAAGAA GCTAAGTTCG

- 3251 CCTACCCAAA TGAAAGTAGG CTTTACAGTC AAGTACTTCT GTTGATTGCT

- 3301 AAATAACTTC ATTTTCTTGA AATAGAGCAA CTTTGAGTGA AATCTGCAAC

- 3351 ATGGATACCA TGTATGTAAG ATACTGCTGT ACAGAAGAGT TAAGGCTTAC

- 3401 AGTGCAAATG AGGCGTCAGC TTTGGGTGCT AAAATTAACA AGTCTAATAT

- 3451 TATTACCATC AATCAGGAAG AGATAATAAA TGTTTAAACA AACACAGCAG

- 3501 TCTGTATAAA AATACGTGTA TATTTACTCT TTCTGTGCAC GCTCTATAGC

FIGURE 15E

- 3551 ATAGGCAGGA GAGGCTTATG TGGCAGCACA AGCCAGGTGG GGATTTTGTA

- 3601 AAGAAGTGAT AAAACATTTG TAAGTAATCC AAGTAGGAGA TATTAAGGCA

- 3651 CCAAAAGTAA CATGGCACCC AACACCCAAA AATAAAAATA TGAAATATGA

- 3701 GTGTGAACTC TGAGTAGAGT ATGAAACACC ACAGAAAGTC TTAGAAATAG

- 3751 CTCTGGAGTG GCTCTCCCAG GACAGTTTCC AGTTGGCTGA ATAGTCTTTT

- 3801 GGCACTGATG TTCTACTTCT TCACATTCAT CTAAAAAAAA AAAAAAAAA

HUMAN PROSTATE TUMOR INDUCING GENE-1 AND USES THEREOF

This application is a continuation-in-part of U.S application Ser. No. 08/351,888, filed Dec. 8, 1994, which is a continuation of U.S. Ser. No. 08/225,493, filed Apr. 11, 1994, now abandoned, which is a continuation of U.S. Ser. No. 08/106,323, filed Aug. 13, 1993, now abandoned, which is a continuation of U.S. Ser. No. 07/603,804, filed Oct. 25, 1990, now abandoned, the contents of which are hereby incorporated by reference.

The invention disclosed herein was made with Government support under NIH Grants CA 35675 and CA 43208 from the Department of Health and Human Services. Accordingly, the U.S. Government has certain rights in this invention.

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of each series of experiments.

The classical method for developing monoclonal antibodies specific for cell-surface molecules involves repeated injections of mice with either intact cells or cell membrane preparations derived from the desired target cells. The injections are followed by the removal of mouse spleen cells and fusion of these cells to a myeloma partner [reviewed in (1–3)]. This approach has resulted in the production of monoclonal antibodies that react with a number of surface-expressed molecules of potential interest, including cell-surface growth factor receptors and tumor-associated antigens. However, the procedure is generally inefficient and requires screening of a large number of hybridomas for production of the appropriate monoclonal antibodies [reviewed in (1–6)].

DNA transfection procedures have been used to transfer human genes into heterologous cells, such as mouse NIH 3T3 cells [reviewed in 7–10)]. When NIH 3T3 cells have been used as the recipient for DNA transfection, this approach has not been successful in identifying dominant-acting transforming or tumor-inducing genes from a majority (approximately 85%) of human tumors or human tumor cell lines (7–10). In most studies that use NIH 3T3 cells, even when a dominant-acting oncogene was identified, it often represented a member of the ras oncogene family or a modified cellular gene (7–10). A recently developed cloned rat embryo fibroblast cell line, CREF-Trans 6, has proven useful in identifying putative novel oncogenes not detected in NIH 3T3 cells (11). Cotransfection of CREF-Trans 6 cells with high-molecular-weight DNA from the LNCaP human prostatic carcinoma cell line and the selectable neomycin resistance gene (pSV2neo), followed by selection for resistance to G418 and injection into nude mice, resulted in tumor formation (11). In contrast, when the same DNA sources were used with NIH 3T3 cells, no tumors developed in nude mice given an injection of neomycin-resistant (G418) cotransfected NIH 3T3 cells (11).

Applicants conducted the current experiments to determine if DNA transfection combined with an immunologic masking tactic could be used to efficiently generate hybridomas that secrete monoclonal antibodies reacting with cell-surface molecules expressed on genetically altered cells. Applicants demonstrate the feasibility of this approach, called surface-epitope masking (SEM). Applicants used DNA transfection and the SEM procedure in an attempt to produce hybridomas secreting monoclonal antibodies that reacted with surface epitopes located on typical multidrug-resistant (MDR) cells and human prostatic carcinoma cells. These results indicate that DNA transfection in conjunction with SEM can be used to generate hybridomas producing monoclonal antibodies that can react with surface-expressed molecules encoded by both known and unknown genes.

SUMMARY OF THE INVENTION

This invention provides a method for preparing a hybridoma cell line which produces an antibody capable of specifically binding to a cell surface-expressed protein which expresses on the surface of one cell type but not the other comprises a) generating antiserum against a cell type which does not express the cell surface-expressed protein; b) coating another cell type which expresses the cell surface-expressed protein with the antiserum generated; c) injecting the antiserum-coated cells into suitable hosts; d) screening the resulting hosts to identify hosts which produce serum reactive with the coated cell; e) removing spleens from the hosts so identified; f) preparing from the spleens so removed hybridomas; and g) recovering therefrom a hybridoma cell line which produces an antibody capable of specifically binding to a cell surface-expressed protein.

This invention provides a method for isolating DNA coding for a protein capable of binding to the cell surface-expressed protein which expresses on the surface of one cell type but not the other comprising: a) generating antiserum against a cell type which does not express the cell surface-expressed protein; b) coating another cell type which expresses the cell surface-expressed protein with the antiserum generated; c) injecting the antiserum-coated cells into suitable hosts; d) screening the resulting hosts to identify hosts which produce serum reactive with the coated cell; e) removing spleens from the hosts so identified; f) isolating B-lymphocytes from the removed spleen; g) preparing DNA from plasma cells to generate combinatorial phage cDNA library which contains different clones; and h) contacting the clones in the library with the coated cells from step (b), the binding of the coated cells with a clone indicating the protein expressed by the clone capable of binding to the cell surface-expressed protein.

This invention provides a method for preparing a hybridoma cell line which produces an antibody capable of specifically binding to a cell surface-expressed protein which expresses on the surface of one cell type but not the other comprises: a) generating antiserum against a cell type which does not express the cell surface-expressed protein; b) coating another cell type which expresses the cell surface-expressed protein with the antiserum generated; c) contacting the antiserum-coated cells with suitable immunoresponsive cells capable of being stimulated to produce antibodies; d) preparing immunoresponsive cells to produce hybridomas; and e) isolating hybridomas which produce antibodies reactive with the coated cell, thereby preparing hybridoma cell lines which produce antibodies capable of specifically binding to a cell surface-expressed protein.

This invention provides a method for preparing a hybridoma cell line which produces an antibody capable of specifically binding to a cell surface-expressed protein comprises: a) generating antiserum against a cell which normally does not express the cell surface-expressed protein; b)

introducing a DNA molecule encoding the cell surface-expressed protein to express the cell surface-expressed protein into the cell; c) selecting cells which express the cell surface-expressed protein; d) coating the selected cells with the antiserum generated in step a; e) injecting the antiserum-coated cells into suitable hosts; f) screening the resulting hosts to identify hosts which produce serum reactive with the coated cell; g) removing spleens from the hosts so identified; h) preparing from the spleens so removed hybridomas; and i) recovering therefrom a hybridoma cell line which produces an antibody capable of specifically binding to a cell surface-expressed protein.

This invention provides a method for isolating DNA coding for a protein capable of binding to the cell surface-expressed protein comprising: a) generating antiserum against a cell which normally does not express the cell surface-expressed protein; b) introducing a DNA molecule which encodes the cell surface-expressed protein to express the cell surface-expressed protein into the cell; c) selecting cells which express the cell surface-expressed protein; d) coating the selected cells with the antiserum generated in step a; e) injecting the antiserum-coated cells into suitable hosts; f) screening the resulting hosts to identify hosts which produce serum reactive with the coated cell; g) removing spleens from the hosts so identified; h) isolating B-lymphocytes from the removed spleen; i) preparing DNA from B-lymphocytes to generate combinatorial phage cDNA library which contains different clones; and j) contacting the clones in the library with the coated cells from step (b), the binding of the coated cells with a clone indicating the protein expressed by the clone capable of binding to the cell surface-expressed protein.

This invention provides a method for preparing a hybridoma cell line which produces an antibody capable of specifically binding to a cell surface-expressed protein which expresses on the surface of one cell type but not the other comprises: a) generating antiserum against a cell which does not express the cell surface-expressed protein; b) introducing a DNA molecule which encodes the cell surface-expressed protein to express the cell surface-expressed protein into the cell; c) selecting cells which express the cell surface-expressed protein; d) coating the selected cells with the antiserum generated in step a; e) contacting the antiserum-coated cells with suitable immunoresponsive cells capable of being stimulated to produce antibodies; f) preparing immunoresponsive cells to produce hybridomas; and g) isolating hybridomas which produce antibodies reactive with the coated cell, thereby preparing hybridoma cell lines which produce antibodies capable of specifically binding to a cell surface-expressed protein.

This invention provides a method for preparing a hybridoma cell line which produces an antibody capable of specifically binding to a cell surface-expressed protein comprises: a) introducing a DNA molecule which encodes a cell surface-expressed protein and a second DNA molecule which encodes a selectable or identifiable trait into an established cell line; b) selecting transfected cells which express the selectable or identifiable trait; c) recovering the transfected cells so selected; d) coating the selected cells so recovered with an antiserum generated against the established cell line; e) injecting the antiserum-coated cells into the suitable hosts; f) screening the resulting hosts to identify hosts which produce serum reactive with the coated cell; g) removing spleens from the hosts so identified; h) preparing from the spleens so removed hybridomas; and i) recovering therefrom a hybridoma cell line which produces an antibody capable of specifically binding to a cell surface-expressed protein.

This invention provides a method for isolating DNA coding for a protein capable of binding to the cell surface-expressed protein comprising: a) introducing a DNA molecule which encodes a cell surface-expressed protein and a second DNA molecule which encodes a selectable or identifiable trait into an established cell line; b) selecting transfected cells which express the selectable or identifiable trait; c) recovering the transfected cells so selected; d) coating the selected cells so recovered with an antiserum generated against the established cell line; e) injecting the antiserum-coated cells into the suitable hosts; f) screening the resulting hosts to identify hosts which produce serum reactive with the coated cell; g) removing spleens from the hosts so identified; h) isolating B-lymphocytes from the removed spleen; i) preparing DNA from B-lymphocytes to generate combinatorial phage cDNA library which contains different clones; and j) contacting the clones in the library with the coated cells from step (b), the binding of the coated cells with a clone indicating the protein expressed by the clone capable of binding to the cell surface-expressed protein.

This invention provides a method for preparing a hybridoma cell line which produces an antibody capable of specifically binding to a cell surface-expressed protein comprises a) introducing a DNA molecule which encodes a cell surface-expressed protein and a second DNA molecule which encodes a selectable or identifiable trait into an established cell line; b) selecting transfected cells which express the selectable or identifiable trait; c) recovering the transfected cells so selected; d) coating the selected cells so recovered with an antiserum generated against the established cell line; e) contacting the antiserum-coated cells with suitable immunoresponsive cells capable of being stimulated to produce antibodies; f) preparing immunoresponsive cells to produce hybridomas; and g) isolating hybridomas which produce antibodies reactive with the coated cell of step (d), thereby preparing hybridoma cell lines which produce antibodies capable of specifically binding to a cell surface-expressed protein.

This invention provides a method for preparing a hybridoma cell line which produces an antibody which specifically recognizes and binds to a tumor associated antigen associated with a neoplastic, human cell which comprises: a) cotransfecting the CREF-Trans 6 cell line (ATCC Accession No. CRL 10584) with DNA isolated from a neoplastic, human cell and DNA which encodes a selectable or identifiable trait; b) selecting transfected cells which express the selectable or identifiable trait; c) recovering the transfected cells so selected; d)injecting the transfected cells so recovered into a suitable first murine host; e) maintaining the resulting first murine host for a period of time effective to induce the injected transfected cells to form a tumor in the first murine host; f) isolating the resulting tumor from the first murine host; g) obtaining tumor cells from the tumor so isolated; h) coating the tumor cells so obtained with an antiserum generated against the established non-human, non-tumorigenic cell line; i) injecting the antiserum-coated cells into the suitable second hosts; j) screening the resulting second hosts to identify hosts which produce serum reactive with the neoplastic, human cell; k) removing spleens from the second hosts so identified;l) preparing from the spleens so removed hybridomas; and m) recovering therefrom a hybridoma cell line which produces an antibody which specifically recognizes and binds to the cell surface antigen.

This invention provides a method of preparing DNA encoding a cell surface antigen associated with a neoplastic, human cell which comprises:a)cotransfecting CREF-Trans 6 cell line with DNA isolated from a neoplastic human cell and DNA encoding a selectable or identifiable trait;b) selecting transfected cells which express the selectable or identifiable trait;c) recovering the transfected cells so selected;d) injecting the transfected cells so recovered into a suitable first murine host;e)maintaining the resulting first murine host for a period of time effective to induce the injected transfected cells to form a tumor in the first murine host;f)isolating the resulting tumor from the first murine host;g)obtaining tumor cells from the tumor so isolated; and h) recovering DNA encoding the cell surface antigen associated with the neoplastic human cell from the tumor cells so obtained.

This invention further provides an isolated mammalian nucleic acid molecule having the sequence of Prostate Carcinoma Tumor Antigen Gene-1. This invention also provides an isolated mammalian nucleic acid molecules having the sequence of Prostate Tumor Inducing Gene-1. This invention provides an isolated mammalian nucleic acid molecules having the sequence of Prostate Tumor Inducing Gene-2. Finally, this invention provides an isolated mammalian nucleic acid molecules having the sequence of Prostate Tumor Inducing Gene-3.

BRIEF DESCRIPTION OF THE FIGURES

FIGS. 8A–8D Peptide and DNA sequence of the PTI-1 gene and comparison with the human EF-1α gene. (A and B) Peptide and DNA sequence of PTI-1. The 5'- and 3'-non-translation region of the PTI-1 gene is in small letters and the PTI-1 open-reading frame is in capital letters. Squared amino acids are mutated amino acids in the PTI-1 gene resulting from single-base mutations (underlined bases). The sequences underlined in the 5'-non-translated regions are the L and A primers, used in FIGS. 7 and 9. (C) Peptide comparison of EF-1α and PTI-1. Peptide for EF-1α is indicated in (E) and the peptide for PTI-1 is indicated in (P). The underlined region (67 amino acids) of EF-1α indicates the amino acids missing in the PTI-1 gene. Bold letters (with a *) indicate the mutated amino acids in the PTI-1 peptide. (D) Differences in amino acids, codons and nucleotides between EF-1α and PTI-1. Six single-base mutations give rise to specific amino acid changes in the PTI-1 gene. In the column of amino acids, the numbers in parentheses refer to the position of the amino acid in the peptide and codon refers to the sequence of three nucleotides encoding the specific amino acid. The specific nucleotide change is also indicated.

(antisense orientation) (both underlined in FIG. 8A. RT-PCR of PSA uses the primers (A) 5'-AGACACAGGCCAGGTATTTCAGGTC-3' (SEQ. ID NO.3) and (B) 5'-CACGATGGTGTCCTTGATCCACTTC-3' (SEQ. ID NO.4). RT-PCR of GAPDH uses a pair of primers with the sequences (I) (5'-TCTTACTCCTTGGAGGCCATG-3') (SEQ. ID NO.5) and P (II) (5'-CGTCTTCACCACCATGGAGAA-3') (SEQ. ID NO.6). The PCR amplified products were blotted on nylon membranes and probed with a [$^{32}$p]-labeled 279 bp DNA fragment of PTI-1, PSA or GAPDH, respectively.

Figure 10:
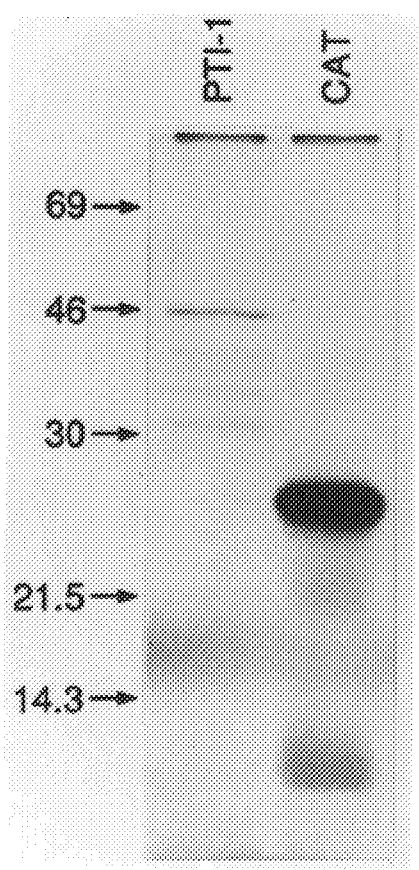

FIG. 10 In vitro translation of the PTI-1 gene. Lane CAT is the in vitro translation of the chloramphenicol acetyltransferase gene ($M_r$=24 kDa), used as a positive control. Lane PTI-1 contains the translated products of the PTI-1 gene. Rainbow protein standards (Amersham Life Science) were used to determine the sizes of the in vitro translated products.

Figure 11:
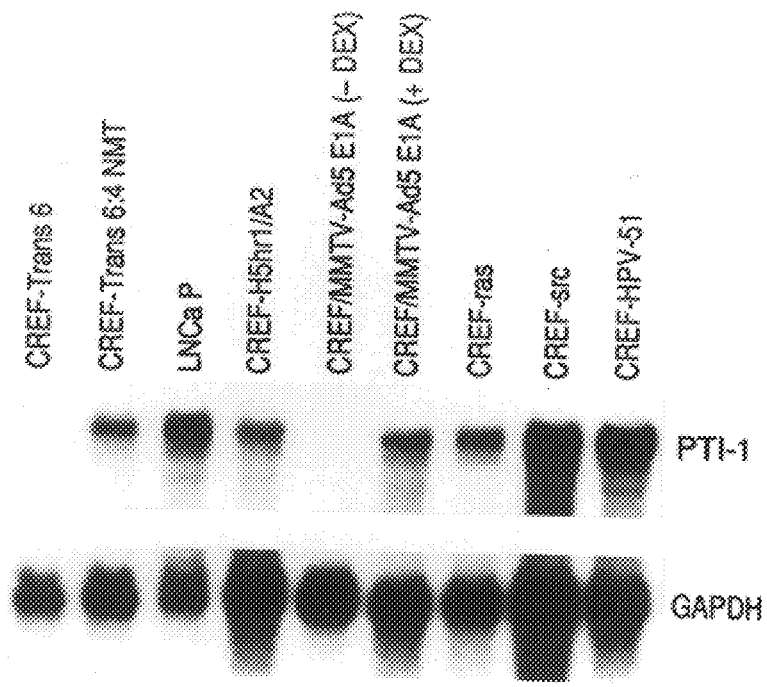
Figure 12A:
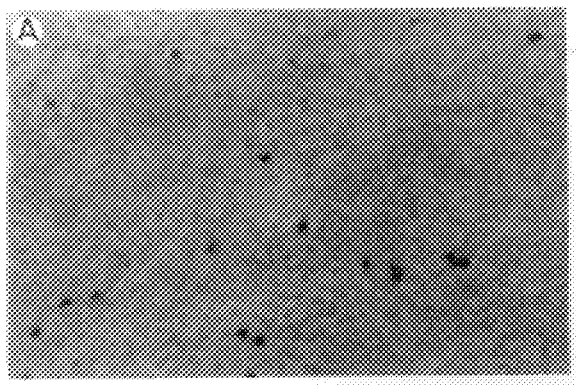
Figure 12B:
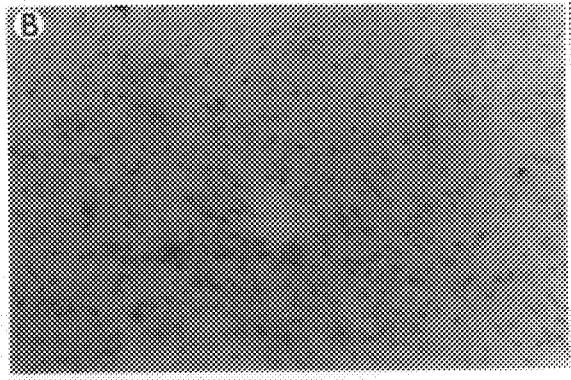
Figure 12C:
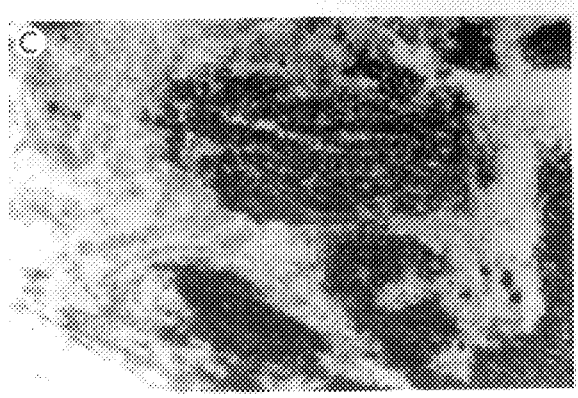
Figure 12D:
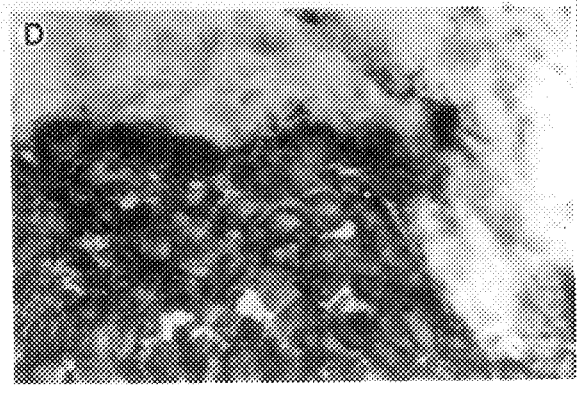

FIG. 11 Expression of PTI-1 in CREF cells transformed by different oncogenes. Northern hybridization analysis of RNA isolated from: CREF-Trans 6; LNCaP DNA transfected nude mouse tumor-derived CREF-Trans 6 cells (CREF-Trans 6:4 NMT); LNCaP; CREF cells transformed by a mutant of type 5 adenovirus (CREF-H5hr1/A2); CREF cells transformed by a dexamethasone inducible (mouse mammary tumor virus (MMTV) promoter) wild type 5 adenovirus transforming E1A gene (CREF/MMTV-Ad5E1A) in the absence of DEX (−DEX) normal cellular phenotype, in the presence of DEX (+DEX) Ad5 E1A expressed and cells are transformed; CREF cells transformed by Haras oncogene (CREF-ras); CREF cells transformed by v-src oncogene (CREF-src); and CREF cells transformed by oncogenic human papilloma virus type 51 (CREF-HPV-51). Blots probed with a $^{32}$P-labeled PTI-1 gene probe, then stripped and reprobed with a $^{32}$P-labeled GAPDH gene probe.

FIG. 12A–12D Reactivity of Br-car (breast carcinoma) monoclonal antibodies (MAbs) prepared by the surface epitope masking (SEM) technique toward fresh-frozen sections of human cancers. Sections were prepared from patients with metastatic melanoma (A) small cell lung carcinoma (B) and breast carcinomas (C and D). Reactivity was determined using immunohistochemical techniques with MAbs prepared using the SEM procedure with nude mouse tumor-derived CREF-Trans 6 cells transfected with DNA from the human breast carcinoma cell line T47D, CREF-Trans 6: T47D NMT. Reactivity is only apparent in the two human breast carcinoma sectioned patient samples.

FIG. 13A–13B Nucleic acid sequence of PTI-2

FIG. 14A–14B Nucleic acid sequence of PTI-3

FIG. 15A–15E Nucleic acid sequence of PCTA-1

DETAILED DESCRIPTION OF THE INVENTION

Throughout this application, the following standard abbreviations are used throughout the specification to indicate specific nucleotides:

| | |
|---|---|
| C = cytosine | A = adenosine |
| T = thymidine | G = guanosine |

This invention provides a method for preparing a hybridoma cell line which produces an antibody capable of specifically binding to a cell surface-expressed protein which expresses on the surface of one cell type but not the other comprises a) generating antiserum against a cell type which does not express the cell surface-expressed protein; b) coating another cell type which expresses the cell surface-expressed protein with the antiserum generated; c) injecting the antiserum-coated cells into suitable hosts; d) screening the resulting hosts to identify hosts which produce serum reactive with the coated cell; e) removing spleens from the hosts so identified; f) preparing from the spleens so removed hybridomas; and g) recovering therefrom a hybridoma cell line which produces an antibody capable of specifically binding to a cell surface-expressed protein.

This invention provides a method for isolating DNA coding for a protein capable of binding to the cell surface-expressed protein which expresses on the surface of one cell type but not the other comprising: a) generating antiserum against a cell type which does not express the cell surface-expressed protein; b) coating another cell type which expresses the cell surface-expressed protein with the antiserum generated; c) injecting the antiserum-coated cells into suitable hosts; d) screening the resulting hosts to identify hosts which produce serum reactive with the coated cell; e) removing spleens from the hosts so identified; f) isolating B-lymphocytes from the removed spleen; g) preparing DNA from plasma cells to generate combinatorial phage cDNA library which contains different clones; and h) contacting the clones in the library with the coated cells from step (b), the binding of the coated cells with a clone indicating the protein expressed by the clone capable of binding to the cell surface-expressed protein.

This invention provides a method for preparing a hybridoma cell line which produces an antibody capable of specifically binding to a cell surface-expressed protein which expresses on the surface of one cell type but not the other comprises: a) generating antiserum against a cell type which does not express the cell surface-expressed protein; b) coating another cell type which expresses the cell surface-expressed protein with the antiserum generated; c) contacting the antiserum-coated cells with suitable immunoresponsive cells capable of being stimulated to produce antibodies; d) preparing immunoresponsive cells to produce hybridomas; and e) isolating hybridomas which produce antibodies reactive with the coated cell, thereby preparing hybridoma cell lines which produce antibodies capable of specifically binding to a cell surface-expressed protein.

This invention provides a method for preparing a hybridoma cell line which produces an antibody capable of specifically binding to a cell surface-expressed protein comprises: a) generating antiserum against a cell which normally does not express the cell surface-expressed protein; b) introducing a DNA molecule encoding the cell surface-expressed protein to express the cell surface-expressed protein into the cell; c) selecting cells which express the cell surface-expressed protein; d) coating the selected cells with the antiserum generated in step a; e) injecting the antiserum-coated cells into suitable hosts; f) screening the resulting hosts to identify hosts which produce serum reactive with the coated cell; g) removing spleens from the hosts so identified; h) preparing from the spleens so removed hybridomas; and i) recovering therefrom a hybridoma cell line which produces an antibody capable of specifically binding to a cell surface-expressed protein.

This invention provides a method for isolating DNA coding for a protein capable of binding to the cell surface-expressed protein comprising: a) generating antiserum against a cell which normally does not express the cell surface-expressed protein; b) introducing a DNA molecule which encodes the cell surface-expressed protein to express the cell surface-expressed protein into the cell; c) selecting cells which express the cell surface-expressed protein; d) coating the selected cells with the antiserum generated in step a; e) injecting the antiserum-coated cells into suitable hosts; f) screening the resulting hosts to identify hosts which produce serum reactive with the coated cell; g) removing spleens from the hosts so identified; h) isolating B-lymphocytes from the removed spleen; i) preparing DNA from B-lymphocytes to generate combinatorial phage cDNA library which contains different clones; and j) contacting the clones in the library with the coated cells from step (b), the binding of the coated cells with a clone indicating the protein expressed by the clone capable of binding to the cell surface-expressed protein.

This invention provides a method for preparing a hybridoma cell line which produces an antibody capable of specifically binding to a cell surface-expressed protein which expresses on the surface of one cell type but not the other comprises: a) generating antiserum against a cell which normally does not express the cell surface-expressed protein; b) introducing a DNA molecule which encodes the cell surface-expressed protein to express the cell surface-expressed protein into the cell; c) selecting cells which express the cell surface-expressed protein; d) coating the selected cells with the antiserum generated in step a; e) contacting the antiserum-coated cells with suitable immunoresponsive cells capable of being stimulated to produce antibodies; f) preparing immunoresponsive cells to produce hybridomas; and g) isolating hybridomas which produce antibodies reactive with the coated cell, thereby preparing hybridoma cell lines which produce antibodies capable of specifically binding to a cell surface-expressed protein.

This invention provides a method for preparing a hybridoma cell line which produces an antibody capable of specifically binding to a cell surface-expressed protein comprises: a) introducing a DNA molecule which encodes a cell surface-expressed protein and a second DNA molecule which encodes a selectable or identifiable trait into an established cell line; b) selecting transfected cells which express the selectable or identifiable trait; c) recovering the transfected cells so selected; d) coating the selected cells so recovered with an antiserum generated against the established cell line; e) injecting the antiserum-coated cells into the suitable hosts; f) screening the resulting hosts to identify hosts which produce serum reactive with the coated cell; g) removing spleens from the hosts so identified; h) preparing from the spleens so removed hybridomas; and i) recovering therefrom a hybridoma cell line which produces an antibody capable of specifically binding to a cell surface-expressed protein.

This invention provides a method for isolating DNA coding for a protein capable of binding to the cell surface-expressed protein comprising: a) introducing a DNA molecule which encodes a cell surface-expressed protein and a second DNA molecule which encodes a selectable or identifiable trait into an established cell line; b) selecting transfected cells which express the selectable or identifiable trait; c) recovering the transfected cells so selected; d) coating the selected cells so recovered with an antiserum generated against the established cell line; e) injecting the antiserum-coated cells into the suitable hosts; f) screening the resulting hosts to identify hosts which produce serum reactive with the coated cell; g) removing spleens from the hosts so identified; h) isolating B-lymphocytes from the removed spleen; i) preparing DNA from B-lymphocytes to generate combinatorial phage cDNA library which contains different clones; and j) contacting the clones in the library with the coated cells from step (b), the binding of the coated cells with a clone indicating the protein expressed by the clone capable of binding to the cell surface-expressed protein.

This invention provides a method for preparing a hybridoma cell line which produces an antibody capable of specifically binding to a cell surface-expressed protein comprises a) introducing a DNA molecule which encodes a cell surface-expressed protein and a second DNA molecule which encodes a selectable or identifiable trait into an established cell line; b) selecting transfected cells which express the selectable or identifiable trait; c) recovering the transfected cells so selected; d) coating the selected cells so recovered with an antiserum generated against the established cell line; e) contacting the antiserum-coated cells with suitable immunoresponsive cells capable of being stimulated to produce antibodies; f) preparing immunoresponsive cells to produce hybridomas; and g) isolating hybridomas which produce antibodies reactive with the coated cell of step (d), thereby preparing hybridoma cell lines which produce antibodies capable of specifically binding to a cell surface-expressed protein.

In an embodiment, the DNA molecules are introduced into the establised cell line by cotransfection.

In another embodiment, the DNA molecule encoding a cell surface-expressed protein is a expression vector.

In another embodiment, the cell surface-expressed protein is the P-glycoprotein.

In another embodiment, the cell surface-expressed protein is a cytokine receptor.

In a further embodiment, the cytokine receptor is a interferon-alpha receptor.

In still another embodiment, the cytokine receptor is a interferon-gamma receptor.

In yet another embodiment, the cell surface-expressed protein is a tumor associated antigen.

In a still further embodiment, the second DNA molecule encoding the selectable or identifiable trait is plasmid DNA.

In another embodiment, the plasmid DNA encodes resistance to an antibiotic.

In still another embodiment, the plasmid DNA comprises pSV2-Neo.

In another embodiment, the cell line is the CREF-Trans 6 cell line (ATCC Accession No. CRL 10584).

This invention provides a method for preparing a hybridoma cell line which produces an antibody which specifically recognizes and binds to a tumor associated antigen associated with a neoplastic, human cell which comprises: a) cotransfecting the CREF-Trans 6 cell line (ATCC Accession No. CRL 10584) with DNA isolated from a neoplastic, human cell and DNA which encodes a selectable or identifiable trait; b) selecting transfected cells which express the selectable or identifiable trait; c) recovering the transfected cells so selected; d) injecting the transfected cells so recovered into a suitable first murine host; e) maintaining the resulting first murine host for a period of time effective to induce the injected transfected cells to form a tumor in the first murine host; f) isolating the resulting tumor from the first murine host; g) obtaining tumor cells from the tumor so isolated; h) coating the tumor cells so obtained with an antiserum generated against the established non-human, non-tumorigenic cell line; i) injecting the antiserum-coated cells into the suitable second hosts; j) screening the resulting second hosts to identify hosts which produce serum reactive with the neoplastic, human cell; k) removing spleens from the second hosts so identified;l) preparing from the spleens so removed hybridomas; and m) recovering therefrom a hybridoma cell line which produces an antibody which specifically recognizes and binds to the cell surface antigen.

In an embodiment, the neoplastic, human cell is a benign cell. In another embodiment, the neoplastic, human cell is a metatastic cell. In a separate embodiment, the neoplastic, human cell is a human prostatic carcinoma cell derived from cell line LNCaP (ATCC No. CRL 1740).

In another embodiment, the cell is a human breast carcinoma cell derived from cell line T47D (ATCC No. HTB 133).

In an embodiment, the suitable second host is a murine host. In another embodiment, the suitable second host is a non-human primate host.

This invention provides a method of preparing DNA encoding a cell surface antigen associated with a neoplastic, human cell which comprises: a) cotransfecting CREF-Trans 6 cell line with DNA isolated from a neoplastic human cell and DNA encoding a selectable or identifiable trait; b) selecting transfected cells which express the selectable or identifiable trait; c) recovering the transfected cells so selected; d) injecting the transfected cells so recovered into a suitable first murine host; e) maintaining the resulting first murine host for a period of time effective to induce the injected transfected cells to form a tumor in the first murine host; f) isolating the resulting tumor from the first murine host; g) obtaining tumor cells from the tumor so isolated; and h) recovering the DNA encoding the cell surface antigen associated with the neoplastic human cell from the tumor cells so obtained. The DNA molecule containing the sequence for the cell surface antigen associated with the neoplastic human cell may be further isolated.

In an embodiment, the neoplastic, human cell is a benign tumor cell. In another embodiment, the neoplastic, human cell is a metastatic cell. In a separate embodiment, the neoplastic, human cell is a human prostatic carcinoma cell derived from cell line LNCaP (ATCC No. CRL 1740). In another embodiment, the neoplastic, human cell is a human breast carcinoma cell derived from cell line T47D (ATCC No. HTB 133). In a still another embodiment, the neoplastic, human small cell lump carcinoma NCI/H69. In another embodiment, the neoplastic, human cell is a human glioblastoma multiform (stage IV astrocytoma) cell derived from cell line GBM-18 (ATCC No. CCL 228). In a further embodiment, the neoplastic, human cell is a patient-derived metastatic colon carcinoma.

In a separate embodiment, the DNA encoding the selectable or identifiable trait is plasmid DNA encoding resistance to an antibiotic. In a further embodiment, the plasmid DNA comprises pSV2-Neo and the selection is by the antibiotic G418.

The cell surface antigen of the above-described method includes but not limited to a tumor associated antigen, a growth factor receptor, a viral-encoded surface-expressed antigen, a oncogene product, a surface epitope, a membrane protein which mediates classical multi-drug resistance, a membrane protein which mediates atypical multi-drug resistance, an antigen which mediates a tumorigenic phenotype, an antigen which mediates a metastatic phenotype, an antigen which suppresses a tumorigenic phenotype, an antigen which suppresses a metastatic phenotype and cytokine receptors including the human interferon α and interferon γ receptors.

In an embodiment, the cell surface antigen is an antigen which is recognized by a specific immunological effector cell. In a further embodiment, the specific immunological effector cell is a T-cell.

In a separate embodiment, the cell surface antigen is an antigen which is recognized by a non-specific immunological effector cell. In a further embodiment, the non-specific immunological effector cell is a macrophage cell. In a still further embodiment, the non-specific immunological effector cell is a natural killer cell.

This invention provides the DNA prepared the above-described method. This invention also provides nucleic acid probes hybridizable with the isolated DNA molecule. The nucleic acid probe may be DNA or RNA. In an embodiment, the nucleic acid probe is labeled with a detectable marker. In a further embodiment, the DNA probe is labeled with a detectable marker.

This invention also provides a method of diagnosing in a subject a neoplastic condition which comprises contacting a sample from the subject with the above-described DNA probe under conditions permitting the DNA probe to hybridize with the DNA associated with the neoplastic condition, detecting the presence of hybridized DNA, and thereby diagnosing the neoplastic condition.

This invention also provides monoclonal antibody designated Pro 1.1.; monoclonal antibody designated Pro 1.2.; monoclonal antibody designated Pro 1.3.; monoclonal antibody designated Pro 1.4.; and monoclonal antibody designated Pro 1.5.

This invention provides an isolated mammalian nucleic acid molecule having the sequence of Prostate Carcinoma Tumor Antigen Gene-1. The nucleic acid molecule may be DNA, cDNA or RNA. This invention also provides isolated human nucleic acid molecule.

The nucleic acid molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

This invention also provides nucleic acid molecule of at least 15 nucleotides capable of specifically hybridizing with a sequence of Prostate Carcinoma Tumor Antigen Gene-1.

This nucleic acid molecule produced can either be DNA or RNA. As used herein, the phrase "specifically hybridizing" means the ability of a nucleic acid molecule to recognize a nucleic acid sequence complementary to its own and to form double-helical segments through hydrogen bonding between complementary base pairs.

This nucleic acid molecule of at least 15 nucleotides capable of specifically hybridizing with a sequence of a Prostate Carcinoma Tumor Antigen Gene-1 can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a Prostate Carcinoma Tumor Antigen Gene-1 DNA molecule into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the Prostate Carcinoma Tumor Antigen Gene-1 DNA molecule downstream of a bacteriophage promoter such as T3, T7 or SP6. Large amounts of RNA probe may be produced by incubating the labeled nucleotides with the linearized DNA fragment where it contains an upstream promoter in the presence of the appropriate RNA polymerase.

This invention provides an isolated mammalian nucleic acid molecule having the sequence of Prostate Carcinoma Tumor Antigen Gene-1 operatively linked to a promoter of RNA transcription.

This invention also provides vectors which comprises the isolated mammalian nucleic acid molecule having the sequence of Prostate Carcinoma Tumor Antigen Gene-1. In an embodiment, the vector is a plasmid.

This invention also provides the plasmid designated PCTA-1. This plasmid, PCTA-1, was deposited on Jan. 11, 1995 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, PCTA-1, was accorded ATCC Accession Number ATCC 97021.

PCTA-1 gene contains 3850 bp. It was cloned into the XhoI and EcoRI sites of the pBluescript vector. T3 promoter is close to 5' end and T7 promoter to 3' end of PCTA-1.

This invention provides an isolated mammalian nucleic acid molecule having the sequence of Prostate Tumor Inducing Gene-1. The nucleic acid molecule can be DNA, cDNA, genomic DNA, synthetic DNA or RNA. This invention also provides human nucleic acid molecule.

This invention further provides a nucleic acid molecule of at least 15 nucleotides capable of specifically hybridizing with a sequence of Prostate Tumor Inducing Gene-1.

This invention provides an isolated mammalian nucleic acid molecule having the sequence of Prostate Tumor Inducing Gene-1 operatively linked to a promoter of RNA transcription.

This invention provides a method of detecting expression of a Prostate Tumor Inducing Gene-1 in a cell which comprises obtaining total mRNA from the cell, contacting the mRNA so obtained with a labelled nucleic acid molecule of at least 15 nucleotides capable of specifically hybridizing with a sequence of Prostate Tumor Inducing Gene-1 under conditions permitting hybridization, and determining the presence of mRNA hybridized to the molecule, thereby detecting the expression of the Prostate Tumor Inducing Gene-1 in the cell.

In one embodiment of this invention, nucleic acids are extracted by precipitation from lysed cells and the mRNA is isolated from the extract using an oligo-dT column which binds the poly-A tails of the mRNA molecules. The mRNA is then exposed to a radioactively labelled probe on a nitrocellulose membrane, and the probe hybridizes to and thereby labels complementary mRNA sequences. Binding may be detected by luminescence autoradiography or scintillation counting. However, other methods for performing these steps are well known to those skilled in the art, and the discussion above is merely an example.

This invention also provides a method of detecting expression of a Prostate Tumor Inducing Gene-1 in tissue sections which comprises contacting the tissue sections with a labelled nucleic acid molecule of at least 15 nucleotides capable of specifically hybridizing with a sequence of Prostate Tumor Inducing Gene-1 under hybridizing conditions, determining the presence of mRNA hybridized to the molecule, and thereby detecting the expression of the Prostate Tumor Inducing Gene-1 in tissue sections.

The probes are also useful for in-situ hybridization or in order to locate tissues which express this gene, or for other hybridization assays for the presence of this gene or its mRNA in various biological tissues. The in-situ hybridization using a labelled nucleic acid molecule is well known in the art. Essentially, tissue sections are incubated with the labelled nucleic acid molecule to allow the hybridization to occur. The molecule will carry a marker for the detection because it is "labelled", the amount of the hybrid will be determined based on the detection of the amount of the marker and so will the expression of the Prostate Tumor Inducing Gene-1.

This invention provides an isolated mammalian nucleic acid molecule having the sequence of the Prostate Tumor Inducing Gene-1 operatively linked to a promoter of RNA transcription.

The isolated mammalian nucleic acid molecule having the sequence of the Prostate Tumor Inducing Gene-1 can be linked to vector systems. Various vectors including plasmid vectors, cosmid vectors, bacteriophage vectors and other viruses are well known to ordinary skilled practitioners.

This invention also provides vectors which comprises the isolated mammalian nucleic acid molecule having the sequence of the Prostate Tumor Inducing Gene-1. In an embodiment, the vector is a plasmid.

In an embodiment, the Prostate Tumor Inducing Gene-1 sequence is cloned in EcoRI/XhoI site of the Bluescript vector. This plasmid, PTI-1, clone 18, was deposited on Jan. 11, 1995 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, PTI-1, was accorded ATCC Accession Number ATCC 97020.

PTI-1 gene is determined by RACE from 1 to 215 bp and the rest by PTI-1, clone. The plasmid PTI-1 is clone 18, contains 1937 bp (29 bp+1908 bp) insert in pBluescript vector EcoRI (5' end of insert) and XhoI (3' polyA side).

The 1937 bp insert can be cut out by restriction enzymes XhoI +EcoRI. 5' end of insert is close to T3 promoter, 3' end is close to T7 promoter.

Experiments demonstrate that the 29 bp sequence of insert comes from the secondary structure of RNA so that this 29 bp sequence was not shown in complete sequence of PTI-1 gene (see FIGS. 8A–8B, and replaced by the right sequence obtained from RACE method.

The first 29 bp sequence is: 5' CGGCCCGAGCTCGT-GCCGAATTCGGCCCGAGAGCGTTAAAGT-GTGATGGCGTA CATCTT (SEQ. ID NO.7). The sequence from 30–1937 bp (1907 bp) is the sequence 216–2,123 bp (1907 bp) in complete sequence of PTI-1 FIGS. 8A–8B.

As an example to obtain these vectors, insert and vector DNA can both be exposed to a restriction enzyme to create complementary ends on both molecules which hybridize with each other and are then ligated together with DNA ligase. Alternatively, linkers can be ligated to the insert DNA which correspond to a restriction site in the vector DNA, which is then digested with the restriction enzyme which cuts at that site. Other means to obtain the vectors are also available and known to an ordinary skilled practitioner.

This invention provides a host vector system for the production of a polypeptide having the biological activity of a mammalian Prostate Tumor Inducing Gene-1 protein which comprises the above described vectors and a suitable host. These vectors may be transformed into a suitable host cell to form a host cell vector system for the production of a polypeptide.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example, the methods described above for constructing vectors in general.

This invention also provides a method of producing a polypeptide having the biological activity of a mammalian Prostate Tumor Inducing Gene-1 protein which comprises growing the host cells of the above described host vector system under suitable conditions permitting production of the polypeptide and recovering the polypeptide so produced.

This invention also provides mammalian cells comprising the above-described nucleic acid molecule.

This invention provides purified mammalian Prostate Tumor Inducing Gene-1 protein. This invention also provides a polypeptide encoded by the isolated mammalian nucleic acid molecule having the sequence of Prostate Tumor Inducing Gene-1 protein.

This invention also provides a method to produce an antibody using the above-described mammalian Prostate Tumor Inducing Gene-1 protein.

This invention provides an antibody capable of binding specifically to the mammalian Prostate Tumor Inducing Gene-1 protein. In an embodiment, the antibody is a monoclonal antibody.

This invention also provides a therapeutic agent comprising the above-described antibody and a cytoxic agent. In an embodiment, the cytotoxic agent is either a radioisotope or toxin.

This invention further provides an immunoassay for measuring the amount of a mammalian Prostate Tumor Inducing Gene-1 protein in a biological sample comprising steps of: a) contacting the biological sample with at least one of the above-described antibodies to form a complex with said antibody and the mammalian Prostate Tumor Inducing Gene-1 protein; and b) measuring the amount of the Prostate Tumor Inducing Gene-1 protein in said biological sample by measuring the amount of said complex.

This invention provides an isolated mammalian nucleic acid molecule having the sequence of Prostate Tumor Inducing Gene-2. The nucleic acid molecule can be DNA, cDNA, genomic DNA, synthetic DNA or RNA. This invention also provides human nucleic acid molecule.

This invention further provides a nucleic acid molecule of at least 15 nucleotides capable of specifically hybridizing with a sequence of Prostate Tumor Inducing Gene-2.

This invention provides an isolated mammalian nucleic acid molecule having the sequence of Prostate Tumor Inducing Gene-2 operatively linked to a promoter of RNA transcription.

This invention also provides vectors which comprises the isolated mammalian nucleic acid molecule having the sequence of Prostate Tumor Inducing Gene-2. In an embodiment, the vector is a plasmid.

This invention also provides the plasmid designated PTI-2. This plasmid, PTI-2, was deposited on Jan. 11, 1995 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, PTI-2, was accorded ATCC Accession Number ATCC 69742.

PTI-2 contains 1819 bp DNA. It was cloned into the XhoI and EcoRI site of the pBluescript vector. T3 promoter is close to the 5'-end and T7 promoter to the 3'-end of PTI-2. THe (1819 bp) insert of PTI-2 can be cut out with XhoI and EcoRI enzyme.

This invention provides an isolated mammalian nucleic acid molecule having the sequence of Prostate Tumor Inducing Gene-3. The nucleic acid molecule can be DNA, cDNA, genomic DNA, synthetic DNA or RNA. This invention also provides human nucleic acid molecule.

This invention further provides a nucleic acid molecule of at least 15 nucleotides capable of specifically hybridizing with a sequence of Prostate Tumor Inducing Gene-3.

This invention provides an isolated mammalian nucleic acid molecule having the sequence of Prostate Tumor Inducing Gene-3 operatively linked to a promoter of RNA transcription.

This invention also provides vectors which comprises the isolated mammalian nucleic acid molecule having the sequence of Prostate Tumor Inducing Gene-3. In an embodiment, the vector is a plasmid.

This invention also provides the plasmid designated PTI-3. This plasmid, PTI-3, was deposited on Jan. 11, 1995 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, PTI-3, was accorded ATCC Accession Number ATCC 97000.

PTI-3 is a partial sequence of the gene. A 1869 bp DNA of PTI-3 is inserted into PCR™II vector (3.9 kb). 5'-end of the insert is adjacent to Sp-6 promoter and 3'-end is adjacent to T7 promoter.

The insert can be cut out with EcoRI restriction enzyme to obtain the 1869 bp DNA (with extra 5 bp vector sequence at both sides).

This invention will be better understood from the Experimental Details which follow. However, one skilled in the art will readily appreciate that the specific methods and results discussed are merely illustrative of the invention as described more fully in the claims which follow thereafter.

First Series of Experiments Materials and Methods
Cell types and Culture Conditions The CREF-Trans 6 cells line (11) is a specific subclone of the Fischer F2408 rat embryo fibroblast (CREF) cell line that displays an increased sensitivity for expression of transfected genes compared with parental CREF cells (12). The LNCaP cell line was derived from metastases from a patient with advanced prostate cancer (13) and was provided by Dr. A. K. Ng (Department of Pathology, Columbia University, College of Physicians and Surgeons, New York, N.Y.). and Dr. Steven Harris (W. Alton Jones Cell Science Center, New York, N.Y.). CREF-Trans 6:4 NMT cells were derived from a tumor induced in a nude mouse following injection of G418-resistant CREF-Trans 6 cells cotransfected with DNA from LNCaP cells and a dominant-acting neomycin resistance gene (pSV2neo) (11). CREF-Trans 6:4–7 NMT cells were derived from a tumor induced in a nude mouse following injection of G418-resistant CREF- Trans 6 cells contransfected with DNA from CREF-Trans 6:4 NMT cells and the pSV2neo plasmid (11). MDR CREF-Trans 6 cells were produced by transfecting CREF-Trans 6 cells with an expression vector plasmid containing a human MDR (also known as PGY1) gene (pHaMDR1/A) (14), which was provided by Dr. Michael M. Gottesman (National Cancer Institute, Bethesda, Md.) and selecting for colchicine resistance as previously described (15).

For this study, four independent CREF-Trans 6 MDR clones were used: 1) CREF-Trans 6:MDR A1, 2) CREF-Trans 6:MDR C3, 3) CREF-Trans 6:MDR D2, and 4) CREF-Trans 6:MDR F4. All four CREF-Trans 6 MDR clones displayed increased resistance to colchicine versus parental CREF-Trans 6 cells, and they were cross-resistant to vincristine, doxorubicin, and dactinomycin (data not shown). The human prostatic carcinoma cell lines DU-145 and PC-3 were obtained from the American Type Culture Collection (Rockville, Md.) The human breast carcinoma cell line MCF7 was provided by Dr. John W. Greiner (National Cancer Institute). MCF7 CL4 C1 (MCF7 CL4) is a single-cell-derived subclone of MCF7 established in one of applicants' laboratories at Columbia University. MDR MCF7 CL4 subclones (MCF7 CL4:MDR 1, MCF7 CL4:MDR II and MCF7 CL4:MDR III) were obtained in a manner similar to that used for CREF-Trans 6 MDR clones. MCF7 CL4:MDR I, MCF7 CL4:MDR II and MCF7 CL4:MDR III cells contained MDR1 messenger RNA (mRNA), expressed the 170-kd P-glycoprotein, and displayed increased resistance to colchicine and vincristine compared with MCF7 and MCF7 CL4 cells (data not shown). GBM-18 tumor cells were derived from a patient with a stage IV astrocytoma (glioblastoma multiforme) (16). Normal human skin fibroblasts, NHSF-1, were established from a skin biopsy and provided by Dr. Armand F. Miranda (Department of Pathology, Columbia University) (17). The human melanoma cell line H0–1 was provided from a 49-year-old woman and was provided by Dr. Beppino Giovanella (Stehlin Foundation for Cancer Research, Houston, Tex.) (18). The human melanoma cell line MeWo was provided by Dr. Robert S. Kerbel (Sunnybrook Health Science Center, Toronto, Canada). The human colon carcinoma cell lines WiDr and LS174T were provided by Dr. John W. Greiner.

CREF-Trans 6, CREF-Trans 6 MDR subclone, CREF-Trans 6:4 NMT, CREF-Trans 6:4–7 NMT, H0–1 and MeWo cells were grown, at 37° C. in Dulbecco's modified Eagle's medium supplemented with 5% fetal bovine serum. Normal human skin fibroblasts (NHSF-1) as well as the LNCaP ,WiDr, LS174T, MCF7 and MCF7 CL4 cells and the MCF7 CL4 MDR subclone cells were grown in Dulbecco's modified Eagle's medium supplemented with 10% fetal bovine serum. All cells were maintained in the logarithmic phase of growth by culturing at a 1:5 or 1:10 ratio of resuspended cells to fresh medium prior to confluence.

Preparation of Mouse Polyclonal Antibodies, Enzyme-Linked Immunosorbent Assay, and SEM BALB/c female mice (8–10 weeks old ) (Charles River Breeding Laboratories, Wilmington, Mass.) were hyperimmunized with CREF-Trans 6 cells. Their care was in accordance with institutional guidelines. Animals received one subcutaneous injection of manually resuspended CREF-Trans 6 cells mixed with complete Freund's adjuvant (1:1) on day 0. On day 7, animals received a subcutaneous injection of manually resuspended CREF-Trans 6 cells mixed with incomplete Freund's adjuvant (1:1). On days 14 and 21, animals received an intraperitoneal injection of manually resuspended CREF-trans 6 cells in Hanks' phosphate-buffered solution. On day 35, mice were bled from the retro-orbital eye socket, and the sera were prepared and tested for anti-CREF-Trans 6 activity by enzyme-linked immunosorbent assay. For these assays, CREF-Trans 6 cells were grown in 96-well microtiter plates to near confluence. Cells were fixed with 3.7% formalin in phosphate-buffered solution (5 minutes at room temperature) and blocked with 10l normal goat serum (60 minutes at 37° C.). The anti-CREF-Trans 6 antisera were titered against fixed CREF-Trans 6 cells (serial dilutions of antisera, 2 hours at 37° C.) . Binding to CREF-Trans 6 cells was detected using a goat anti-mouse immunoglobulin secondary antibody conjugated to horseradish peroxidase (60 minutes at 37° C.). 3,3', 5,5'. tetramethylbenzidine (Kirkegaard and Perry, Gaithersburg, M.D.) was added in the presence of $H_2O_2$ and positive binding was monitored by a color change and quantitated by spectrophotometer (19).

In this study, the SEM procedure involved the coating of transfected CREF-Trans 6 cells with high-titer mouse anti-CREF-Trans 6 antisera to block the rat antigenic molecules prior to hyperimmunizing BALB/c mice. One to 3 million transfected CREF-Trans 6 cells were incubated overnight at 4° C. with a 1:100 dilution of mouse anti-CREF-Trans 6 antisera. Prior to the injection of polyclonal antibody-coated transfected CREF-Trans 6 cells into BALB/c mice, cells were first incubated in 1% neutral-buffered formalin for 5 minutes at 4° C. Mice were given four injections of formalin-fixed cells over a 21-day period using a protocol similar to that utilized for developing mouse anti-CREF-Trans 6 antisera. The spleens of hyperimmunized mice were removed, and spleen cells were isolated and fused with NS1 murine myeloma cells (American Type Culture Collection) to form hybridomas as previously described (19).

Immunoprecipitation Analysis

Immunoprecipitation analysis was performed as described previously (20). CREF-Trans 6, CREF-Trans 6:4 NMT, CREF-Trans 6:4–7 NMT, LNCaP, and DU-145 cells were grown to 80% confluence in 6-cm plates, starved of methionine for 1 hour at 37° C. in methionine-free medium (20) and labeled for 2 hours at 37° C. in 1 mL of the same medium with 1 mCi of [$^{35}$] methionine (Express $^{35}$S; NEN Chemicals, Boston, Mass.) . Cell lysates were prepared and immunoprecipitated with the Pro-1.4 monoclonal antibody (produced by hybridomas prepared using the SEM procedure with CREF-Trans 6:4 NMT cells) as described previously (20).

Fluorescence-Activated Cell Sorter Analysis

Fluorescence-activated cell sorter (FACS) analysis was performed as described previously (21,22). Results are expressed as mean fluorescence intensity units. Monoclonal antibodies specific for human leukocyte antigen class I antigens were supplied by Dr. Soldano Ferrone (New York Medical College, Valhalla) . All studies were performed a minimum of three times with duplicate samples in each experiment. Replicate samples within individual experiments varied 10% or less, and the variation between experiments was generally 20% or less.

Experimental Results

Figure 1:
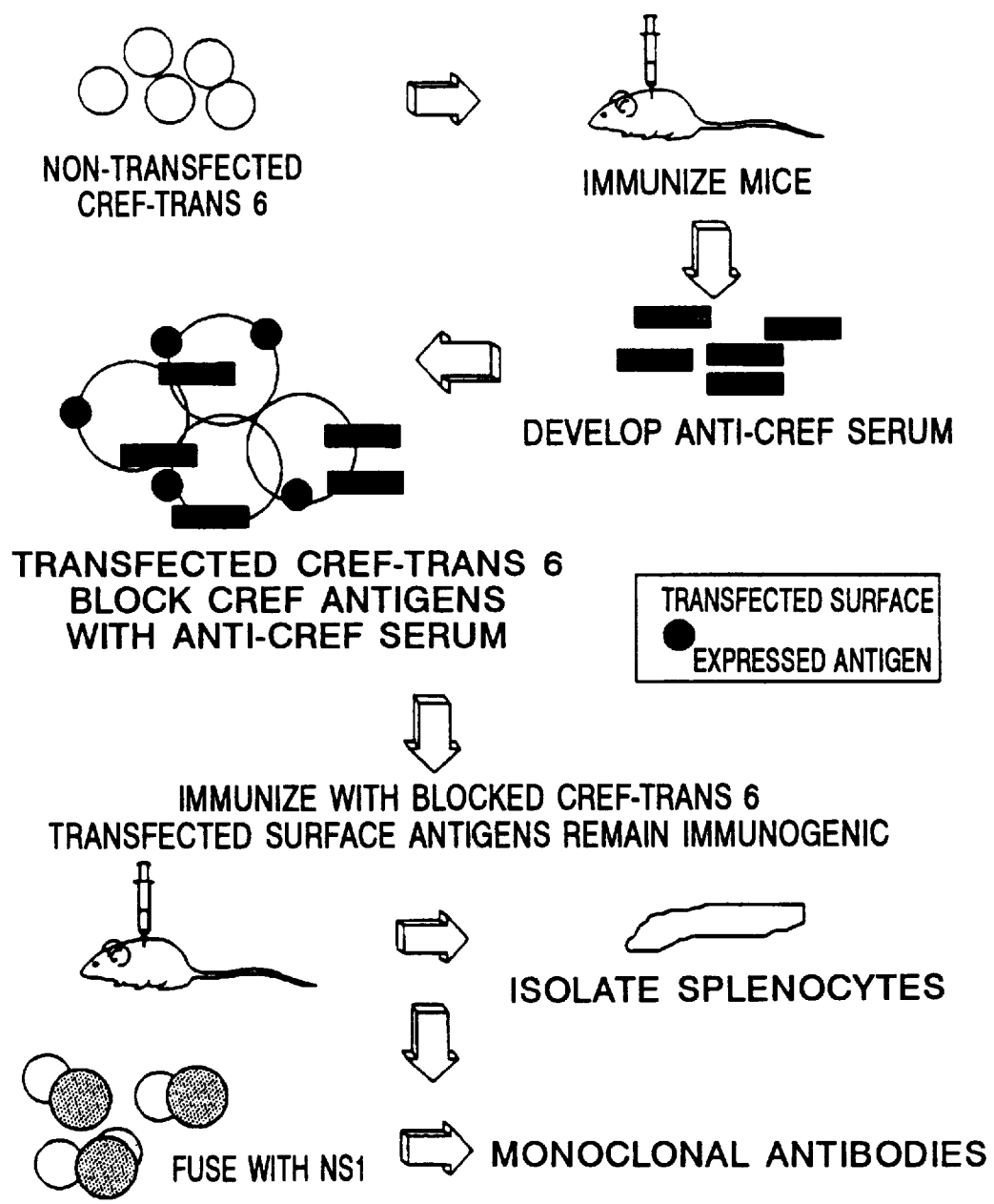
FIG. 1 Flow chart for SEM strategy. This procedure involves the production of anti-CREF-Trans 6 polyclonal antibodies, which are used to block rat antigenic epitopes on transfected CREF-Trans 6 prior to injection into animals. The strategy results in the production of immune spleen cells that react with transfected surface-expressed antigens on CREF-Trans 6 cells. Spleen cells are then fused with NS1 murine myeloma cells, producing hybridomas secreting monoclonal antibodies specific for antigens expressed on the cell surface of transfected CREF-Trans 6 cells.
Figure 2:
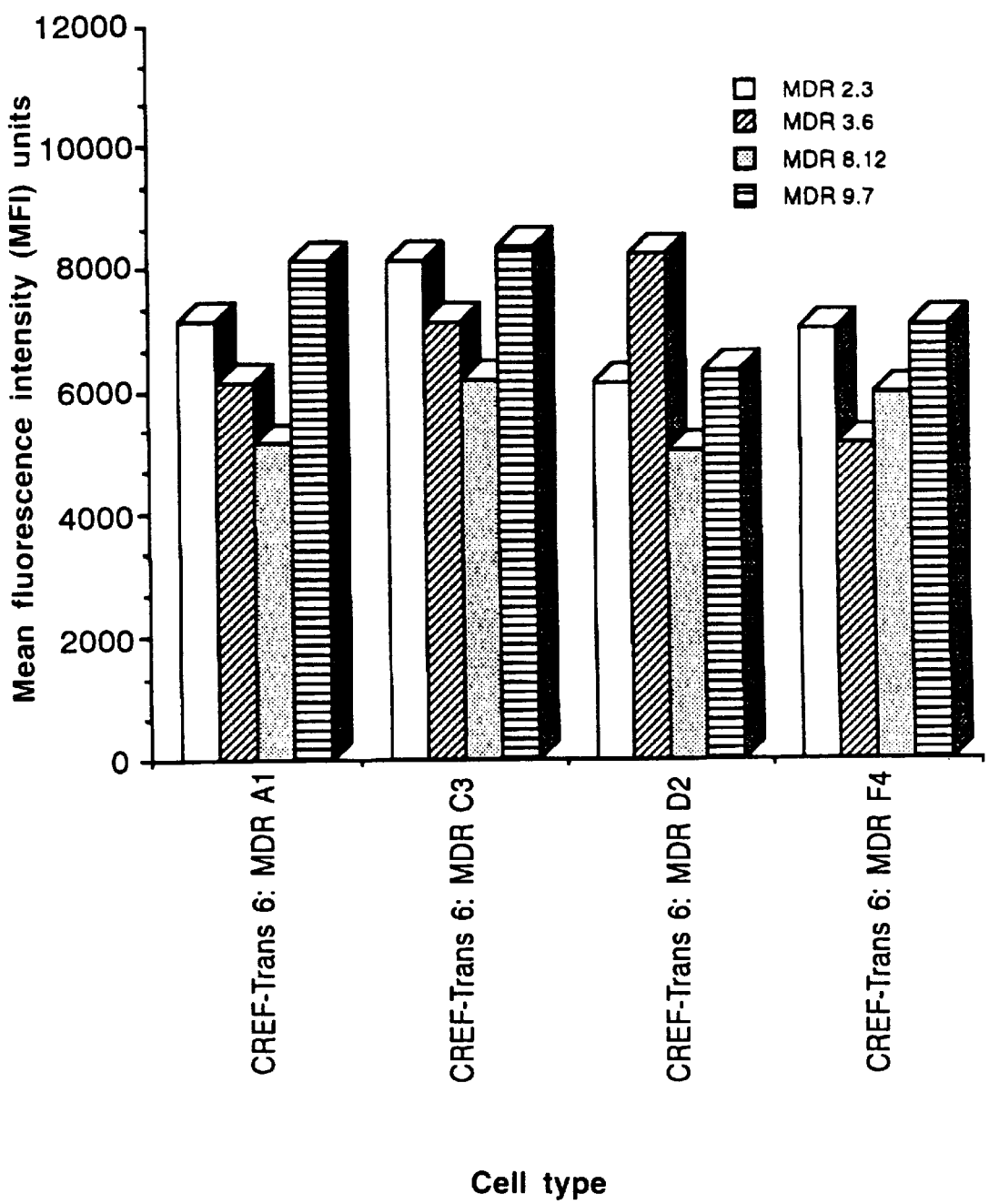
FIG. 2 Reactivity toward MDR CREF-Trans 6 cells subject to SEM produced MDR monoclonal antibodies. CREF-Trans 6 cells were transfected with a human MDR-1 gene and MDR clones resistant to colchicine were isolated. The SEM approach was used to generate independent hybridomas (MDR 2.3, MDR 3.0, MDR 8.12 and MDR 9.7) that secreted monoclonal antibodies reacting with surface epitopes of the MDR transporter expressed in CREF-Trans 6:MDR A1 cells but not untransfected non-MDR CREF-Trans 6 parental cells. The SEM-derived monoclonal antibodies were also tested for reactivity with three independently derived CREF-Trans 6 MDR clones. CREF-Trans 6:MDR C3, CREF-Trans 6:MDR D2 and CREF-Trans 6:MDR F4. Samples were analyzed by FACS, and results are expressed as mean fluorescence intensity units. Replicate samples varied by <10% and replicate studies varied by <20%.

Development of Monoclonal Antibodies Reacting With MDR CREF-Trans 6 and MCF7 cells To determine the feasibility of the SEM approach for developing monoclonal antibodies reactive with cell-surface antigens on transfected target cells, applicants performed initial studies using a defined molecule expressed on the cell surface, i.e., the typical MDR gene product. A schematic of the SEM protocol is shown in FIG. 1. Overexpression of the MDR1 gene results in an increased quantity of the 170-kd membrane glycoprotein (P-glycoprotein), which functions as an adenosine triphosphate-dependent drug efflux pump [reviewed in (23)]. CREF-Trans 6 cells were transfected with the pHaMDR1/A expression vector (14), and clones surviving in colchicine were isolated. CREF-Trans 6:MDR clones produced MDR1 mRNA, expressed the 170-kd P-glycoprotein, and displayed cross-resistance to other chemotherapeutic agents, including vincristine, doxorubicin, and dactinomycin (data not shown). An MDR CREF-Trans 6 clone (i.e., CREF-Trans 6:MDR A1) was used in combination with the SEM procedure to generate monoclonal antibodies specific for the MDR P-glycoprotein. CREF-Trans 6:MDR A1 cells were coated with polyclonal antibody produced against CREF-Trans 6 cells fixed in formalin and injected four times over a 21-day period into BALB/c mice. Spleen cells were isolated and fused with the NS1 murine myeloma cell line, resulting in hybridomas secreting monoclonal antibodies reacting with outer epitopes of the P-glycoprotein on additional independently derived CREF-Trans 6:MDR clones (FIG. 2). The four monoclonal antibodies specific for the P-glycoprotein, MDR 2.3, MDR 3.6, MDR 8.12 and MDR 9.7, reacted with CREF-Trans 6:MDR A1, CREF-Trans 6:MDR C3, CREF-Trans 6:MDR D2, and CREF-Trans 6:MDR F4 cells. In contrast, the different SEM-derived MDR monoclonal antibodies did not react with a large number of non-MDR cells, including CREF-Trans 6, CREF-Trans 6:4 NMT, LNCaP, MCF7, WiDr, LS174T, H0-1, MeWo, NHSF-1 or GBM-18 (data not shown).

Figure 3:
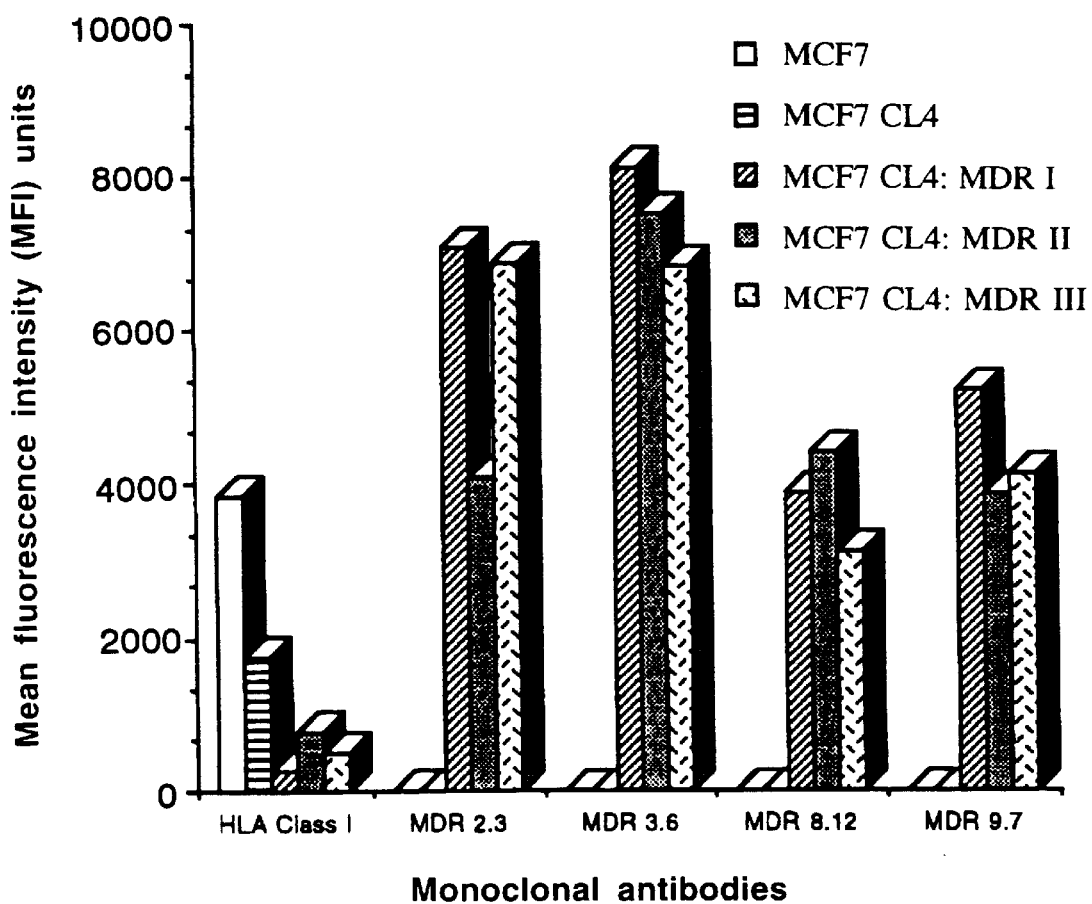
FIG. 3 Reactivity toward MCF7 and MDR MCF7 cells of human leukocyte antigen class 1 monoclonal antibodies and MDR monoclonal antibodies produced using CREF-Trans 6:MDR A1 cells and the SEM procedure. MCF7 and MCF7 CL4 cells are non-MDR cells. MCF7 CL4:MDR I, MCF7 CL4:MDR II, and MCF7 CL4:MDR III are three independent MDR MCF7 CL4 subclones. Fluorescence baseline was determined using irrelevant isotype-matched antibody and goat anti-mouse immunoglobulin G conjugated to fluorescine isothiocyanate. Samples were analyzed by FACS and results are expressed as mean fluorescence intensity units. Replicate samples varied by ≦10% and replicate studies varied by ≦20%.

Applicants then determined if an additional cell type expressing the same MDR1 gene and the MDR phenotype as CREF-Trans 6:MDR A1 cells also contained the same P-glycoprotein surface antigenic epitopes. MDR MCF7 CL4 cells were developed by transfection with pHaMDR1/A and selection for colchicine resistance. MCF7 parental cells and the single-cell-derived MCF7 subclone, MDF7 CL4, did not display the MDR phenotype and did not react with monoclonal antibodies MDR 2.3, MDR 3.6, MDR 8.12, or MDR 9.7 (FIG. 3). However, both MCF7 and MCF7 CL4 cells reacted with human leukocyte antigen class I monoclonal antibodies. A series of independently derived MDR MCF7 CL4 subclones, including MCF7 CL4:MDR I, MCF7 CL4:MDR II and MCF7 CL4:MDR III cells, was found to react with both the human leukocyte antigen class I and SEM-derived MDR monoclonal antibodies (FIG. 3). These results indicate that monoclonal antibodies developed using the SEM approach with transfected CREF-Trans 6 cells can also react with additional cell types expressing the same surface-localized molecules.

Figure 4:
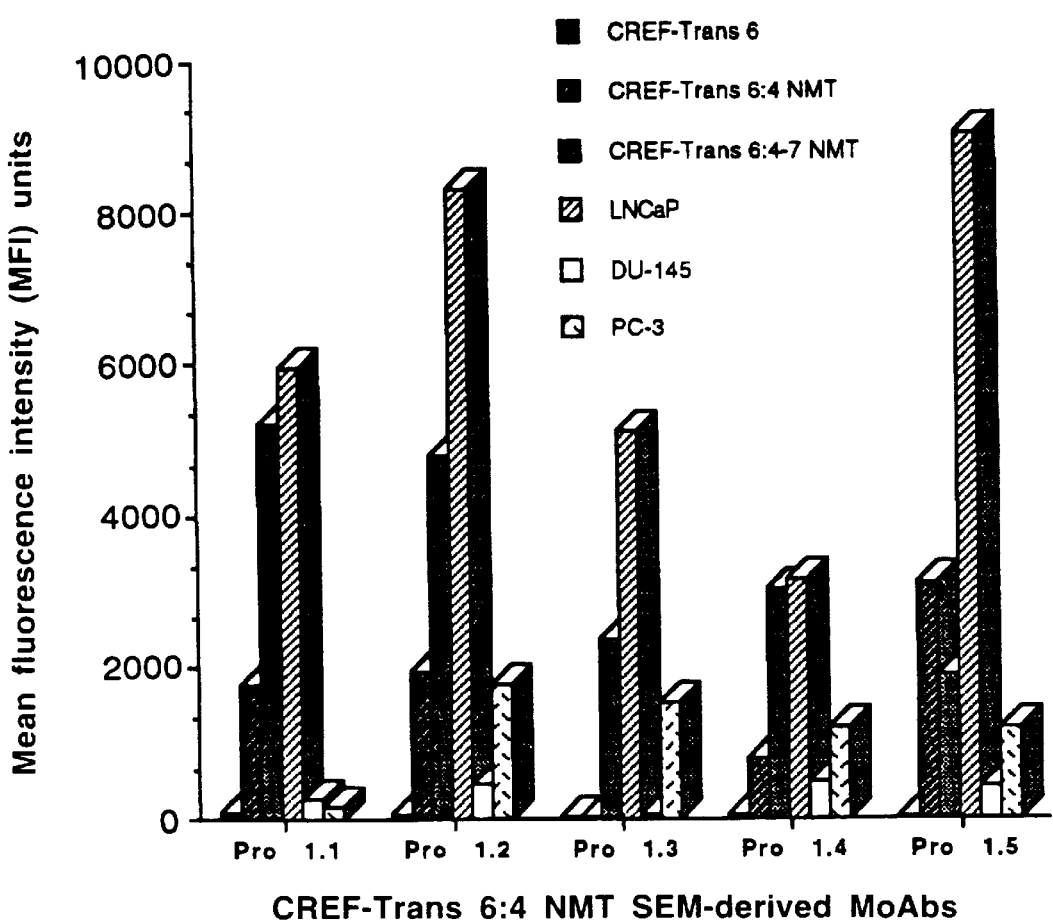
FIG. 4 Reactivity toward untransfected CREF-Trans 6, LNCaP DNA-transfected CREF-Trans 6 and human prostatic carcinoma cell lines of SEM-derived monoclonal antibodies. Pro 1.1, 1.2, 1.3, 1.4 and 1.5 are monoclonal antibodies produced by independent hybridomas generated by fusing spleen cells from mice immunized with LNCaP DNA-transfected, tumor-derived CREF-Trans 6 cells coated with anti-CREF-Trans 6 polyclonal antibodies, CREF-Trans 6:4 NMT, with NS1 murine myeloma cells. The cells analyzed were parental CREF-Trans 6–4 NMT (primary LNCaP DNA-transfected, tumor derived transfectant derived from tumor), CREF-Trans 6:4–7 NMT (secondary CREF-Trans 6:4 NMT DNA-transfected, tumor-derived transfectant derived from tumor), and human prostatic carcinoma cell lines LNCaP, DU-145 and PC-3. Samples were analyzed by FACS, and results are expressed as mean fluorescence intensity units. Replicate samples varied by <10% and replicate studies varied by <15%.

Development of Monoclonal Antibodies Reacting With Human Prostatic Carcinoma Cells Cotransfection of CREF-Trans 6 cells with high-molecular-weight DNA from the human prostatic carcinoma cell line LNCaP and pSV2neo plasmid, followed by selection for G418 resistance and injection into nude mice, results in tumor formation (11). To determine if tumor-derived CREF-Trans 6 cells display novel surface molecules related to the original transforming human tumor DNA, applicants used the SEM procedure with a primary nude mouse tumor-derived cell line, CREF-Trans 6:4 NMT (11). Cells were coated with CREF-Trans 6 polyclonal antibodies, fixed in formalin, and injected repeatedly into BALB/c mice. As described above for MDR CREF-Trans 6 cells, hybridomas were produced, and specific hybridomas were identified that produced monoclonal antibodies reacting with both primary tumor-derived (CREF-Trans 6:4 NMT) and secondary tumor-derived (CREF-Trans 6:4–7 NMT) cells (FIG. 4). These monoclonal antibodies, designated Pro 1.1, Pro 1.2, Pro 1.3, Pro 1.4 and Pro 1.5 did not react by FACS analysis with CREF-Trans 6, NHSF-1, GBM-18, WiDr, LS174T, MeWo, or H0-1 cells (data not shown). All five monoclonal antibodies did, however, react with LNCaP cells, and specific Pro monoclonal antibodies also reacted (as demonstrated by FACS analysis) with two additional human prostatic carcinoma cell lines, PC-3 and DU-145.

The degree of surface binding of the different Pro monoclonal antibodies to the same cell type varied, suggesting that these monoclonal antibodies may recognize different epitopes on the same tumor-associated antigen. With the majority of the Pro monoclonal antibodies, binding was greater with LNCaP cells than with CREF-Trans 6:4 NMT or CREF-Trans 6:4–7 NMT cells. In the case of PC-3 and DU-145 human prostatic carcinoma cells, four (1.2, 1.3, 1.4 and 1.5) of the five Pro monoclonal antibodies bound to PC-3 cells, whereas low-level binding was apparent only with Pro 1.2, 1.4 and 1.5 in DU-145 cells. Preliminary FACS analysis also indicated that Pro 1.1, 1.3 and 1.5 displayed significant binding to the surface of two human breast carcinoma cell lines, T47D and MCF7 (data not shown).

Figure 5:
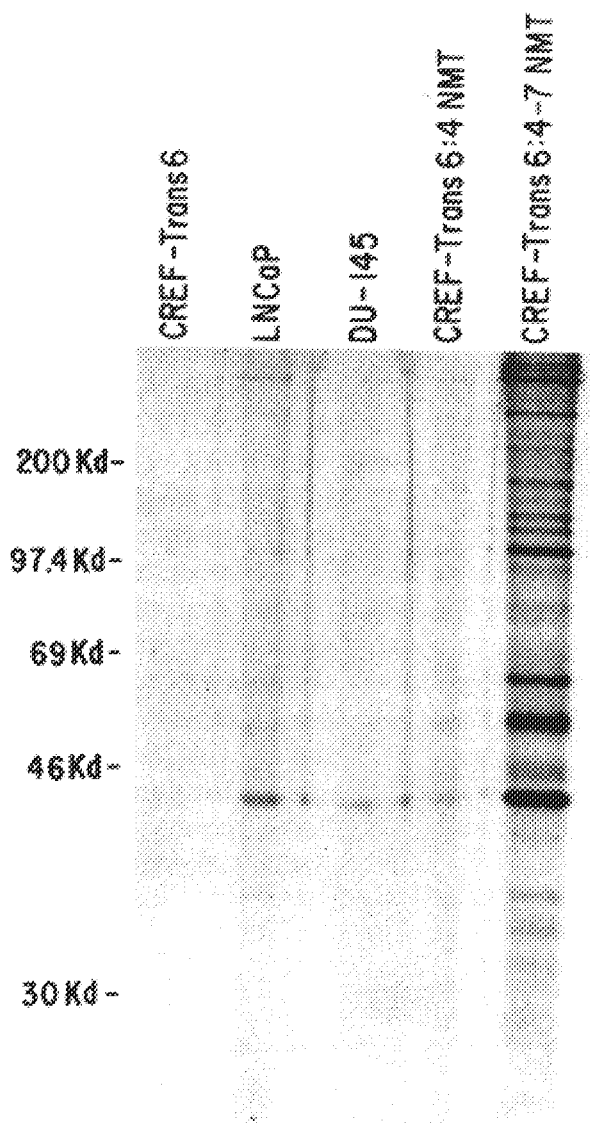
FIG. 5 Expression of putative human prostatic carcinoma encoded polypeptides in LNCaP DNA-transfected tumor-derived CREF-Trans 6 cells and LNCaP and DU-145 human prostatic carcinoma cells. Labeled cell lysates from the cell lines were immunoprecipitated with monoclonal antibody Pro 1.4. Molecular weight size markers are indicated on the left side of the figure. Experimental details can be found in the Materials and Methods section and Duigou et al. (20).

To obtain additional information about the Pro monoclonal antibodies generated using the SEM approach, applicants performed immunoprecipitation analysis of polypeptides encoded by transfected CREF-Trans 6 and human prostatic carcinoma cells (FIG. 5). Cells were labeled with [$^{35}$S] methionine, and cell lysates were prepared and combined with monoclonal antibody Pro-1.4. Immunoprecipitates were analyzed by sodium dodecyl sulfate-polyacrylamide gel electrophoresis (19). A protein of approximately 42 kd was immunoprecipitated from cell lysates produced from CREF-Trans 6:4 NMT, CREF-Trans 6:4–7 NMT, LNCaP, and DU-145 (FIG. 5). In contrast, this potentially new tumor-associated antigen was not detected in cell lysates obtained from CREF-Trans 6, NHSF-1, GBM-18, WiDR, MeWo, or H0-1 cells (FIG. 5 and data not shown). The relative quantity of the immunoprecipitated 42 kd tumor-associated antigen was greatest in CREF Trans 6:4–7 NMT and LNCaP cells which also displayed the highest level of surface binding using monoclonal antibody Pro 1.4 and FACS analysis (FIG. 4). These results indicate that the SEM procedure can be used to generate monoclonal antibodies recognizing surface-expressed human antigens expressed on transfected CREF-Trans 6 cells containing unidentified human transforming genes that encode tumor-associated antigens expressed on the cell surface.

Experimental Discussion

In many classes of neoplastic cells, unique sets of tumor-associated antigens are present that are not expressed or are expressed at lower levels compared with normal cellular counterparts [reviewed in (2–6)]. The classical approach for detecting these molecules is to use intact cells or cell membrane preparations from tumor cell lines or primary tumor samples to generate hybridomas, producing monoclonal antibodies reacting with specific tumor-associated antigens [reviewed in (1–3, 6)]. This approach is laborious and often unsuccessful in generating monoclonal antibodies that display the necessary specificity to permit their use for cancer diagnostics or therapeutics (3,4,6). An alternative strategy, which is dependent upon a functional change induced in a target cell, involves the use of DNA transfection and an approach termed "surface-epitope masking." In the present study, applicants demonstrate the utility of this combined strategy for the generation of monoclonal antibodies specific for a known surface expressed molecule, the P-glycoprotein-mediating MDR, and the product of an unidentified putative human prostatic carcinoma gene. The SEM approach has also been used to produce monoclonal antibodies reacting with the human γ-interferon receptor (Su, Z-z., Pestka, S., Fisher, P. B.: manuscript in preparation) and an unidentified putative human breast carcinoma gene (Yemul, S., Su, Z-z., Leon, J. A., et al: manuscript in preparation) expressed in CREF-Trans 6 cells. All of these results indicate that the combination of transfection and SEM offers a unique opportunity to generate monoclonal antibodies specific for human tumor-associated antigens without prior knowledge of the identity of the gene encoding these products. With appropriate expression vector gene constructs, this strategy can also be used to generate monoclonal antibodies reacting with well-characterized, surface-localized proteins expressed in CREF-Trans 6 cells. This combined approach, at least in principle, should be applicable to any experimental model in which specific changes occur in the expression of surface molecules between a "tester" (a transfected cell expressing a new surface-expressed molecule) and a "driver" (the untransfected parental cell).

The identity and function of the putative tumor-inducing human prostatic carcinoma gene that has been stably transferred from LNCaP cells to CREF-Trans 6 cells are not known. However, CREF-Trans 6:4 NMT cells that contain this potential prostatic carcinoma gene can be used to generate monoclonal antibodies reactive with surface antigens on both LNCaP-transfected cells and human prostatic carcinoma cell lines. This ability suggest a potential causal relationship between expression of the transfected gene and expression of the prostatic carcinoma phenotype.

Prior studies (24,25) have indicated that transformed NIH 3T3 cells transfected with specific human tumor DNAs could be used to generate monoclonal antibodies specific for surface antigens expressed by the original tumor cell line as well as histologically similar tissue types. This approach has been used to generate monoclonal antibodies specific for cell-surface antigens expressed on NIH 3T3 cells transformed by human pancreatic carcinoma (24) and acute myelogenous leukemia (25) DNA. The monoclonal antibodies produced against DNA-transformed NIH 3T3 cells from human pancreatic carcinoma reacted with surface antigens on transfected transformed cells, the original human pancreatic carcinoma cell line, and six additional human pancreatic carcinoma cell lines (24). These monoclonal antibodies did not react with untransfected NIH 3T3 cells or human lymphoblastoid, melanoma, prostatic carcinoma, or normal human skin fibroblast cell lines (24). Results from both studies (24, 25) indicate that the combination of DNA transfection and monoclonal antibody development may prove useful in generating monoclonal antibodies with specificity for cell-surface epitopes displayed by different histologic tumor types. In this respect, the ability of CREF-Trans 6 to identify tumor-inducing genes without biological activity in NIH 3T3 cells indicates that this new human tumor DNA transfection-acceptor cell line may prove useful for the identification and cloning of potentially novel genetic elements mediating specific human cancers.

In the present study, the SEM approach was used to stimulate the production of spleen cells reactive with cell-surface-accessible molecules. Spleen cells were then used to produce hybridomas that secrete monoclonal antibodies reactive with accessible surface antigens.

The SEM approach described in this manuscript uses a formalin fixation step prior to immunizing animals with polyclonal antibody-coated tester cells. This procedure was originally adopted to more efficiently produce monoclonal antibodies that would have direct diagnostic potential, i.e., they could be used to detect antigens on formalin-fixed tissue. Monoclonal antibodies produced using the SEM procedure have demonstrated specificity for viable cells, frozen tissue specimens, and both formalin-fixed tissue specimens and formalin-fixed cells. The SEM procedure described in this application would not be predicted to generate monoclonal antibodies reactive with fixative-sensitive antigens. However, modifications of the SEM approach using procedures other than formalin fixation, including injection of unfixed antibody-coated cells or use of novel immune complexes (26), should result in the generation of monoclonal antibodies reacting with fixative sensitive antigenic epitopes of molecules expressed on the cell surface.

Recently, an approach called "phage display combinatorial libraries" has been developed in which combinatorial complementary DNA (cDNA) libraries are prepared in phage directly from antigen-stimulated spleen cells (27,28).

In this context, transfected cells that had been subject to the SEM procedure could be utilized as immunogens to stimulate an antigenic response that could then be followed by the isolation of spleen cells and generation of combinatorial phage cDNA libraries. This approach could then result in the direct identification of potentially critical genes involved with transformation and with genes that encode specific human tumor-associated antigens and other molecules expressed on the cell surface.

The SEM approach has been performed using murine monoclonal antibodies to coat rat antigenic surface epitopes on a rat embryo fibroblast cell line, CREF-Trans 6. Alternatively, it should be possible to use transfected CREF-Trans 6 cells as direct immunogens in syngeneic Fischer rats for the generation of rat hybridomas or rat x mouse heteromyelomas. Although these studies are still in progress, it is apparent that the SEM approach employing murine monoclonal antibody-coated CREF-Trans 6 is preferable to injection of transfected CREF-Trans 6 cells directly into syngeneic rats. Murine monoclonal antibodies are relatively easy to produce and are highly amenable to purification in large quantities. In addition, the technologies required for the genetic manipulation of murine monoclonal antibodies (e.g., chimerization, humanization, and bispecific monoclonal antibodies) are readily available (29–31). These genetic approaches are extremely important if a monoclonal antibody is to be used in human clinical trials for imaging or as a therapeutic agent (4–6).

The theoretical basis of the SEM approach involves antigenic subtraction, i.e., the blocking of antigenic sites shared by two genetically similar cell types. This process results in an increase in the sensitivity of detection of novel surface antigens. The present studies have emphasized applications of the SEM approach, using transfected cells expressing known as well as unidentified cell-surface molecules. However, many additional situations that would be adaptable to the SEM procedure can be envisioned. For example, the SEM protocol could be used to develop monoclonal antibodies specific for surface changes occurring in metastatic tumor cells. To achieve this goal, polyclonal antibodies could be generated against a primary tumor, and these polyclonal antibodies could be used to mask surface epitopes on metastatic tumors. This step would be performed prior to sensitizing animals for the development of hybridomas or combinatorial phage cDNA expression libraries specific for surface-expressed metastatic antigens. Similarly, polyclonal antibodies could be generated against normal tissue of a specific histologic type, and these polyclonal antibodies could then be used to mask surface epitopes on a histologically similar tumor derived from the same patient. The cells with masked surface epitopes could then be injected into animals so that they would develop sensitized spleen cells for the development of hybridomas or combinatorial phage cDNA libraries specific for tumor-associated antigens. SEM would also appear to be ideally suited for the development of monclonal antibodies specific for the outer domain of membrane-localized growth factor receptors and cell-membrane transporter proteins. Future applications of the SEM approach could also result in the development of monoclonal antibodies and/or the isolation of relevant genes involved in determining tumor cell recognition by both nonspecific and specific immunologic effector cells, mediating atypical multidrug resistance, and identifying mediators of autoimmune diseases.

References of the First Series of Experiments

1. Goding, J. W., (1980) Antibody production by hybridomas, *J. Immunol. Methods*, 39:285–308.
2. Schlom, J., Colcher, D., Hand, P. H., et al. (1985) Monoclonal antibodies reactive with breast tumor-associated antigens, *Adv. Cancer Res.* 43:143–173.
3. Epstein, A. L., Khawli, L. A., (1991) Tumor biology and monoclonal antibodies: overview of basic principles and clinical considerations, *Antibody Immunoconjugates Radiopharmaceuticals*, 4:373–384.
4. Waldmann, T. A., (1991) Monoclonal antibodies in diagnosis and therapy, *Science*, 252:1657–1662.
5. Pirofski, L. A., Casadevall, A., Scharff, M. D., (1992) Current state of hybridoma technology, *Am. Soc. Microbiol. News*, 58:613–617.
6. Leon, J. A., Goldstein, N. I., Fisher, P. B., New approaches for the development and application of monoclonal antibodies for the diagnosis and therapy of human cancer. *Pharmacol Therapeut.*, in press.
7. Varmus, H., (1984) The molecular genetics of cellular oncogenes, *Annu. Rev. Genet.*, 18:533–612.
8. Weinberg, R. A., (1984) The action of oncogenes in the cytoplasm and the nucleus, *Science*, 230:770–776.
9. Bishop, M. J., (1987) The molecular genetics of cancer, *Science*, 235:305–311.
10. Barbacid, M., (1987) Ras genes, *Annu. Rev. Biochem.*, 56:779–827.
11. Su, Z-z., Olsson, C. A., Zimmer, S. G., et al. (1992) Transfer of a dominant-acting tumor-inducing oncogene form human prostatic carcinoma cells to cloned rat embryo fibroblast cells by DNA-transfection, *Anticancer Res.* 12:297–304.
12. Fisher, P. B., Babiss, L. E., Weinstein, I. B., et al. (1982) Analysis of type 5 adenovirus transformation with a cloned rat embryo cell line (CREF), *Proc. Natl. Acad. Sci., USA*, 79:3527–3531.
13. Horoszewicz, J. S., Leong, S. S., Kawinski, E., et al. (1983) LNCaP model of human prostatic carcinoma, *Cancer Res.*, 43:1809–1818.
14. Kane, S. E., Troen, B. R., Gal, S., et al. (1988) Use of a cloned multidrug resistance gen for coamplification and overproduction of major excreted protein, a transformation-regulated secreted acid protease, *Mol. Cell Biol.*, 8:3316–3321.
15. Reddy, P. G., Graham, G. M., Datta, S., et al. (1991) Effect of recombinant fibroblast interferon and recombinant immune interferon on growth and the antigenic phenotype of multidrug-resistant human glioblastoma multiforme cells, *J. Natl. Cancer Inst.* 83:1307–1315.
16. Vita, J. R., Edwalds, G. M., Gorey, T., et al. (1988) Enhanced in vitro growth suppression of human glioblastoma cultures treated with the combination of recombinant fibroblast and immune interferons, *Anticancer Res.*, 8:297–302.
17. Su, Z-z., Grunberger, D., Fisher, P. B., (1991) Suppression of adenovirus type 5 ElA-mediated transformation and expression of the transformed phenotype by caffeic acid phenethyl ester (CAPE), *Mol. Carcinog.*, 4:231–242.
18. Giovanella, B. C., Stehlin, J. S., Jr., Santamaria, C., et al. (1976) Human neoplastic and normal cells in tissue culture: I. Cell lines derived from malignant melanomas and normal melanocytes, *J. Natl. Cancer Inst.*, 56:1131–1142.
19. Goldstein, N. L., Nagle, R., Villar, H., et al. (1990) Isolation and characterization of a human monoclonal antibody which reacts with breast and colorectal carcinoma, *Anticancer Res.*, 10:1491–1500.
20. Duigou, G. J., Su, Z-z., Babiss, L. E., et al. (1991) Analysis of viral and cellular gene expression during progression and suppression of the transformed phenotype in type 5 adenovirus-transformed rat embryo cells, *Oncogene*, 6:1813–1824.
21. Guarini, L., Temponi, M., Edwalds, G. M., et al. (1989) In vitro differentiation and antigenic changes in human melanoma cell lines, *Cancer Immunol. Immunother.*, 30:262–268.
22. Leon, J. A., Mesa-Tejada, R., Gutierrez, M. C., et al. (1989) Increased surface expression and shedding of tumor associated antigens by human breast carcinoma cells treated with recombinant human interferons or phorbol ester tumor promoters, *Anticancer Res.*, 9:1639–1647.
23. Gottesman, M. M., Pastan, I, (1993) Biochemistry of multidrug resistance mediated by the multidrug transporter, *Annu. Rev. Biochem.*, 62:385–427.
24. Hollingsworth, M. A., Rebellato, L. M., Moore, J. W. et al. (1986) Antigens expressed on NIH 3T3 cells following transformation with DNA from a human pancreatic tumor, *Cancer Res.*, 46:2482–2487.
25. Scuderi, P., Westin, E., Clagett, J., et al. (1985) Detection of surface antigen in N1H 3T3 cells transfected with a human leukemia oncogene, *Med. Oncol. Tumor Pharmacother.*, 2:233–242.
26. Songsakphisarn, R., Goldstein, N. I., (1993) The use of a novel immune complex to isolate neutralizing antibodies to basic fibroblast growth factor, *Hybridoma*, 12:343–348.
27. Marks, J. D., Hoogenboom, H. K., Bonnert, T. P., et al. (1991) By-passing immunization: human antibodies from V-gene libraries displayed on phage, *J. Mol. Biol.* 222:581–597.
28. Huse, W. D., Sastry, L., Iverson, S. A., et al. (1989) Generation of a large combinational library of the immunoglobulin repertoire in phage lambda, *Science*, 249:1275–1281.
29. Tan, L. K., Or, V. T., Morrison, S. L., (1985) A human-mouse chimeric immunoglobulin gene with a human variable region is expressed in mouse myeloma cells, *J. Immunol.*, 135:3564–3567.
30. Co, M. S., Deschamps, M., Whitley, R. J., et al. (1991) Humanized antibodies for antiviral therapy, *Proc. Natl. Acad. Sci, USA*, 88:2869–2873.
31. Staerz, U. D., Bevan, M. J., (1986) Hybrid hybridoma producing a bispecific monoclonal antibody that can focus effector T-cell activity, *Proc. Natl. Acad. Sci, USA*, 83:1453–1457.

Second Series of Experiments

Elucidating the relevant genomic changes mediating development and evolution of prostate cancer is paramount for effective diagnosis and therapy. Using an improved DNA-acceptor cell line, CREF-Trans 6, and cotransfection techniques, with human prostatic carcinoma DNA, a putative dominant-acting nude mouse tumor-inducing oncogene, PTI-1, has been identified and cloned. Differential RNA display reveals a novel 214 bp DNA fragment representing a differentially expressed RNA in tumor-derived transfected cells. Screening of a human prostatic carcinoma (LNCaP) cDNA library with the novel 214 bp DNA sequence identifies a full-length 2.0 Kb PTI-1 cDNA. Sequence analysis indicates that PTI-1 is a novel gene containing a unique 630 bp 5' sequence and a 3' sequence homologous to a truncated and mutated form of human elongation factor-1 alpha. In vitro translation demonstrate that the PTI-1 cDNA encodes a predominant ~46 kDa protein. Probing Northern blots with a DNA fragment corresponding to the 5' region of the PTI-1 gene identifies multiple PTI-1 transcripts in RNAs from LNCaP-transfected tumor-derived CREF-Trans 6 cells and human carcinoma cell lines derived from the prostate, lung, breast and colon. In contrast, PTI-1 RNA is not present in human melanoma, neuroblastoma, osteosarcoma, normal cerebellum or glioblastoma multiforme cell lines. Using a pair of primers recognizing a 279 bp region within the unique 630 bp 5' PTI-1 sequence, RT-PCR detects PTI-1 expression in patient-derived prostate carcinomas, but not in normal prostate or benign prostatic hypertrophy (BPH) . In contrast, RT-PCR detects prostate-specific antigen (PSA) expression in all prostate tissue specimens. These results indicate that PTI-1 is a novel putative oncogene that may contribute to carcinoma development in human prostate and other tissues. The approaches used, rapid expression cloning with the CREF-Trans 6 system and the differential RNA display strategy, should prove widely applicable for identifying and cloning additional novel human oncogenes.

The American Cancer Society estimates that 200,000 American men will have been diagnosed with prostate cancer in 1994 and 38,000 afflicted men will have died of this disease (1). The current methods for detecting early prostate cancer are limited in both their sensitivity and specificity (2). These include physical examination that might easily miss small or centrally located tumors, serum prostate-specific antigen (PSA) determination that is not specific to malignant prostate disease, and tissue biopsy in which sampling error may lead to erroneous benign diagnosis (3,4). Predictors and early detection of therapeutic relapse such as monitoring of PSA levels, ultrasound and bone scans are also unsatisfactory, as these require fairly bulky tumor regrowth before discovery (5,6). Using current approaches a high percentage, 40 to 50%, of patients considered to have clinically localized disease actually contain understaged diseases subsequent to radical surgery (7,8). Surgical intervention is not considered the appropriate treatment protocol for patients with progressive disease. These findings emphasize the need for improved diagnostic and therapeutic approaches for identifying prostate carcinomas and for predicting clinical aggressiveness.

A primary objective of investigators studying cancer etiology is the identification of gene(s) within tumor cells with oncogenic potential. A procedure to achieve this goal involves the transfer of high molecular weight (HMW) DNA from established tumor cell lines or primary tumors into appropriate acceptor cell lines by DNA-transfection (9). Target cells are then examined for morphological transformation, i.e., focus formation. A modification of this approach involves cotransfection of target cells with HMW DNA plus a selectable antibiotic resistance gene, such as pSV2neo, selection for antibiotic resistance and then injection of pooled antibiotic resistant cells into nude mice to identify clones of cells with tumorigenic potential (10). The majority of studies using these approaches have relied on the immortal murine cell line NIH-3T3 (9,10). Unfortunately, NIH-3T3 cells generally prove unsuccessful in identifying novel dominant-acting oncogenes from human tumor cell lines or clinical samples and even when successful, subsequent cloning indicates genetic elements not relevant to the majority of human cancers. These studies accentuate the need for better techniques to identify dominant-acting human cancer genes and for more suitable target cell lines to detect novel tumor-inducing oncogenes.

Recent studies using the cotransfection/nude mouse tumor assay with HMW DNA from a human prostatic carcinoma cell line, LNCaP (11), and a new DNA-acceptor cell line, CREF-Trans 6 (12), indicate the presence of a dominant-acting tumor-inducing gene (12). Applicants have presently cloned and characterized a novel gene, prostate carcinoma tumor inducing gene 1 (PTI-1), using the differential RNA display (DD) technology (13), library screening strategies (14,15) and the RACE procedure (14). The full-length PTI-1 cDNA consists of 2,123 nucleotides and contains a novel 630 nt region sharing sequence homology with bacterial ribosomal 23S RNA fused to a sequence that is a truncated and mutated form of human elongation factor-1 alpha (EF-1α). LNCaP-transfected tumor-derived CREF-Trans 6 cells as well as human prostate carcinoma cell lines and patient-derived prostate carcinomas express PTI-1. In contrast, PTI-1 RNA is not evident using RT-PCR in normal prostate or benign prostatic hypertrophy (BPH) tissue samples. PTI-1 expression occurs in additional human carcinomas, including breast, colon and lung, but not in normal cerebellum, glioblastoma multiforme, melanoma, neuroblastoma or osteosarcoma cell lines. These observations indicate that PTI-1 is a novel genetic element displaying expression in specific human carcinomas and implicates mutagenic changes in EF-1α as a contributor to the carcinogenic process.

Materials and methods

Cell lines. The LNCaP cell line was derived from metastatic deposits from a patient with advanced prostate cancer (11) and was provided by Dr. Steven Harris (W. Alton Jones Cell Science Center, N.Y.) . CREF-Trans 6 and LNCaP DNA-transfected nude mouse tumor-derived CREF-Trans 6 cells, CREF-Trans 6:4 NMT, were isolated as described previously (12). The hormone independent prostatic carcinoma cell line DU-145, the endometrial carcinoma cell line HTB-113, the small cell lung carcinoma cell line NCI-H69 and the human neuroblastoma cell line IMR-32 were obtained from the American Type Culture Collection. The nasopharyngeal carcinoma cell line KB 3–1 was provided by Dr. Michael M. Gottesman (NCI, Md.). The human breast carcinoma cell line MCF 7 and the human colon carcinoma cell lines WiDr, HT 29, SW480 and LS174T were supplied by Dr. John W, Greiner (NCI, Md.). The human breast carcinoma cell line T47D was provided by Dr. Ricardo Mesa-Tejada (MetPath Inc., N.J.). A normal human cerebellum cell line, a human glioblastoma multiforme cell line GBM-18 and a human neuroblastoma cell line NB-11 were established in the applicants' laboratory (17–19). H0-1 human melanoma cells were obtained from Dr. Beppino Giovanella (Stehlin Foundation, Tex.). C8161 metastatic human melanoma cells were supplied by Dr. Danny R. Welch (Hershey Medical Center, Pa.) . The human osteosarcoma cell line Saos-2 was provided by Dr. C. S. Hamish Young (Columbia Univ., N.Y.). Conditions for growing the various cell types were as described previously (11,12, 17–19).

RNA preparation, differential RNA display (DD) and RT-PCR. Total cytoplasmic RNA was isolated from logarithmically growing cell cultures as previously described (14,15). Tissue samples from normal prostates and patients with prostatic carcinomas or BPH were frozen in liquid nitrogen and RNA was isolated using the TRIzol reagent as described by GibcoBRL (Md.). Tissue samples were supplied by the Cooperative Human Tumor Network (CHTN). Samples of normal prostate were obtained from autopsies of males <40 years of age. All tissues were histologically confirmed as normal, BPH or carcinoma of the prostate. The DD procedure was performed essentially as described by Liang and Pardee (13). Two $\mu$g of mRNAs from CREF-Trans 6 and CREF-Trans 6:4 NMT cells were reverse transcribed with 300 units of MMLV reverse transcriptase (BRL) in the presence of 2.5 $\mu$M of primer T12GC (5'-TTTTTTTTTTTTGC-3') (SEQ. ID NO.8) and 20 $\mu$M dNTP mix (BRL) for 60 min at 35° C. Two $\mu$g of the cDNA was PCR-amplified in the presence of 2 $\mu$M T12GC and 2 $\mu$M of a 5'-primer JB-24 (5'-ACCGACGTCGACTATCCATGAACA-5') (SEQ. ID NO.9). Samples were resolved in parallel lanes on a 5% denaturing sequencing gel and differentially expressed bands were removed from the gel and electroeluted in 0.2x TBE solution. The same pair of primers were used for PCR amplification of the differentially expressed sequences followed by TA cloning kit (Invitrogen). Plasmids containing inserts of the predicted size were sequenced by the Sanger method (Sequenase kit, version 2.0, USB) or the inserts were isolated and used to probe Northern blots (14–16). RT-PCR using appropriate primers was performed as described previously (16).

cDNA library construction, screening and sequencing. A cDNA library of LNCaP mRNA was constructed in the Uni-ZAP XR vector (Stratagene) and screened as previously described (14). A 1.8 kb PTI-1 DNA fragment was obtained by RT/PCR amplification of LNCaP cDNA with a 20 mer (5'-AACTAAGTGGAGGACCGAAC-3') (SEQ. ID NO.10) within the 214 bp DNA obtained by DD. Inserts from the plasmids containing the largest PTI-1 inserts were excised by digestion with the restriction enzymes XhoI and EcoRI and tested by Northern blotting with appropriate RNA samples and sequenced using the Sanger method with an Applied Biosystems (Model 373A, Version 1.2.1) sequencer and oligonucleotides synthesized from both ends of the gene inserts.

RACE procedure. To identify the 5'-extended region of PTI-1, a 22 base oligomer (I) (5'-CCTTGCATATTAACATAACTCG-3') (SEQ. ID NO.11) and a 19 base oligomer (II) (5'-AAGTCGCCCTATTCAGACT-3'), (SEQ. ID NO.12) antisense direction of the sequences 262–283 bp and 317–336 bp, respectively, were synthesized. The RACE protocol was performed using the 5' RACE system (GibcoBRL, Md.) as previously described (14).

In vitro translation of PTI-1 encoded proteins. PTI-1 was linearized by digestion with XhoI and used as a template to synthesize mRNA using the mCAP mRNA capping kit (Stratagene). In vitro translation of PTI-1 was performed using a rabbit reticulocyte lysate translation kit with conditions as described by GibcoBRL (Md.).

Experimental Results

Figure 6:
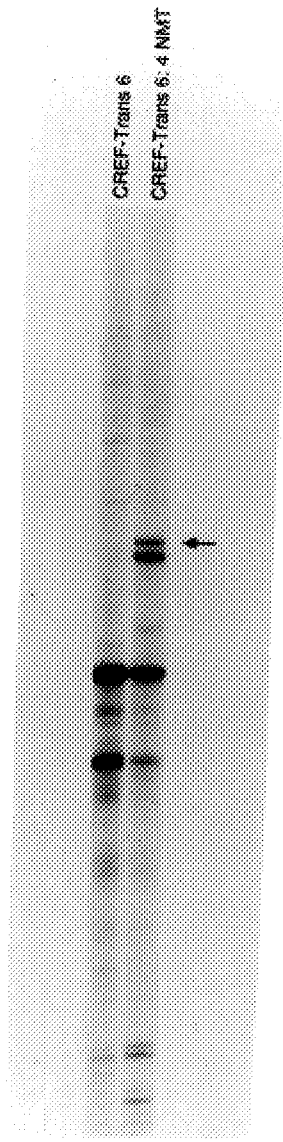
FIG. 6 Differential display (DD) of CREF-Trans 6 and CREF-Trans 6:4 NMT mRNAs. DD was performed with a 24 oligomer (5'-) and a 14 oligomer (3'-) with sequences shown in materials and methods. The arrow indicates the PTI-1 band appearing only in mRNA from CREF-Trans 6:4 NMT, but not in CREF-Trans 6 cells. The length of this PTI-1 DNA fragment is 214 bp.
Figure 7:
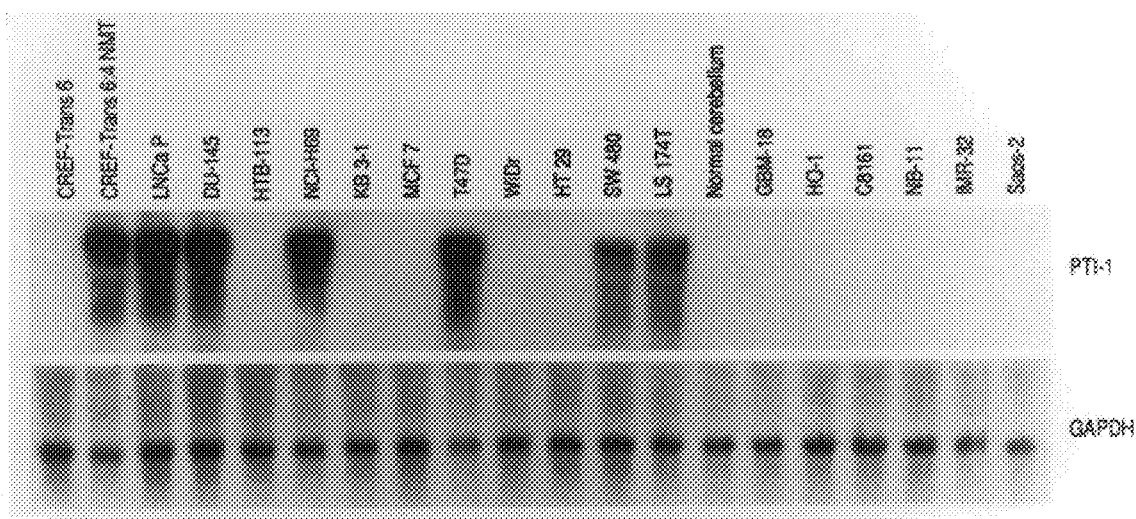
FIG. 7 Expression of PTI-1 in normal and tumor cell lines. RNAs from CREF-Trans 6, CREF-Trans 6:4 NMT and various normal and tumor-derived human cell lines were transferred to nylon membranes and probed with a [$^{32}$P]-labeled 279 bp PTI-1 DNA fragment (317 to 596 bp, between primers A and L, FIGS. 8A–8B. Membranes were stripped and reprobed with a [$^{32}$P]-labeled GAPDH gene.

Identification and properties of PTI-1. The rapid expression cloning system identified a potential oncogenic element in LNCaP cells (12). To identify genes displaying differential expression in CREF-Trans 6 cells and nude mouse tumor-derived LNCaP-transfected CREF-Trans 6 cells, CREF-Trans 6:4 NMT, the DD approach developed by Liang and Pardee (13) was used. This protocol permits identification of differentially expressed cDNAs based on size as opposed to nucleotide composition or function. A problem often encountered using DD is the identification of amplified sequences not displaying differential expression when tested using appropriate RNA samples and Northern blotting (12). An example of this type of artifact is seen in FIG. 6, i.e., the band present in CREF-Trans 6:4 NMT directly below the arrow. The frequency of false signals can be significantly reduced by using subtraction hybridization prior to PCR amplification and DD (data not shown). Using DD, a 214 bp DNA fragment (PTI-1) was identified in the LNCaP-transfected nude mouse tumor-derived CREF-Trans 6 cell line, CREF-Trans 6:4 NMT, that was not present in parental CREF-Trans 6 cells (FIG. 6, arrow). The PTI-1 fragment was isolated, cloned, sequenced and used to probe Northern blots containing RNAs from CREF-Trans 6, CREF-Trans 6:4 NMT and LNCaP cells (FIG. 7). The 214 bp PTI-1 DNA fragment is a novel sequence and hybridizes to several RNAs present in CREF-Trans 6:4 NMT, LNCaP and the hormone independent prostate carcinoma cell line DU-145 (FIG. 7).

The complete sequence of PTI-1 is presented in FIGS. 8A–8B. PTI-1 consists of 2,123 bp, the 5'-flanking region (1 to 215 bp) was obtained by RACE 5'-extension and the remainder of the gene (216 to 2,123 bp) was determined by direct sequencing. Primer extension analysis and RT-PCR of LNCaP mRNA confirm that PTI-1 is a full-length cDNA (data not shown). The 3' region of PTI-1 extending from 630 to 2,123 bp displays 97% homology to a truncated human EF-1α gene. The 5' region of PTI-1 displays no homology to eucaryotic genes, but instead is ~85% homologous to procaryotic 23S ribosomal RNA gene from *Mycoplasma hyopneumoniae*. This region of PTI-1 contains the 214 bp DNA marker (core) sequence obtained using DD (FIG. 6). The unique 5' region also contains a large number of stop codons (TAA, TGA and TAG sequences) FIGS. 8A–8B. These observations suggest that PTI-1 is a fusion gene consisting of two regions: a 5' unique 630 bp region and a 3' truncated and mutated EF-1α gene.

PTI-1 contains an open-reading frame from bp 621 to 1,814 with a stop codon after the last amino acid K and encodes a protein of 398 aa (FIGS. 8A–8B). A comparison of the amino acid sequence of PTI-1 (1 to 398 aa) and a partial human EF-1α (aa 1 to 462) is presented in FIG. 8C. PTI-1 and the truncated human EF-1α share 98.4% similarity and 97.7% identity. PTI-1 contains the same carboxyl terminus as human EF-1α. The N-terminus of PTI-1 is different from human EF-1α and consists of a deletion of 67 aa normally found in human EF-1α and an insertion of 3 unique amino acids (MQS) in PTI-1 that differs from the original N-terminus (MGK) of human EF-1α. In addition, 6 in frame amino acid changes are present in PTI-1 (FIG. 8C.) The loss of 67 amino acids in the N-terminus plus changes in specific amino acids, from positive charged to non-positive charged amino acids and from hydroxyl group-containing to non-hydroxyl group-containing amino acids, can be anticipated to impact on the three dimensional structure and functionality of this mutant EF-1α protein.

Figure 9:
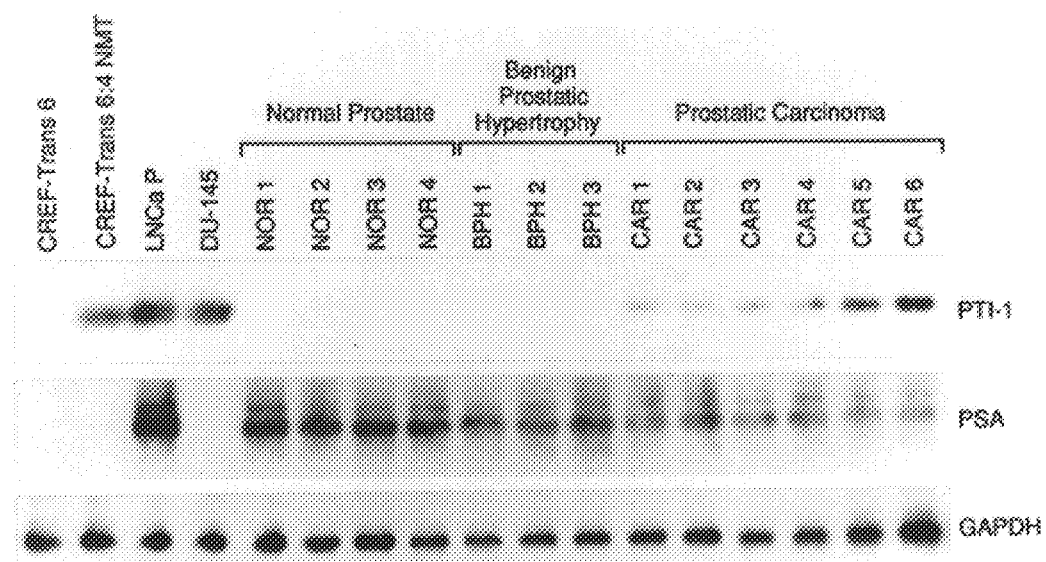
FIG. 9 RT-PCR analysis of PTI-1, PSA and GAPDH expression in cell lines and tissue samples of normal prostate, BPH and prostate carcinoma. RT-PCR of PTI-1 uses two primers consisting of a pair of 20-oligomers: primer L with the sequences 5'-GAGTCTGAATAGGGCGACTT-3' (SEQ. ID NO.1) (sense orientation); and primer A with the sequence 5'-AGTCAGTACAGCTAGATGCC-3' (SEQ. ID NO.2)

On the basis of sequence analysis, PTI-1 should encode a protein of 43.8 kDa. To confirm this prediction, in vitro translation analyses of proteins encoded by the PTI-1 cDNA were determined (FIG. 9). A predominant protein present after in vitro translation of PTI-1 has an $M_r$ of ~46 kDa. This value is larger than predicted and may result because of protein modification, i.e., phosphorylation, in the rabbit reticulocyte lysate system. Four additional minor proteins ($M_r$41 to 30.5 kDa) are also present after in vitro translation. These proteins probably result from initiation of protein synthesis at start codons (ATG) downstream of the first start codon in PTI-1 (FIGS. 8A–8B).

Expression of PTI-1 in RNA samples from patient-derived tissues and cell lines. An important question is whether PTI-1 expression occurs in prostatic carcinomas in vivo. For this analysis, RNA was isolated from quick-frozen prostate samples from patients obtained during operations and confirmed as prostatic carcinomas or BPH histologically. RNAs were also extracted from normal prostates obtained at autopsy from men less than 40 years of age and histologically normal. Using RT-PCR with primers (A and L) (FIGS. 8A–8B) synthesized from the unique 630 bp 5' PTI-1 sequence, expression is apparent in seven of eight human prostatic carcinomas (FIG. 10 and data not shown). In contrast, PTI-1 is not expressed in four normal prostates or three BPH patient samples (FIG. 10). In contrast, LNCaP and all prostate samples, including normal, BPH and carcinoma, are positive for PSA expression, whereas CREF-Trans 6, CREF-Trans 6:4 NMT and DU-145 do not express PSA (FIG. 10). All samples were positive for GAPDH expression (FIG. 10). These results indicate that PTI-1 is expressed in human prostate carcinomas, but not in normal prostates or BPH.

To determine the pattern of PTI-1 expression in additional cell types, RNAs from various cell lines were analyzed by Northern blotting using PTI-1 and GAPDH as probes (FIG. 7). In addition to being expressed in CREF-Trans 6:4 NMT, LNCaP and DU-145, PTI-1 expression is evident in other human carcinomas, including NCI-H69 (small cell lung), T47D (breast), and SW480 and LS174T (colon). In contrast, PTI-1 expression is not detected in HTB-113 (endometrial adenocarcinoma), KB 3–1 (nasopharyngeal carcinoma), MCF 7 (breast carcinoma), WiDr and HT 29 (colon carcinoma), normal cerebellum, GBM-18 (glioblastoma multiforme), H0-1 and C8161 (melanoma), NB-11 and IMR-32 (neuroblastoma) or Saos-2 (osteosarcoma) cells. These observations indicate that PTI-1 expression is not restricted to human prostate carcinoma, but also occurs in ~50% of the human carcinomas analyzed.

Experimental Discussion

Cancer is a progressive disease in which tumor cells manifest continuous genetic changes that correlate with increasing frequencies of chromosomal abnormalities and mutations (rev. 20–22). Recent studies suggest that mutations in genes involved in maintaining genomic stability, including DNA repair, mismatch repair, DNA replication and chromosomal segregation, may result in acquisition of a mutator phenotype by cancer cells predisposing them to further mutations resulting in tumor progression (rev. 21). In leukemias as well as specific solid tumors, improved cytogenetic techniques and molecular approaches indicate that specific translocations result in the activation of proto-oncogene products and the creation of tumor-specific fusion proteins (22). A common observation is that both types of novel oncogenic elements are often transcription factors suggesting that alterations in transcriptional control may directly contribute to cancer development and evolution (22,23). Modifications in the translational machinery of cells, including changes in both eucaryotic initiation factors and elongation factors, can also result in susceptibility to transformation and the acquisition of transformed and oncogenic properties in specific target cells (rev. 24,25). For example, overexpression of a normally rate-limiting protein initiation factor, eIF-4E, can cooperate with both the v-myc and adenovirus E1A gene in inducing transformation of primary rodent fibroblasts (26), induce tumorigenic transformation in both NIH 3T3 and Rat 2 cells (27) and induce in combination with Max both a tumorigenic and metastatic phenotype in Chinese hamster ovary (CHO) cells (28). Enhanced expression of elongation factor-1$a$ (EF-1$\alpha$), a nucleotide exchange protein that binds GTP and aminoacyl-tRNA and results in codon-dependent placement of this aminoacyl-tRNA at the A site of the ribosome (24,25), confers susceptibility to carcinogen- and ultraviolet light-induced transformation to mouse and Syrian hamster cell lines (29). Elevated levels of wild-type EF-1$\alpha$ also occur in tumors of the pancreas, colon, breast, lung and stomach relative to normal tissue (30). Moreover, enhanced expression of EF-1$\gamma$, a nucleotide exchange protein that mediates transport of aminoacyl tRNAs to 80S ribosomes during RNA translation, is found in a high proportion of pancreatic tumors (78%), colorectal tumors (86%) and colorectal adenomas (56%) relative to normal-appearing adjacent tissue (31–33). These findings indicate that alterations in both gene transcription and protein synthetic processes contribute to oncogenesis.

The present study implicates a novel gene, PTI-1, that contains a unique sequence linked to a truncated and mutated EF-1$\alpha$ gene, in oncogenic transformation and prostate carcinoma development. PTI-1 is expressed in LNCaP-transfected tumor-derived CREF-Trans 6 cells, human prostatic carcinoma cell lines and patient-derived carcinomas, whereas expression is not detected in normal prostate or BPH tissues. PTI-1 RNA is also found in additional human carcinomas of the breast, lung and colon. These results indicate that PTI-1 expression may be a common alteration in human carcinomas. The direct cloning of PTI-1 from an LNCaP cDNA library indicates that this novel gene is originally present in this prostatic carcinoma cell line and does not develop as a consequence of mutation resulting during transfection into CREF-Trans 6 cells or selection for tumor-formation in nude mice.

EF-1$\alpha$ is analogous to bacterial elongation factor-Tu (EF-Tu), both members of the GTPase superfamily of proteins (rev. 34–36). A primary function of EF-Tu/EF-1$\alpha$ is the process of kinetic proofreading that results in appropriate codon-anticodon binding interactions (36). Mutations in specific regions of EF-Tu result in altered biological function, including a dominant negative inhibition of protein synthesis by mutational replacement of Lys 136 by glutamate or glutamine in the G-4 GTPase region that interacts with guanine nucleotide release proteins (GNRPs) (37). EF-Tu mutants in *Escherichia coli* and Salmonella exhibit increases in missense error rates (38,39). Mutations in EF-1$\alpha$ can directly affect the frequency of frameshifting and amino acid misincorporations in *Saccharomyces cerevisiae* (40).

Single amino acid substitutions in EF-1$\alpha$ alter the selection and/or proofreading of the codon-anticodon match (40). Moreover, altering the level of EF-1$\alpha$ in *Saccharomyces cerevisiae* directly affects suppression of nonsense mutations further indicating a critical involvement in translational fidelity (41). In this context, the mutated EF-1$\alpha$ protein encoded by PTI-1 could modify normal EF-1$\alpha$ function resulting in decreased protein translational fidelity and an inability to suppress specific mutations in carcinomas. If this "translational infidelity" hypothesis is correct, PTI-1 may represent a mutated "genomic stability" gene (21) and an important contributor to the mutator phenotype of cancer cells and tumor progression.

An important early event in carcinogenesis may involve mutations that confer immortality or an enhanced cellular life span (20,21). During cellular senescence the levels and catalytic activity of EF-1α decrease (42). Forced expression of EF-1α in *Drosophila melanogaster* extends life-span in comparison with control flies (43). The reduction in proliferative capacity associated with senescence correlates with a reduced capacity for mitosis. In this respect, the recent demonstration that EF-1α may be an important element in mitotic spindle formation (44) may be relevant. As demonstrated in this report, the EF-1α sequence in PTI-1 contains a deletion of 67 amino acids and six point mutations in comparison with wild-type human EF-1α (FIGS. 8C–8D). Although the relevance of these alterations to EF-1α activity are unknown, it is possible that this gene undergoes a series of step-wise mutations during prostate cancer development. If this hypothesis is correct, changes in the structure of the PTI-1 gene could represent a genetic marker for prostatic carcinoma development and progression. Studies are currently in progress to test these hypotheses and to determine if expression of PTI-1 and/or genetically modified EF-1α genes in CREF-Trans 6 cells results in acquisition of oncogenic potential.

A previous limitation preventing the identification and cloning of novel oncogenes was the absence of a sensitive transfectable indicator cell line. This problem has been ameliorated with the identification of the CREF-Trans 6 clone (12). Using rapid expression cloning with the CREF-Trans 6 acceptor cell line and the DD technology, the novel putative oncogene PTI-1 displaying expression in human prostate, breast, lung and colon carcinomas has been identified and cloned. In comparative studies using NIH-3T3 cells, cotransfection of high molecular weight DNA from LNCaP cells and antibiotic resistance plasmid (pSV2neo) DNA did not result in tumors following injection of G418-resistant cells into nude mice (12). Rapid expression cloning with CREF-Trans 6 also results in the transfer of tumor-inducing oncogenes from a human breast carcinoma, a glioblastoma multiforme and a small cell lung carcinoma cell line and from a patient-derived metastatic colon carcinoma lesion (data not shown). Although the identifications of the dominant-acting genetic elements present in these human tumor DNA-transfected CREF-Trans 6 clones are not known, these exciting preliminary results suggest that this new acceptor cell line could prove useful for identifying and cloning potentially novel human oncogenes involved in the development of diverse human cancers.

References of the Second Series of Experiments

1. Garnick, M. B. (1994) *Scient. Amer.* 270, 72–81.
2. Epstein, J. I., Pizov, G. & Walsh, P. C. (1993) *Cancer* 71, 3582–3593.
3. Jewett, H. J., Bridge, R. W., Gray, J. F., Jr. & Shelly, W. M. (1968) *JAMA* 203, 403406.
4. Mukamel, E., Hanna, J. & deKernion, J. B. (1987) *Urol.* 30, 318–323.
5. Salo, J. O., Kivisaari, L., Rannikko, S. & Lehtonen, T. J. (1987) *Urol.* 137, 435–438.
6. Hricak, H., Dooms, G. C., Jeffrey, R. B., Arallone, A., Jacobs, D., Benton, W. K., Narayan, P. & Tanagho, E. A. (1987) *Radiology* 162, 331–336.
7. Anscher, M. S. & Prosnitz, R. (1987) *J. Urol.* 138, 1407–1412.
8. Lu-Yao, G. L., McLerran, D., Wasson, J. & Wennberg, J. E. (1993) *JAMA* 269, 2633–2655.
9. Barbacid, M. (1987) *Ann. Rev. Biochem.* 56, 779–827.
10. Fasano, O., Birnbaum, D., Edlund, L., Fogh, J. & Wigler, M. (1984) *Mol. Cell. Biol.* 4, 1695–1705.
11. Horoszewicz, J. S., Leong, S. S., Kawinski, E., Karr, J. P., Rosenthal, H., Ming Chu, T., Mirand, E. A. & Murphy, G. G. (1983) *Cancer Res.* 43, 1809–1818.
12. Su, Z.-z., Olsson, C. A., Zimmer, S. G. & Fisher, P. B. (1992) *Anticancer Res.* 12, 297–304.
13. Liang, P. & Pardee, A. B. (1992) *Science* 257, 967–971.
14. Jiang, H., Lin, J. & Fisher, P. B. (1994) *Mol. Cell. Different.* 2 (3), 221–239.
15. Jiang, H., Lin, J., Su, Z.-z., Herlyn, M., Kerbel, R. S., Weissman, B. E., Welch, D. R. & Fisher, P. B. (1995) *Oncogene*, in press.
16. Lin, J., Su, Z.-z., Grunberger, D., Zimmer, S. G. & Fisher, P. B. (1994) *Intl. J. Oncol.*, 5, 5–15.
17. Vita, J. R., Edwalds, G. M., Gorey, T., Housepian, E., Fetell, M. R., Guarini, L., Langer, J. A. & Fisher, P. B. (1988) *Anticancer Res.* 8, 297–302.
18. Guarini, L., Tempconi, M., Bruce, J. N., Bollon, A. P., Duigou, G. J., Moulton, T. A., Ferrone, S. & Fisher, P. B. (1990) *Int. J. Cancer* 46, 1041–1047.
19. Reddy, P. G., Graham, G. M., Datta, S., Guarini, L., Moulton, T. A., Jiang, H., Gottesman, M. M. & Fisher, P. B. (1991) *J. Natl. Cancer Inst.* 83, 1307–1315.
20. Fisher, P. B. (1984) in *Tumor Promotion and Cocarcinogenesis In Vitro, Mechanisms of Tumor Promotion*, ed. Slaga, T. J. (CRC Press, Florida), pp. 57–123.
21. Loeb, L. A. (1994) *Cancer Res.* 54, 5059–5063.
22. Rabbitts, T. H. (1994) *Nature* 372, 143–149.
23. Su, Z.-z., Austin, V. A., Zimmer, S. G. & Fisher, P. B. (1993) *Oncogene* 8, 1211–1219.
24. Riis, B., Rattan, S. I. S., Clark, B. F. C. & Merrick, W. C. (1990) *TIBS* 15, 420–424.
25. Sonenberg, N. (1993) *Current Biol.* 5, 955–960.
26. Lazaris-Karatzas, A. & Sonenberg, N. (1992) *Mol. Cell. Biol.* 12, 1234–1238.
27. Lazaris-Karatzas, A., Montine, K. S. & Sonenberg, N. (1990) *Nature* 345, 544–547.
28. De Benedetti, A., Joshi, B., Graff, J. R. & Zimmer, S. G. (1994) *Mol. Cell. Different.* 2 (4), 309–334.
29. Tatsuka, M., Mitsui, H., Wada, M., Nagata, A., Nojima, H. & Okayama, H. (1992) *Nature* 359, 333–336.
30. Grant, A. G., Flo-men, R. M., Tizard, M. L. V. & Grant, D. A. W. (1992) *Int. J. Cancer* 51, 740–745.
31. Chi, K., Jones, D. V. & Frazier, M. L. (1992) *Gastroenterology* 103, 98–102.
32. Lew, Y., Jones, D. V., Mars, W. M., Evans, D., Byrd, D. & Frazier, M. L. (1992) *Pancreas* 7,144–152.
33. Ender, B., Lynch, P., Kim, Y. H., Inamdar, N. V., Cleary, K. R. & Frazier, M. L. (1993) *Mol. Carcinog.* 7, 18–20.
34. Bourne, H. R., Sanders, D. A. & McCormick, F. (1990) *Nature* 348, 125–1:32.
35. Bourne, H. R., Sanders, D. A. & McCormick, F. (1991) *Nature* 349, 117–127.
36. Merrick W. C. (1992) *Microbiol. Rev.* 60, 291–315.
37. Hwang, Y. W., Sanchez, A. & Miller, D. L. (1989) *J. Biol. Chem.* 264, 8304–8309.
38. Tapio, S. & Kurland, C. G. (1986) *Mol. Gen. Genet.* 205, 186–188.
39. Hughes, D., Atkins, J. F. & Thompson, S. (1987) *EMBO J.* 6, 4235–4239.
40. Sandbaken, M. G. &, Culbertson, M. R. (1988) *Genetics* 120, 923–934.
41. Song, J. M., Picologlou, S., Grant, C. M., Firoozan, M., Tuite, M. F. & Liebman, S. (1989) *Mol. Cell. Biol.* 9, 4571–4575.

42. Cavallius, J., Rattan, S. I. S. & Clark, B. F. C. (1986) *Exper. Gerontol.* 21, 149–157.
43. Shepherd, J. C. W., Walldorf, U., Hug, P. & Gehring, W. J. (1989) *Proc. Natl. Acad. Sci. USA* 86, 7520–7521.
44. Marchesi, V. T. & Ngo, N. (1993) *Proc. Natl. Acad. Sci. USA* 90, 3023–3032.

Third Series of Experiments

The American Cancer Society estimates that 200,000 American men will have been diagnosed with prostate cancer in 1994 and 38,000 afflicted men will have died of this disease. The current methods for detecting early prostate cancer are limited in both their sensitivity and specificity. These include physical examination that might easily miss small or centrally located tumors, serum prostate-specific antigen (PSA) determination that is not specific to malignant prostate disease, and tissue biopsy in which samp-ing error may lead to erroneous benign diagnosis. Predictors and early detection of therapeutic relapse such as monitoring of PSA levels, ultrasound and bone scans are also unsatisfactory, as these require fairly bulky tumor regrowth before discovery.

Despite intensive scientific effort, the relevant genomic changes that mediate the development and evolution of prostate cancer remain to be defined. In addition, biochemical and molecular markers correlating with potential aggressiveness of a specific prostate carcinoma and the appropriate therapy that will effectively prevent disease progression are not currently available. It is now well established that many forms of cancer are the result of complex multifactor interactions and carcinogenesis is a multistep process. Genetic factors contributing to carcinogenesis include dominant acting oncogenes that promote the cancer phenotype and tumor suppressor genes that function as negative inhibitors of the cancer process. Our broad goals are to define prostate cancer in molecular terms and use this information to des:Lgn better diagnostic tools and therapies for this; malignancy. To achieve these objectives it will be necessary to identify and characterize genes that can both induce and inhibit this disease process. Once appropriate genetic mediators of human prostate cancer are identified this information will prove valuable for developing more effective diagnostic tools and ultimately for generating improved gene-based and immunologically-based therapies for this pervasive cancer.

The Rapid Expression Cloning (RExCS) System

A primary objective of investigators interested in the etiology of human cancer is the identification of gene(s) within tumor cells with oncogenic potential. One procedure used to achieve this goal involves the transfer of high molecular weight (HMW) DNA isolated from established tumor cell lines or primary tumors into appropriate cell lines by calcium-mediated DNA-transfection, lipofection, electroporation or other approaches. Target cells are then examined for signs of morphological transformation, i.e., focus formation. A modification of this approach involves cotransfection of target cells with HMW DNA plus a selectable antibiotic resistance gene, such as pSV2neo, selection for antibiotic resistance and then injection of pooled antibiotic resistant cells into nude mice to identify clones of cells with tumorigenic potential. The majority of studies using these approaches have relied on the immortal murine cell line NIH-3T3. Unfortunately, NIH-3T3 cells have generally not proven successful in identifying novel dominant-acting oncogenes from human tumor lines or clinical samples and even when successful, subsequent cloning of the transforming gene has revealed genetic elements not relevant to most human cancers. These findings emphasize the need for improved techniques to identify dominant-acting human cancer genes and the identification of more suitable target cell lines that can express novel tumor-inducing human oncogenes.

To identify dominant acting oncogenes in human prostate carcinoma cells applicants have used 2 approaches, both utilizing DNA cotransfection techniques with a new DNA-acceptor cell line, CREF-Trans 6, and tumor formation in nude mice as an endpoint. Cotransfection of CREF-Trans 6 with HMW DNA from the human prostate carcinoma cell line LNCaP and pSV2neo DNA, selection for G418 resistance and injection into nude mice resulted in tumor formation. In contrast, no transformed foci were apparent in similarly transfected CREF-Trans 6 cells maintained only in monolayer culture. No dominant acting focus forming or tumor inducing oncogene was detected in NIH-3T3 cells cotransfected with LNCaP and pSV2neo DNA. Both primary and secondary nude mouse tumor-derived CREF-Trans 6 cells contain human repetitive (Alu) sequences that are not present in untransfected CREF-Trans 6 cells. A common Alu fragment is present in Southern blots in both primary and secondary tumor derived CREF-Trans 6 cells. Tumor-derived CREF-Trans 6 cells also contain additional Alu sequences of different apparent molecular sizes. This data provided initial supportive evidence that a human gene(s) potentially capable of inducing a tumorigenic phenotype in nontumorigenic CREF-Trans 6 cells had been transferred from the human prostate carcinoma cell line LNCaP. Using both molecular and immunological approaches tumor-derived CREF-Trans 6 cells have been used to: (a) identify and clone novel genes, termed prostate tumor inducing genes (PTI-1, PTI-2, FIGS. 13A and 13B and PTI-3, FIGS. 14A and 14B potentially involved in the etiology of human prostate carcinoma; and (b) produce monoclonal antibodies reacting with the surface of human prostate carcinoma cells and the cloning of a cDNA encoding a novel tumor associated antigen, termed prostate carcinoma tumor antigen gene (PCTA-1, FIGS. 15A–15E).

Other Applications of RExCS: Cotransfection of CREF-Trans 6 with pSV2neo DNA and high molecular weight DNA from a human glioblastoma multiforme cell line (GBM-18), a human breast carcinoma cell line (T47D) and a human small cell lung carcinoma cell line (NCI-H69) results in tumor formation in nude mice. Similarly, cotransfection of CREF-Trans 6 with pSV2neo DNA and high molecular weight DNA from a patient-derived metastatic colorectal carcinoma results in tumor formation in nude mice. Tumor-derived cell lines have been isolated and can now be used: to clone the transforming genetic elements mediating the tumorigenic phenotype; and with the SEM procedure to develop potentially novel MAbs reacting with TAAs expressed by specific human cancers.

Prostate Tumor Inducing Gene-1 (PTI-1): PTI-1 was initially identified in LNCaP DNA transfected tumor-derived CREF-Trans 6 cells using an approach termed RNA differential display (DD). DD permits the identification and cloning of differentially expressed mRNAs encoded by closely related celL types. The basic DD approach involves a series of interrelated steps, including: (a) isolating mRNA from two closely related cell types; (b) producing reverse transcribed-PCR (RT-PCR) products using a primer that anchors the PCR products to the 3' end of the mRNA and 5' primers containing arbitrary oligonucleotides of various sizes; (c) running RT-PCR products from both cell types in adjacent lanes of a sequencing gel; (d) cutting differentially expressed bands out of the sequencing gel, eluting the PCR product and PCR amplification; (e) testing for expression of the PCR product using Northern blots containing relevant RNA samples; and (f) sequencing appropriately expressed sequences to determine identity with previously reported genes. Improvements in DD include the use of a subtraction hybridization step prior to performing RT-PCR. This technical improvement to DD results in a dramatic reduction in the number of false positives, that can exceed 40% using standard DD.

The DD cloning strategy has now been successfully used with untransfected CREF-Trans 6 cells and an LNCaP DNA transfected nude mouse tumor derived CREF-Trans 6 clone, CREF-Trans 6: 4 NMT to identify PTI-1 (PTI-2 and PTI-3- to be described below). An anchored oligo-dT primer consisting of 12 Ts plus two additional 3' bases, that provides specificity, was used to anneal the beginning of a subpopulation of the poly(A) tails of the mRNAs for reverse transcription. A set of arbitrary primers was used as a 5'-primer for PCR amplification of the cDNAs generated by reverse transcription from the mRNAs. These amplified cDNA fragments were then separated by size to a maximum of 500 bp on a denaturing polyacrylamide gel. A differentially expressed band of 214 bp that was present in CREF-Trans 6: 4 NMT but not in CREF-Trans 6 was cut out of the gel, electroeluted in TBE and reamplified by PCR using the same primers as used for DD. The purified 214 bp DNA fragment from the 1% agarose gel was then cloned into the PCR™II vector and transformed in OneShot™ competent cells. This sequence referred to as 214 bp PTI-1, was tested for expression using Northern blotting analysis. PTI-1 was expressed in LNCaP and CREF-Trans 6: 4 NMT, but not in CREF-Trans 6, human breast carcinoma cells (MCF7), human glioblastoma multiforme (GBM-18) or human melanoma cells (H0-1 and C8161). Sequence analysis of the 214 bp PTI-1 DNA fragment using the Sanger sequencing procedure indicates no homology to previously reported genes deposited in various gene banks (GenBank (R), Brookhaven Protein Data Bank, EMBL Data Library). In order to identify the 5'- and 3'-flanking regions of the 214 bp DNA, rapid amplification of cDNA ends (RACE) was performed. The RACE approach is a procedure for amplification of nucleic acid sequences from a mRNA template between a defined internal site and an unknown sequence representing either the 3' or 5' end of the mRNA. Using RACE and primers designed from the 214 bp PTI-1 sequence, a 1.8 Kb PTI-1 DNA fragment was generated by PCR. Northern analysis using the 1.8 Kb PTI-1 DNA fragment produced the same reactivity pattern as observed with the 214 bp PTI-1 DNA fragment. Approximately 600 bp of the 5' region of the PTI-1 DNA fragment was sequenced and found to display no homology to reported eucaryotic gene sequences, but rather ~85% homology to 23S ribosomal RNA from *Mycoplasma hyopneumoniae*) (PNAS paper). This 1.8 Kb PTI DNA was called PTI-3 and will be described later. This 1.8 Kb PTI DNA was later used to screen an LNCaP cDNA library constructed in the Uni-ZAP XR vector. Two clones were identified. One is clone 18, which is called PTI-1; another, clone 8, is called PTI-2 and will be described later.

The PTI-1 gene is composed of two parts; one is 5'-RACE extended region (1–215 bp) and another clone 18 part. Clone 18 (PTI-1) contains 1937 bp (29 bp+1908 bp) insert in pBluescript vector. The experiment demonstrates that the 29 bp at the 5'-end comes from wrong reverse transcription because of lower temperature and secondary structure of RNA, so that this 29 bp sequence was replaced by the right sequence obtained by RACE method and did not show in the complete sequence of PTI-1. The sequence from 30–1937 bp (1907 bp) of clone 18 was shown as the sequence 216 bp-2123 bp (1907 bp) in FIG. 3 (manuscript). The plasmid deposit is clone 18 (PTI-1). A pair of oligonucleotides with sequences in the 5' region of the 1.8 Kb PTI-1 DNA was synthesized and RT-PCR was performed using mRNA isolated from both cell lines and human tissue samples. This analysis indicates that PTI-1 is expressed in CREF-Trans 6: 4 NMT, LNCaP, DU-145 (a hormone independent human prostate carcinoma cell line) , 7 of 8 patient-derived prostate carcinomas. In contrast, PTI-1 is not expressed in CREF-Trans 6, H0-1, MCF-7 or tissue from normal human prostates or benign prostatic hypertrophy (BPH). These studies indicate that PTI-1 is a novel human oncogene that may be a mediator of or that is associated with transformation and tumorigenesis in human prostate carcinoma cells.

To identify a full-length PTI-1 cDNA, an LNCaP cDNA library was constructed in the Uni-ZAP XR vector. Screening the LNCaP library using the 1.8 Kb PTI-1 DNA probe resulted in the identification of an ~2.0 Kb PTI-1 cDNA from this library. Two approaches indicate that this PTI-1 cDNA is a full-length cDNA. One approach uses primer extension analysis of the ~2.0 Kb cDNA and the second approach involves in vitro translation of in vitro RNA transcribed from the ~2.0 Kb cDNA. Using a reticulocyte translation system, the transcribed RNA from the ~2.0 Kb PTI-1 cDNA generates several protein products with a predominant protein of approximately 46 kDa. Complete sequence analysis and comparison with existing DNA data bases of the ~2.0 Kb PTI-1 cDNA isolated from the LNCaP cDNA library indicates that PTI-1 is a novel fusion gene. PTI-1 consists of a unique 630 bp 5'sequence and a 3' sequence homologous to a truncated and mutated form of human elongation factor-1 alpha. A full-description of PTI-1 with sequence and specific properties can be found in our PNAS paper.

PTI-1: Using primer sequences for bases present in the unique 630 bp 5' region of PTI-1 (A and L) and primer sequences corresponding to the elongation factor-1 alpha region of PTI-1 and RT-PCR approaches, the following additional information is currently available relative to PTI-1: (A) Tissue distribution studies (using tissue poly A$^+$ mRNA blots from Clontech) have been performed using the A and L primers and a region corresponding to the elongation factor-1 alpha homologous region of PTI-1 as probes. The unique region of PTI-1 is only expressed in skeletal muscle and colon tissue, whereas the elongation factor-1 alpha hybridizes with an mRNA present in all of the tissue samples. These include, spleen, thymus, prostate, testis, ovary, small intestine, colon, peripheral blood leukocyte, heart, brain, placenta, lung, liver, skeletal muscle, kidney and pancreas. These studies reinforce our previous observations that the unique region of PTI-1 is not expressed in normal human prostate. (B) Expression of PTI-1 (A and L primers) is reduced in LNCaP cells treated with: a phorbol ester tumor promoter (12-0-tetradecanoyl-phorbol -13-acetate (TPA), that induces apoptosis in LNCaP cells; suramin; epidermal growth factor; transforming growth factor-alpha; or the synthetic androgen R1881. Using primers for prostate specific antigen (PSA) reductions in PTI-1 mRNA levels using the same agents are also apparent in LNCaP cells. These results suggest that similar changes inducing downregulation of PSA expression can also decrease PTI-1 expression in human prostate carcinoma cells. (C) Expression is apparent in human promyelocytic leukemia (HL-60) and an additional leukemic cell line K562. When induced to differentiate by TPA, PTI-1 expression decreases and is no longer apparent by 3 hr posttreatment in HL-60 cells. This change in mRNA levels after TPA treatment suggests that decreased expression of PTI-1 may be modulated as a function of growth arrest and terminal differentiation in HL-60 cells; (D) Expression is apparent in CREF cells transformed by diverse acting oncogenes, including wild-type 5 adenovirus (Ad5), mutant type 5 adenovirus (H5hr1), Ha-ras oncogene, v-src, human papilloma virus type 18 (HPV-18) and HPV-51. Using a dexamethasone (DEX) inducible Ad5 E1A transforming gene under the transcriptional control of a mouse mammary tumor virus promoter, expression of PTI-1 is only seen in the presence of DEX. Under these culturing conditions, DEX also results in E1A expression and transformation. These data indicate that induction of PTI-1 directly correlates with transformation induced by mechanistically different oncogenes. Figure of Northern blot; FIG. 11).

Uses for PTI-1: The unique region of PTI-1 can be used to: (A) Produce primers for RT-PCR that will distinguish between prostate carcinoma and normal or BPH tissue samples (diagnostic applications); (B) Permit development of a blood test to identify prostate carcinoma cells that have metastatic potential and that have escaped from the prostate (diagnostic applications); (C) Permit identification of additional carcinomas, i.e., breast, colon and lung, in the blood stream that have resulted from metastatic carcinoma spread (diagnostic applications) ; and (D) Develop an antisense vector and/or ribozyme approach to Inhibit expression and induce growth arrest and/or apoptosis in prostate carcinoma cells, and perhaps other carcinoma and leukemic cells (therapeutic applications).

The mutated elongation factor 1-alpha region of PTI-1 may prove useful to: (A) Identify genetic changes in cells predisposing to carcinoma development and progression (diagnostic applications); (B) Identify point mutations and or deleted regions of this gene that could prove useful for predicting carcinoma development and progression (diagnostic applications); and (C) Develop antisense and ribozyme strategies to inhibit expression of the mutant form of elongation factor 1-alpha resulting in suppression of carcinoma growth (therapeutic applications).

PTI-1 and Prostate Tumor Inducing Gene-2 (PTI-2): A cDNA library was prepared from LNCaP cells in the Uni-ZAP XR vector (Stratagene). The LNCaP cDNA library was screened with a $^{32}$P-labeled 1.8 Kb DNA (PTI-3) containing the 214 bp DNA obtained by the differential display procedure. The contents of ten plates of 150 mm×15 mm (containing ~2×10$^4$ plaques/plate) were transferred in duplicate to nylon membranes. Hybridization was performed using the following conditions: 5% dextran sulfate, 45% deionized formamide, 4× SSC, 1 mM phosphate buffer (pH 7.5), 0.5% SDS, 5% Denhardt's reagent at 42° C. in a Hybridization Incubator Model 400 (Flobbin Scientific); washing at 55° C. for 60 min in a solution of 0.25% SDS and 1× SSC. Positive plaques obtained in the first round were screened in duplicate for a second round and then with in vivo excision produced plasmids containing gene inserts in the pBluescript vector. Plasmids containing the longest inserts were identified by Southern blotting and probing with the 1.8 Kb (PTI-3) DNA probe. Two clones were identified using this approach: clone 8 (PTI-2) and clone 18 (partial sequence of PTI-1).

The full sequence of PTI-1 contains 2,123 bp, the 5'-flanking (1–215 bp) was obtained by RACE 5'-extension (GIBCO-BRL), the remaining 216–2,123 bp was obtained by sequencing clone 18. The RACE 5' extension was performed with two oligonucleoticdes, both located within the 5'-end of clone 18. One oligonucleotide is a 23 mer (5'-CCTTGCATATTAACATAACTCGC-3') (SEQ. ID NO.13) and the other oligonucleotide is a 20 mer (5'-AAGTCGCCCTATTCAGACTC-3') (SEQ. ID NO.14). A comparison of PTI-1 with GenBank indicates that the 3'-part of this gene (630 to 2,123 bp) has 97% homology to human elongation factor 1-alpha. The 5'-part of this gene (1–629 bp) does not show any homology to known eucaryotic genes.

Comparison of PTI-2 with Genbank indicates that it has 86.9% identity in 1356 bp overlap with *Mycoplasma floccular* 16S ribosomal RNA and 23S ribosomal RNA genes, but no homology to any previously identified eucaryotic genes.

Prostate Tumor Inducing Gene-3 (PTI-3): To identify genes specifically expressed in CREF-Trans 6:4 NMT (transformed by DNA from LNCaP cells), but not CREF-Trans 6 cells applicants have used the differential RNA display procedure. This approach resulted in the identification of a 214 bp DNA fragment in CREF-Trans 6:4 NMT that was not present in CREF-Trans 6 cells (PNAS paper). Northern blotting indicates that this 214 bp DNA is expressed in CREF-Trans 6:4 NMT and LNCaP cells, but not in CREF-Trans 6 cells. A 20 mer oligonucleotide with the sequence 5'-AACTAACTGGAGGACCGAAC-3' (SEQ. ID NO.15) within this 214 bp DNA fragment was used to obtain extended sequences beyond the 214 bp DNA using the RACE method. A cDNA from LNCaP cells was synthesized with oligodT. To the 3'-end a polydC was added by terminal deoxynucleotide transferase. When the anchor primer (using the protocol of the GIBCO-BRL 5' RACE kit) and the above 20 mer were used to perform PCR amplification of cDNA from LNCaP cells, a 1.8 Kb DNA fragment containing a partial sequence of the 214 bp DNA was obtained. This 1.8 Kb DNA fragment displays the same Northern blotting pattern as does the unique 214 bp sequence.

The 1.8 Kb DNA fragment. was cloned into PCR™ II vector by using the TA cloning kit (Invitrogen). The sequence of this 1.8 Kb DNA was determined by Sanger's method (Sequenase kit, version 2.0 USB). The 1.8 Kb DNA contains a partial sequence of PTI-1/3. The 5' and 3' end of PTI-3 gene remains to be confirmed. The insert of PTI-3 1.8 Kb insert can be recovered from the PCR™ II vector by digestion with EcoRI. A comparison of the sequence of PTI-3 with Genbank data base indicates that this gene has 87% identity in 1858 bp overlap with *Mycoplasma floccular* 16S ribosomal RNA and 23S ribosomal RNA genes, and it has 89.8% identity in 1858 bp overlap with *Mycobacterium hyopneumoniae* 23S ribosomal RNA gene.

Prostate Carcinoma Tumor Antigen Gene-1 (PCTA-1): Evidence that tumor derived CREF-Trans 6 cells transfected with LNCaP DNA encode genetic information related to human prostate cancer has been obtained using an approach termed surface epitope masking (SEM) . The SEM procedure involves the selective blocking of surface antigens present in a genetically engineered cell (referred to as a "tester") with high-titer polyclonal antibodies against the untransfected parental cell (referred to as a "driver"). Surface-epitope-masked tester cells are injected into BALB/c mice, immune spleen cells are then taken from these mice and they are fused with myeloma cells. This process results in the efficient generation of hybridomas that secrete monoclonal antibodies (MAbs) that react with cell-surface antigens on transfected tester cells and with additional cell types that express the same surface molecules. LNCaP transfected tumor-derived CREF-Trans 6 cells, CREF-Trans 6 4 NMT, have been used as a tester cell line.

The SEM procedure was applied resulting in the development of hybridomas producing nkbs reacting with tumor associated antigens (TAAs) on the surface of the original LNCaP cell line used to obtain human prostatic carcinoma DNA, primary and secondary nude mouse transfectants derived from tumors and two additional human prostatic carcinoma cell lines (DU-145 and PC-3). These MAbs are designated Pro 1.1 to 1.5. Specific MAbs also display reactivity to two human breast carcinoma cell lines (MCF7 and T47D). However, they do no: react with normal human skin fibroblasts (NHSF-1), two colon carcinoma cell lines (WiDr and LS174T), two human melanoma cell lines (HO-1 and MeWo) or a human glioblastoma multiforme cell line (GBM-18). Immunoprecipitation analyses of $^{35}$S-methionine labeled cell extracts with PCTA-1 Pro 1.5 MAbs indicate that primary and secondary nude mouse tumor-derived LNCaP-transfected CREF-Trans 6 cells, LNCaP and DU-145 cells contain an approximately 42 kDa protein that is not present in untransfected CREF-Trans 6 or additional human tumors (including melanoma and glioblastoma multiforme). These results indicate that a gene encoding human prostatic carcinoma (and possibly breast carcinoma) TAAs has been transferred and is now expressed in CREF-Trans 6 cells.

To identify the gene encoding PCTA-1, a SEM-derived MAb (Pro 1.5) was used to screen an LNCaP cDNA expression library (PicoBlue Immunoscreening Kit, STRATAGENE). mRNA was isolated from LNCaP cells after passage of total RNA through an oligo-dT column (GIBCO). LNCaP cDNA libraries were constructed in the Uni-ZAP vector (Stratagene) Screening of the cDNA library was performed as follows: (1) SURE host cells were plated on fifteen 150 mm×15 mm NZY plates with 6.5 ml of top agar (~2×10$^4$ plaques/plate); (2) After 3.5 hr incubation at 42° C., nitrocellulose filters soaked with 10 mM IPTG solution were applied to the plates and plaques were lifted; (3) The filters containing the plaque lifts were washed 3 or 4× with TBST (20 mM Tris-HCl pH7.5, 150 mM NaCl, 0.05% Tween-20) (Polyoxyethylene (20) sorbitan monolaurate) and soaked in blocking solution (1% BSA in TBS [20 mM Tris-HCl pH 7.5, 150 mM NaCl)] for 1 hr at room temperature; (4) The filters were then transferred to fresh blocking solution containing Pro 1.5 ascites (1:500 dilution) followed by incubation for 3 hr at room temperature with gentle rocking; (5) Filters were washed 4× with TBST buffer; (6) The filters were transferred into fresh blocking solution containing Ab-AP conjugate (1:2000 dilution) and incubated for 1 hr at room temperature; (7) The filters were washed 4× with TBST and placed in a developing solution containing 0.3 mg/ml NBT (nitro blue tetrazolium, 0.15 mg/ml of BCIP (5-bromo-4-chloro-3-indolyl phosphate), 100 mM Tris-HCl pH 9.5, 100 mM NaCl, 5 mM MIgCl$_2$); and (8) The reaction was terminated with stop solution containing 20 mM Tris-HCl, pH 2.9 and 1 mM EDTA) and the filters were dried. In the first round of screening with Pro 1.5, only 2 positive clones were obtained from over 3×10$^6$ (15×2×10$^4$) colonies. Screening was performed a second time and clones were isolated and characterized. Using this approach antibody-positive clones were identified that contain a cDNA insert of ~3.8 Kb. Sequence analysis of PCTA-1 indicates no homology to previously identified genes. The 5' region of PCTA-1 is homologous to several expressed sequence tags [including *Homo sapiens* partial cDNA sequence clone HEC077, clone c-zvh01, clone hbc1127 (3' end), clone hbc1208 (5' end) and clone hbc1074 (3'end)] (see below). In vitro translation in a rabbit reticulocyte lysate system, with and without immunoprecipitation with Pro 1.5, indicate the presence of an approximately 36 kDa protein. These observations indicate that the PCTA-1 cDNA encodes a protein that is the putative tumor associated antigen present on prostate cancer cells identified using the SEM approach.

| Comparison of PCTA-1 with *Homo sapiens* cDNA clones Identity PCTA-1 *Homo sapiens* partial cDNA sequence HEC077 c-zvh01 hbc 1127 hbc1208 hbc1074 | | | |
|---|---|---|---|
| | (3' end) | (5' end) | (3' end) |
| 94.9% 2123/1732 1-395 | | | |
| 99% 2118/1858 | 1-261 | | |
| 88.8% 3853/3562 | | 1-290 | |
| 93.5% 2630/2818 | | | 1-186 |
| 84% 2728/2825 | | | 1-98 |

(1) SEM-Derived MAbs Specific for the Multidrug Resistance (MDR) P-Glycoprotein encoding an 170,000 Molecular Weight Cell Surface Transport Protein: To develop MAbs specific for the P-glycoprotein mediating MDR, CREF-Trans 6 cells were transfected with a human MDR-1 gene and cells resistant to colchicine were isolated. These MDR clones contain the MDR gene, express MDR mRNA and are cross-resistant to toxicity induced by several chemotherapeutic agents. MDR-CREF-Trans 6 cells were coated with CREF-Trans 6 polyclonal antibodies, injected into BALB/c mice, spleens were isolated and used to from hybridomas. Hybridomas secreting MAbs specific for MDR-CREF-Trans 6 cells were isolated. These SEM-derived MAbs react with MDR-CREF-Trans 6 cells as demonstrated by fluorescence activated cell sorter (FACS) analysis, confirming their interaction with epitopes of the P-glycoprotein expressed on the cell surface. In addition, human breast carcinoma (MCF-7) cells transfected with the same MDR-1 gene and displaying the MDR phenotype also react with the SEM-derived MAbs. In contrast, non-MDR parental MCF-7 cells do not react with these MAbs. These results indicate that the SEM approach can be used to develop MAbs specific for defined cell surface-expressed molecules. (Full details in our JNCI manuscript—Shen, Su, Olsson, Goldstein & Fisher).

(2) SEM-Derived MAbs Specific for the Human Leukocyte Interferon α (IFN-α) Receptor: To develop MAbs specific for the Human IFN-α receptor, CREF-Trans 6 cells were transfected with a human IFN-α receptor expression vector and clones expressing the receptor were isolated. These clones interacted with labeled IFN-α, whereas non-transfected CREF-Trans 6 cells do not react with IFN-α. These results provide further documentation of the effectiveness of the SEM approach in producing MAbs specific for defined cell surface-expressed molecules.

(3) SEM-Derived MAbs Specific for the Human Immune Interferon (IFN-γ) Receptor: To develop MAbs specific for the Human IFN-γ receptor, CREF-Trans 6 cells were transfected with a human IFN-γ receptor expression vector and clones expressing the receptor were isolated. These clones interacted with labeled IFN-γ, whereas non-transfected CREF-Trans 6 cells do not react with IFN-γ. These results provide further documentation of the effectiveness of the SEM approach in producing MAbs specific for defined cell surface-expressed molecules.

(4) SEM-Derived MAbs Reacting with Human Prostate Carcinomas: To determine if CREF-Trans 6 cells containing a putative human prostate tumor inducing gene(s), CREF-Trans 6:4 NMT, display tumor associated antigens (TAAs) also expressed on human prostate cancer cells, the SEM approach has been used. This procedure and the experimental results using the CREF-Trans 6:4 NMT clone is described in our JNCI manuscript (Shen et al., JNCI 86:91–98, 1994). The SEM-derived Pro MAbs (Pro 1.1, Pro 1.2, Pro 1.3, Pro 1.4 and Pro 1.5) display reactivity with LNCaP cells as well as two additional human prostate carcinomas, DU-145 and PC-3. Specific Pro MAbs also display surface reactivity with two human breast carcinoma cell lines, T47D and MCF-7. These MAbs are now being tested for reactivity using in situ immunohistochemistry with sections obtained from patients with prostate cancer. The ability to generate these Pro MAbs by SEM indicate that this approach can also be used to produce MAbs specific for cell surface expressed molecules of unknown origin. The Pro 1.4 MAbs have also been used in combination with expression cloning and human prostate carcinoma library screening to identify and clone the gene encoding the specific TAAs, PCTA-1.

(5) SEM-Derived MAcs Reacting with Human Breast Carcinomas: To determine if CREF-Trans 6 cells containing a putative human breast carcinoma tumor inducing gene(s), CREF-Trans 6:T47D NMT, display TAAs also expressed in human breast carcinoma cells, the SEM approach has been used. This approach resulted in the development of SEM-derived Br-car (breast: carcinoma) MAbs (4.2.1 and 5.2.4) that react with T47D and MCF-7 human breast carcinoma cell lines. In situ immunohistochemistry (total of 10 samples) indicate that the SEM-derived Br-car MAbs also react with carcinoma sections from patients with ductal and medullary breast carcinomas (FIGS. 12A–12D). These MAbs are negative in sections of human melanoma and a small cell lung carcinoma (FIGS. 12A–12D). The ability to generate these Br-car MAbs by SEM provide additional evidence that this approach can be used to produce MAbs specific for cell surface expressed molecules of unknown origin.

Potential Applications for SEM-Approach and SEM-Derived MAbs: (A) The SEM-approach represents a general strategy for producing MAbs specific for molecules expressed on the cell surface. These can include, but are not limited to, novel TAAs, growth factor receptors, T-cell reactive epitopes, cell surface antigens (representing different developmental stages), surface expressed oncogene products, viral encoded proteins found on the cell surface, surface antigens expressed as a function of tumor progression (e.g., antigens associated with benign disease and metastatic disease), surface antigens eliciting reactivity with non-specific immunoreactive cells (i.e., NK cells and macrophages) and surface antigens eliciting autoimmune diseases (diagnostic and therapeutic applications); (B) SEM-derived MAbs can be used for in situ immunohistochemistry to identify specific cell surface expressed molecules, including growth factor receptors, cell surface antigens, surface expressed oncogene products, TAAs and viral encoded proteins found on the cell surface (diagnostic applications); (C) SEM-derived MAbs can be used to target toxins and radionuclides to tumor cells (therapeutic applications); (D) SEM-derived MAbs with high reactivity toward specific clinically relevant target molecules can be used to develop chimerized (human-mouse) and humanized MAbs for both diagnostic applications and therapeutic applications in humans; (E) SEM-derived MAbs can be used to clone genes encoding TAAs and additional cell surface expressed molecules of unknown structure. These genes can then be used for diagnostic applications and ultimately therapeutic applications; (E) SEM-derived MAbs can be used to identify potentially important TAAs. Once appropriate genes and antigens are identified they can be used as part of a strategy to vaccinate against specific TAAs (therapeutic applications).

What is claimed is:

1. An isolated mammalian nucleic acid molecule having the sequence of Prostate Tumor Inducing Gene-1 as set forth in SEQ. ID No. 16.

2. An isolated mammalian RNA molecule of claim 1.

3. An isolated nucleic acid probe of at least 15 nucleotides capable of specifically hybridizing to, which is fully complementary to, the coding region of a sequence of the nucleic acid molecule of claim 1.

4. A DNA molecule of claim 3.

5. An isolated mammalian nucleic acid molecule of claim 4 operatively linked to a promoter of RNA transcription.

6. An RNA molecule of claim 3.

7. A method of detecting expression of a Prostate Tumor Inducing Gene-1 in a cell which comprises obtaining total mRNA from the cell, contacting the mRNA so obtained with a labeled nucleic acid molecule of claim 3 under hybridizing conditions permitting specific hybridization of the labeled nucleic acid molecule of claim 3 and the mRNA, and determining the presence of mRNA hybridized to the molecule, thereby detecting the expression of the Prostate Tumor Inducing Gene-1 in the cell.

8. A method of detecting expression of a Prostate Tumor Inducing Gene-1 in tissue sections which comprises contacting the tissue sections with a labeled nucleic acid molecule of claim 3 under hybridizing conditions permitting specific hybridization of the labeled nucleic acid molecule of claim 3 and the mRNA in the tissue sections, and determining the presence of mRNA hybridized to the molecule, thereby detecting the expression of the Prostate Tumor Inducing Gene-1 in tissue sections.

* * * * *

UNITED STATES PATENT AND TRADEMARK OFFICE
CERTIFICATE OF CORRECTION

PATENT NO. : 5,851,764
APPLICATION NO. : 08/371377
DATED : December 22, 1998
INVENTOR(S) : Paul B. Fisher et al.

It is certified that error appears in the above-identified patent and that said Letters Patent is hereby corrected as shown below:

In the Specifications:

Column 1, lines 12-16:
The invention disclosed herein was made with Government support under NIH Grants CA 35675 and CA 43208 from the Department of Health and Human Services. Accordingly, the Government has certain rights in this invention.

should read

--STATEMENT REGARDING FEDERALLY SPONSORED RESEARCH OR DEVELOPMENT
This invention was made with government support under grant numbers CA35675 and CA43208 awarded by the National Cancer Institute. The government has certain rights in the invention.--

Signed and Sealed this
Fourteenth Day of May, 2013

Teresa Stanek Rea
*Acting Director of the United States Patent and Trademark Office*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( i i i ) HYPOTHETICAL: NO ( i v ) ANTI-SENSE: NO ( x i ) SEQUENCE DESCRIPTION: SEQ ID NO:1:

G A G T C T G A A T    A G G G C G A C T T                                                            2 0

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (i i) MOLECULE TYPE: other nucleic acid
        (A) DESCRIPTION: /desc = "Synthetic"

(i i i) HYPOTHETICAL: NO (i v) ANTI-SENSE: YES (x i) SEQUENCE DESCRIPTION: SEQ ID NO:2:

AGTCAGTACA GCTAGATGCC    20

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Synthetic DNA"

(i i i) HYPOTHETICAL: NO (i v) ANTI-SENSE: NO (x i) SEQUENCE DESCRIPTION: SEQ ID NO:3:

AGACACAGGC CAGGTATTTC AGGTC    25

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Synthetic DNA"

(i i i) HYPOTHETICAL: NO (i v) ANTI-SENSE: NO (x i) SEQUENCE DESCRIPTION: SEQ ID NO:4:

CACGATGGTG TCCTTGATCC ACTTC    25

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Synthetic DNA"

(i i i) HYPOTHETICAL: NO (i v) ANTI-SENSE: NO (x i) SEQUENCE DESCRIPTION: SEQ ID NO:5:

TCTTACTCCT TGGAGGCCAT G    21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
  (A) DESCRIPTION: /desc = "Synthetic DNA"

(i i i) HYPOTHETICAL: NO (i v) ANTI-SENSE: NO (x i) SEQUENCE DESCRIPTION: SEQ ID NO:6:

CGTCTTCACC ACCATGGAGA A 21

(2) INFORMATION FOR SEQ ID NO:7:

(i) SEQUENCE CHARACTERISTICS:
    (A) LENGTH: 59 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:7:

CGGCCCGAGC TCGTGCCGAA TTCGGCCCGA GAGCGTTAAA GTGTGATGGC GTACATCTT 59

(2) INFORMATION FOR SEQ ID NO:8:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (i i) MOLECULE TYPE: other nucleic acid
  (A) DESCRIPTION: /desc = "Synthetic DNA"

(i i i) HYPOTHETICAL: NO (i v) ANTI-SENSE: NO (x i) SEQUENCE DESCRIPTION: SEQ ID NO:8:

TTTTTTTTTT TTGC 14

(2) INFORMATION FOR SEQ ID NO:9:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (i i) MOLECULE TYPE: other nucleic acid
  (A) DESCRIPTION: /desc = "Synthetic DNA"

(i i i) HYPOTHETICAL: NO (i v) ANTI-SENSE: NO (x i) SEQUENCE DESCRIPTION: SEQ ID NO:9:

ACCGACGTCG ACTATCCATG AACA 24

(2) INFORMATION FOR SEQ ID NO:10:

(i) SEQUENCE CHARACTERISTICS:
    (A) LENGTH: 20 base pairs
    (B) TYPE: nucleic acid
    (C) STRANDEDNESS: single
    (D) TOPOLOGY: linear ( i i ) MOLECULE TYPE: other nucleic acid
    ( A ) DESCRIPTION: /desc = "Synthetic DNA"

( i i i ) HYPOTHETICAL: NO ( i v ) ANTI-SENSE: NO ( x i ) SEQUENCE DESCRIPTION: SEQ ID NO:10:

AACTAAGTGG AGGACCGAAC      20

( 2 ) INFORMATION FOR SEQ ID NO:11:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Synthetic DNA"

( i i i ) HYPOTHETICAL: NO ( i v ) ANTI-SENSE: NO ( x i ) SEQUENCE DESCRIPTION: SEQ ID NO:11:

CCTTGCATAT TAACATAACT CG      22

( 2 ) INFORMATION FOR SEQ ID NO:12:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Synthetic DNA"

( i i i ) HYPOTHETICAL: NO ( i v ) ANTI-SENSE: NO ( x i ) SEQUENCE DESCRIPTION: SEQ ID NO:12:

AAGTCGCCCT ATTCAGACT      19

( 2 ) INFORMATION FOR SEQ ID NO:13:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Synthetic DNA"

( i i i ) HYPOTHETICAL: NO ( i v ) ANTI-SENSE: NO ( x i ) SEQUENCE DESCRIPTION: SEQ ID NO:13:

CCTTGCATAT TAACATAACT CGC      23

( 2 ) INFORMATION FOR SEQ ID NO:14:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear (  i  i  ) MOLECULE TYPE: other nucleic acid
    ( A ) DESCRIPTION: /desc = "Synthetic DNA"

(  i  i  i  ) HYPOTHETICAL: NO (  i  v  ) ANTI-SENSE: NO (  x  i  ) SEQUENCE DESCRIPTION: SEQ ID NO:14:

AAGTCGCCCT ATTCAGACTC                    20

( 2 ) INFORMATION FOR SEQ ID NO:15:

(  i  ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i  i  ) MOLECULE TYPE: other nucleic acid
        ( A ) DESCRIPTION: /desc = "Synthetic DNA"

(  i  i  i  ) HYPOTHETICAL: NO (  i  v  ) ANTI-SENSE: NO (  x  i  ) SEQUENCE DESCRIPTION: SEQ ID NO:15:

AACTAACTGG AGGACCGAAC                    20

( 2 ) INFORMATION FOR SEQ ID NO:16:

(  i  ) SEQUENCE CHARACTERISTICS:
        ( A ) LENGTH: 2128 base pairs
        ( B ) TYPE: nucleic acid
        ( C ) STRANDEDNESS: single
        ( D ) TOPOLOGY: linear (  i  i  ) MOLECULE TYPE: cDNA (  i  i  i  ) HYPOTHETICAL: NO (  i  v  ) ANTI-SENSE: NO (  i  x  ) FEATURE:
        ( A ) NAME/KEY: CDS
        ( B ) LOCATION: 621..1817

(  x  i  ) SEQUENCE DESCRIPTION: SEQ ID NO:16:

```
GTATACGAAA  TCATAAAATC  TCATAGATGT  ATCCTGAGTA  GGGCGGGGCC  CGTGAAACCC     60

TCTGAATCTG  CGGCCACCAC  CCGGTAAGGC  TAAATACTAA  TCAGACACCG  ATAGTGAACT    120

AGTACCGTGA  GGGAAAGGTG  AAAAGAACCC  GAGAGGGGAG  TGAAATAGAT  TCTGAAACCA    180

TTTACTTACA  AGTGGTCCAT  TTACTTACAA  GTGTCAGAGC  ACGTTAAAGT  GTGATGGCGT    240

ACATCTTGCA  GTATGGGCCG  GCGAGTTATG  TTAATATGCA  AGGTTAAGCA  GAAAAAAGCG    300

GAGCCGTAGG  GAAACCGAGT  CTGAATAGGG  CGACTTTAGT  ATATTGGCAT  ATACCCGAAA    360

TCAGGTGATC  TATCCATGAG  CAGGTTGAAG  CTTAGGTAAA  ACTAAGTGGA  GGACCGAACC    420

GTAGTACGCT  AAAAAGTGCC  CGGATGGACT  TGTGGATAGT  GGTGAAATTC  CAATCGAACC    480

TGGAGATAGC  TGGTTCTCTT  CGAAATAGCT  TTAGGGCTAG  CGTATAGTAT  TGTTTAATGG    540

GGGTAGAGCA  CTGAATGTGG  AATGGCGGCA  TCTAGCTGTA  CTGACTATAA  TCAAACTCCG    600

AATACCATTA  AAATTAAGCT ATG CAG TCG GAA CGT GGT ATC ACC ATT GAT           650
                          Met Gln Ser Glu Arg Gly Ile Thr Ile Asp
                           1               5                  10

ATC TCC TTG TGG AAA TTT GAG ACC AGC AAG TAC TAT GTG ACT ATC ATT          698
Ile Ser Leu Trp Lys Phe Glu Thr Ser Lys Tyr Tyr Val Thr Ile Ile
             15                  20                  25
```

| | | | | | | | | | | | | | | | | |
|---|---|---|---|---|---|---|---|---|---|---|---|---|---|---|---|---|
| GAT | GCC | CCA | GGA | CAC | AGA | GAC | TTT | ATC | CAA | AAC | ATG | ATT | ACA | GGG | ACC | 746 |
| Asp | Ala | Pro | Gly 30 | His | Arg | Asp | Phe | Ile 35 | Gln | Asn | Met | Ile | Thr 40 | Gly | Thr | |
| TCT | CAG | GCT | GAC | TGT | GCT | GTC | CTG | ATT | GTT | GCT | GCT | GGT | GTT | GGT | GAA | 794 |
| Ser | Gln | Ala 45 | Asp | Cys | Ala | Val | Leu 50 | Ile | Val | Ala | Ala | Gly 55 | Val | Gly | Glu | |
| TTT | GAA | GCT | GGT | ATC | TCC | AAG | AAT | GGG | CAG | ACC | CGA | CAG | CAT | GCC | CTT | 842 |
| Phe | Glu 60 | Ala | Gly | Ile | Ser | Lys 65 | Asn | Gly | Gln | Thr | Arg 70 | Gln | His | Ala | Leu | |
| CTG | GCT | TAC | ACA | CTG | GGT | GTG | AAA | CAA | CTA | ATT | GTC | GGT | GTT | AAC | AAA | 890 |
| Leu 75 | Ala | Tyr | Thr | Leu | Gly 80 | Val | Lys | Gln | Leu | Ile 85 | Val | Gly | Val | Asn | Lys 90 | |
| ATG | GAT | TCC | ACT | GAG | CCA | CCC | TAC | AGC | CAG | AAG | AGA | TAT | GAG | GAA | ATT | 938 |
| Met | Asp | Ser | Thr | Glu 95 | Pro | Pro | Tyr | Ser | Gln 100 | Lys | Arg | Tyr | Glu | Glu 105 | Ile | |
| GTT | AAG | GAA | GTC | AGC | ACT | TAC | ATT | AAG | AAA | ATT | GGC | TAC | AAC | CCC | GAC | 986 |
| Val | Lys | Glu | Val 110 | Ser | Thr | Tyr | Ile | Lys 115 | Lys | Ile | Gly | Tyr | Asn 120 | Pro | Asp | |
| ACA | GTA | GCA | TTT | GTG | CCA | ATT | TCT | GGT | TGG | AAT | GGT | GAC | AAC | ATG | CTG | 1034 |
| Thr | Val | Ala 125 | Phe | Val | Pro | Ile | Ser 130 | Gly | Trp | Asn | Gly | Asp 135 | Asn | Met | Leu | |
| GAG | CCA | AGT | GCT | AAC | ATG | CCT | TGG | TTC | AAG | GGA | TGG | AAA | GTC | ACC | CGT | 1082 |
| Glu | Pro 140 | Ser | Ala | Asn | Met | Pro 145 | Trp | Phe | Lys | Gly | Trp 150 | Lys | Val | Thr | Arg | |
| AAG | GAT | GGC | AAT | GCC | AGT | GGA | ACC | ACG | CTG | CTT | GAG | GCT | CTG | GAC | TGC | 1130 |
| Lys 155 | Asp | Gly | Asn | Ala | Ser 160 | Gly | Thr | Thr | Leu | Leu 165 | Glu | Ala | Leu | Asp | Cys 170 | |
| ATC | CTA | CCA | CCA | ACT | CGT | CCA | ACT | GAC | AAG | CCC | TTG | GGC | CTG | CCT | CTC | 1178 |
| Ile | Leu | Pro | Pro | Thr 175 | Arg | Pro | Thr | Asp | Lys 180 | Pro | Leu | Gly | Leu | Pro 185 | Leu | |
| CAG | GAT | GTC | TAC | AAA | ATT | GGT | GGT | ATT | GGT | ACT | GTT | CCT | GTT | GGC | CGA | 1226 |
| Gln | Asp | Val | Tyr 190 | Lys | Ile | Gly | Gly | Ile 195 | Gly | Thr | Val | Pro | Val 200 | Gly | Arg | |
| GTG | GAG | ACT | GGT | GTT | CTC | AAA | CCC | GGT | ATG | GTG | GTC | ACC | TTT | CGT | CCA | 1274 |
| Val | Glu | Thr 205 | Gly | Val | Leu | Lys | Pro 210 | Gly | Met | Val | Val | Thr 215 | Phe | Arg | Pro | |
| GTC | AAC | GTT | ACA | ACG | GAA | GTA | AAA | TCT | GTC | GAA | ATG | CAC | CAT | GAA | GCT | 1322 |
| Val | Asn | Val | Thr 220 | Thr | Glu | Val | Lys 225 | Ser | Val | Glu | Met | His 230 | His | Glu | Ala | |
| TTG | GGT | GAA | GCT | CTT | CCT | GGG | GAC | AAT | GTG | GGC | TTC | AAT | GTC | AAG | AAT | 1370 |
| Leu 235 | Gly | Glu | Ala | Leu | Pro 240 | Gly | Asp | Asn | Val | Gly 245 | Phe | Asn | Val | Lys | Asn 250 | |
| GTG | TCT | GTC | AAG | GAT | GTT | CGT | CGT | GGC | AAC | GTT | GCT | GGT | GAC | AGC | AAA | 1418 |
| Val | Ser | Val | Lys | Asp 255 | Val | Arg | Arg | Gly | Asn 260 | Val | Ala | Gly | Asp | Ser 265 | Lys | |
| AAT | GAC | CCA | CCA | ATG | GAA | GCA | GCT | GGC | TTC | CCT | GCT | CAG | GTG | ATT | ATC | 1466 |
| Asn | Asp | Pro | Pro 270 | Met | Glu | Ala | Ala | Gly 275 | Phe | Pro | Ala | Gln | Val 280 | Ile | Ile | |
| CTG | AAC | CAT | CCA | GGC | CAA | ATA | AGC | GCC | GGC | TAT | GCC | CCT | GTA | TTG | GAT | 1514 |
| Leu | Asn | His 285 | Pro | Gly | Gln | Ile | Ser 290 | Ala | Gly | Tyr | Ala | Pro 295 | Val | Leu | Asp | |
| TGC | CAC | ACG | GCT | CAC | ATT | GCA | TGC | AAG | TTT | GCT | GAG | CTG | AAG | GAA | AAG | 1562 |
| Cys | His | Thr 300 | Ala | His | Ile | Ala | Cys 305 | Lys | Phe | Ala | Glu | Leu 310 | Lys | Glu | Lys | |
| ATT | GAT | CGC | CGT | TCT | GGT | AAA | AAG | CTG | GAA | GAT | GGC | CCT | AAA | TTC | TTG | 1610 |
| Ile | Asp | Arg | Arg | Ser 320 | Gly | Lys | Lys | Leu | Glu 325 | Asp | Gly | Pro | Lys | Phe 330 | Leu | |
| | | | | | | | | | | | | | | | | |
| AAG | TCT | GGT | GAT | GCT | GCC | ATT | GTT | GAT | ATG | GTT | CCT | GGC | AAG | CCC | ATG | 1658 |
| Lys | Ser | Gly | Asp | Ala 335 | Ala | Ile | Val | Asp | Met 340 | Val | Pro | Gly | Lys | Pro 345 | Met | |

| | | | | | | | | | | | | | | | | |
|---|---|---|---|---|---|---|---|---|---|---|---|---|---|---|---|---|
| TGT | GTT | GAG | AGC | TTC | TCA | GAC | TAT | CCA | CCT | TTG | GGC | TGC | TTT | GCT | GTC | 1706 |
| Cys | Val | Glu | Ser<br>350 | Phe | Ser | Asp | Tyr<br>355 | Pro | Pro | Leu | Gly | Cys<br>360 | Phe | Ala | Val | |
| GTT | GAT | ATG | AGA | CAG | ACA | GTT | GCG | GTG | GGT | GTC | ATC | AAA | GCA | GTG | GAC | 1754 |
| Val | Asp | Met<br>365 | Arg | Gln | Thr | Val | Ala<br>370 | Val | Gly | Val | Ile | Lys<br>375 | Ala | Val | Asp | |
| AAG | AAG | GCT | GCT | GGA | GCT | GGC | AAG | GTC | ACC | AAG | TCT | GCC | CAG | AAA | GCT | 1802 |
| Lys | Lys<br>380 | Ala | Ala | Gly | Ala | Gly<br>385 | Lys | Val | Thr | Lys | Ser<br>390 | Ala | Gln | Lys | Ala | |

| | | | | | | |
|---|---|---|---|---|---|---|
| CAG | AAG | GCT | AAA | TGA ATATTATCCC TAATACCTCC CACCCCACTC TTAATCAGTG | | 1857 |
| Gln<br>395 | Lys | Ala | Lys | * | | |

GTGGAAGACC GGTCTCAGAA CTGTTTGTTT CAATTGGCCA TTTAAGTTTA GTAGTAAAAG 1917
ACTGGTTAAT GATAACAATG CATCGTAAAA CCTTTCAGAA GGAAAGGAGA ATGTTTTGTG 1977
GACCACGTTG GTTTTCTTTT TTGCGTGTGG CAGTTTTAAG TTATTAGTTT TTAAAATCAG 2037
TACTTTTTAA TGGAAACAAC TTGACCCCCA AATTTGTCAC AGAATTTTGG GACCCATTAA 2097
AAAGGTTAAC TGGGAAAAAA AAAAAAAAA A 2128

( 2 ) INFORMATION FOR SEQ ID NO:17:

( i ) SEQUENCE CHARACTERISTICS:
        ( A ) LENGTH: 398 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| | | | | | | | | | | | | | | |
|---|---|---|---|---|---|---|---|---|---|---|---|---|---|---|
| Met<br>1 | Gln | Ser | Glu | Arg<br>5 | Gly | Ile | Thr | Ile | Asp<br>10 | Ile | Ser | Leu | Trp | Lys<br>15 | Phe |
| Glu | Thr | Ser | Lys<br>20 | Tyr | Tyr | Val | Thr | Ile<br>25 | Ile | Asp | Ala | Pro | Gly<br>30 | His | Arg |
| Asp | Phe | Ile<br>35 | Gln | Asn | Met | Ile | Thr<br>40 | Gly | Thr | Ser | Gln | Ala<br>45 | Asp | Cys | Ala |
| Val | Leu<br>50 | Ile | Val | Ala | Ala | Gly<br>55 | Val | Gly | Glu | Phe | Glu<br>60 | Ala | Gly | Ile | Ser |
| Lys<br>65 | Asn | Gly | Gln | Thr | Arg<br>70 | Gln | His | Ala | Leu | Leu<br>75 | Ala | Tyr | Thr | Leu | Gly<br>80 |
| Val | Lys | Gln | Leu | Ile<br>85 | Val | Gly | Val | Asn | Lys<br>90 | Met | Asp | Ser | Thr | Glu<br>95 | Pro |
| Pro | Tyr | Ser | Gln<br>100 | Lys | Arg | Tyr | Glu | Glu<br>105 | Ile | Val | Lys | Glu | Val<br>110 | Ser | Thr |
| Tyr | Ile | Lys<br>115 | Lys | Ile | Gly | Tyr | Asn<br>120 | Pro | Asp | Thr | Val | Ala<br>125 | Phe | Val | Pro |
| Ile | Ser<br>130 | Gly | Trp | Asn | Gly | Asp<br>135 | Asn | Met | Leu | Glu | Pro<br>140 | Ser | Ala | Asn | Met |
| Pro<br>145 | Trp | Phe | Lys | Gly | Trp<br>150 | Lys | Val | Thr | Arg | Lys<br>155 | Asp | Gly | Asn | Ala | Ser<br>160 |
| Gly | Thr | Thr | Leu | Leu<br>165 | Glu | Ala | Leu | Asp | Cys<br>170 | Ile | Leu | Pro | Pro | Thr<br>175 | Arg |
| Pro | Thr | Asp | Lys<br>180 | Pro | Leu | Gly | Leu | Pro<br>185 | Leu | Gln | Asp | Val | Tyr<br>190 | Lys | Ile |
| Gly | Gly | Ile<br>195 | Gly | Thr | Val | Pro | Val<br>200 | Gly | Arg | Val | Glu | Thr<br>205 | Gly | Val | Leu |
| Lys | Pro<br>210 | Gly | Met | Val | Val | Thr<br>215 | Phe | Arg | Pro | Val | Asn<br>220 | Val | Thr | Thr | Glu |

| Val | Lys | Ser | Val | Glu | Met | His | His | Glu | Ala | Leu | Gly | Glu | Ala | Leu | Pro |
| 225 | | | | | 230 | | | | 235 | | | | | | 240 |

| Gly | Asp | Asn | Val | Gly | Phe | Asn | Val | Lys | Asn | Val | Ser | Val | Lys | Asp | Val |
| | | | | 245 | | | | 250 | | | | | | 255 | |

| Arg | Arg | Gly | Asn | Val | Ala | Gly | Asp | Ser | Lys | Asn | Asp | Pro | Pro | Met | Glu |
| | | | 260 | | | | | 265 | | | | | 270 | | |

| Ala | Ala | Gly | Phe | Pro | Ala | Gln | Val | Ile | Ile | Leu | Asn | His | Pro | Gly | Gln |
| | | 275 | | | | | 280 | | | | | 285 | | | |

| Ile | Ser | Ala | Gly | Tyr | Ala | Pro | Val | Leu | Asp | Cys | His | Thr | Ala | His | Ile |
| | 290 | | | | | 295 | | | | | 300 | | | | |

| Ala | Cys | Lys | Phe | Ala | Glu | Leu | Lys | Glu | Lys | Ile | Asp | Arg | Arg | Ser | Gly |
| 305 | | | | | 310 | | | | 315 | | | | | | 320 |

| Lys | Lys | Leu | Glu | Asp | Gly | Pro | Lys | Phe | Leu | Lys | Ser | Gly | Asp | Ala | Ala |
| | | | | 325 | | | | | 330 | | | | | 335 | |

| Ile | Val | Asp | Met | Val | Pro | Gly | Lys | Pro | Met | Cys | Val | Glu | Ser | Phe | Ser |
| | | | 340 | | | | | 345 | | | | | 350 | | |

| Asp | Tyr | Pro | Pro | Leu | Gly | Cys | Phe | Ala | Val | Val | Asp | Met | Arg | Gln | Thr |
| | | 355 | | | | | 360 | | | | | 365 | | | |

| Val | Ala | Val | Gly | Val | Ile | Lys | Ala | Val | Asp | Lys | Lys | Ala | Ala | Gly | Ala |
| | 370 | | | | | 375 | | | | | 380 | | | | |

| Gly | Lys | Val | Thr | Lys | Ser | Ala | Gln | Lys | Ala | Gln | Lys | Ala | Lys | | |
| 385 | | | | | 390 | | | | | 395 | | | | | |

(2) INFORMATION FOR SEQ ID NO:18:

(i) SEQUENCE CHARACTERISTICS:
        (A) LENGTH: 462 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:18:

| Met | Gly | Lys | Glu | Lys | Thr | His | Ile | Asn | Ile | Val | Val | Ile | Gly | His | Val |
| 1 | | | | 5 | | | | | 10 | | | | | | 15 |

| Asp | Ser | Gly | Lys | Ser | Thr | Thr | Thr | Gly | His | Leu | Ile | Val | Lys | Cys | Gly |
| | | | 20 | | | | | 25 | | | | | 30 | | |

| Gly | Ile | Asp | Lys | Arg | Thr | Ile | Glu | Lys | Phe | Glu | Lys | Glu | Ala | Ala | Glu |
| | | 35 | | | | | 40 | | | | | 45 | | | |

| Met | Gly | Lys | Gly | Ser | Phe | Lys | Tyr | Ala | Trp | Val | Leu | Asp | Lys | Leu | Lys |
| | 50 | | | | | 55 | | | | | 60 | | | | |

| Ala | Glu | Arg | Glu | Arg | Gly | Ile | Thr | Ile | Asp | Ile | Ser | Leu | Trp | Lys | Phe |
| 65 | | | | | 70 | | | | 75 | | | | | | 80 |

| Glu | Thr | Ser | Lys | Tyr | Tyr | Val | Thr | Ile | Ile | Asp | Ala | Pro | Gly | His | Arg |
| | | | | 85 | | | | | 90 | | | | | 95 | |

| Asp | Phe | Ile | Lys | Asn | Met | Ile | Thr | Gly | Thr | Ser | Gln | Ala | Asp | Cys | Ala |
| | | | 100 | | | | | 105 | | | | | 110 | | |

| Val | Leu | Ile | Val | Ala | Ala | Gly | Val | Gly | Glu | Phe | Glu | Ala | Gly | Ile | Ser |
| | | | 115 | | | | | 120 | | | | | 125 | | |

| Lys | Asn | Gly | Gln | Thr | Arg | Glu | His | Ala | Leu | Leu | Ala | Tyr | Thr | Leu | Gly |
| | | | 130 | | | | 135 | | | | | 140 | | | |

| Val | Lys | Gln | Leu | Ile | Val | Gly | Val | Asn | Lys | Met | Asp | Ser | Thr | Glu | Pro |
| 145 | | | | | 150 | | | | | 155 | | | | | 160 |

```
Pro  Tyr  Ser  Gln  Lys  Arg  Tyr  Glu  Glu  Ile  Val  Lys  Glu  Val  Ser  Thr
              165                 170                 175

Tyr  Ile  Lys  Lys  Ile  Gly  Tyr  Asn  Pro  Asp  Thr  Val  Ala  Phe  Val  Pro
              180                 185                 190

Ile  Ser  Gly  Trp  Asn  Gly  Asp  Asn  Met  Leu  Glu  Pro  Ser  Ala  Asn  Met
         195                      200                 205

Pro  Trp  Phe  Lys  Gly  Trp  Lys  Val  Thr  Arg  Lys  Asp  Gly  Asn  Ala  Ser
         210                      215                 220

Gly  Thr  Thr  Leu  Leu  Glu  Ala  Leu  Asp  Cys  Ile  Leu  Pro  Pro  Thr  Arg
225                           230                 235                           240

Pro  Thr  Asp  Lys  Pro  Leu  Arg  Leu  Pro  Leu  Gln  Asp  Val  Tyr  Lys  Ile
              245                      250                 255

Gly  Gly  Ile  Gly  Thr  Val  Pro  Val  Gly  Arg  Val  Glu  Thr  Gly  Val  Leu
              260                      265                 270

Lys  Pro  Gly  Met  Val  Val  Thr  Phe  Ala  Pro  Val  Asn  Val  Thr  Thr  Glu
              275                      280                 285

Val  Lys  Ser  Val  Glu  Met  His  His  Glu  Ala  Leu  Ser  Glu  Ala  Leu  Pro
     290                      295                      300

Gly  Asp  Asn  Val  Gly  Phe  Asn  Val  Lys  Asn  Val  Ser  Val  Lys  Asp  Val
305                           310                 315                           320

Arg  Arg  Gly  Asn  Val  Ala  Gly  Asp  Ser  Lys  Asn  Asp  Pro  Pro  Met  Glu
              325                      330                 335

Ala  Ala  Gly  Phe  Thr  Ala  Gln  Val  Ile  Ile  Leu  Asn  His  Pro  Gly  Gln
              340                      345                 350

Ile  Ser  Ala  Gly  Tyr  Ala  Pro  Val  Leu  Asp  Cys  His  Thr  Ala  His  Ile
         355                      360                 365

Ala  Cys  Lys  Phe  Ala  Glu  Leu  Lys  Glu  Lys  Ile  Asp  Arg  Arg  Ser  Gly
     370                      375                 380

Lys  Lys  Leu  Glu  Asp  Gly  Pro  Lys  Phe  Leu  Lys  Ser  Gly  Asp  Ala  Ala
385                      390                      395                           400

Ile  Val  Asp  Met  Val  Pro  Gly  Lys  Pro  Met  Cys  Val  Glu  Ser  Phe  Ser
                   405                      410                      415

Asp  Tyr  Pro  Pro  Leu  Gly  Arg  Phe  Ala  Val  Arg  Asp  Met  Arg  Gln  Thr
              420                      425                 430

Val  Ala  Val  Gly  Val  Ile  Lys  Ala  Val  Asp  Lys  Lys  Ala  Ala  Gly  Ala
              435                      440                 445

Gly  Lys  Val  Thr  Lys  Ser  Ala  Gln  Lys  Ala  Gln  Lys  Ala  Lys
     450                      455                 460
```

( 2 ) INFORMATION FOR SEQ ID NO:19:

( i ) SEQUENCE CHARACTERISTICS:
        ( A ) LENGTH: 397 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( i v ) ANTI-SENSE: NO ( x i ) SEQUENCE DESCRIPTION: SEQ ID NO:19:

```
Met  Gln  Ser  Glu  Arg  Gly  Ile  Thr  Ile  Asp  Ile  Ser  Leu  Trp  Lys  Phe
 1                  5                      10                      15

Glu  Thr  Ser  Lys  Tyr  Tyr  Val  Thr  Ile  Ile  Asp  Ala  Pro  Gly  His  Arg
              20                      25                      30
```

```
Asp Phe Ile Gln Asn Met Ile Thr Gly Thr Ser Gln Ala Asp Cys Ala
         35                  40                  45

Val Leu Ile Val Ala Ala Gly Val Gly Glu Phe Glu Ala Gly Ile Ser
         50                  55                  60

Lys Asn Gly Gln Thr Arg Glu His Ala Leu Leu Ala Tyr Thr Leu Gly
 65                  70                  75                  80

Val Lys Gln Leu Ile Val Gly Val Asn Lys Met Asp Ser Thr Glu Pro
                 85                  90                  95

Pro Tyr Ser Gln Lys Arg Tyr Glu Glu Ile Val Lys Glu Val Ser Thr
                100                 105                 110

Tyr Ile Lys Lys Ile Gly Tyr Asn Pro Asp Thr Val Ala Phe Val Pro
         115                 120                 125

Ile Ser Gly Trp Asn Gly Asp Asn Met Leu Glu Pro Ser Ala Asn Met
         130                 135                 140

Pro Trp Phe Lys Gly Trp Lys Val Thr Arg Lys Asp Gly Asn Ala Ser
145                 150                 155                 160

Gly Thr Thr Leu Glu Ala Leu Asp Cys Ile Leu Pro Pro Thr Arg Pro
                165                 170                 175

Thr Asp Lys Pro Leu Gly Leu Pro Leu Gln Asp Val Tyr Lys Ile Gly
         180                 185                 190

Gly Ile Gly Thr Val Pro Val Gly Arg Val Glu Thr Gly Val Leu Lys
         195                 200                 205

Pro Gly Met Val Val Thr Phe Gly Pro Val Asn Val Thr Thr Glu Val
    210                 215                 220

Lys Ser Val Glu Met His His Glu Ala Leu Gly Glu Ala Leu Pro Gly
225                 230                 235                 240

Asp Asn Val Gly Phe Asn Val Lys Asn Val Ser Val Lys Asp Val Arg
                245                 250                 255

Arg Gly Asn Val Ala Gly Asp Ser Lys Asn Asp Pro Pro Met Glu Ala
            260                 265                 270

Ala Gly Phe Pro Ala Gln Val Ile Ile Leu Asn His Pro Gly Gln Ile
        275                 280                 285

Ser Ala Gly Tyr Ala Pro Val Leu Asp Cys His Thr Ala His Ile Ala
    290                 295                 300

Cys Lys Phe Ala Glu Leu Lys Glu Lys Ile Asp Arg Arg Ser Gly Lys
305                 310                 315                 320

Lys Leu Glu Asp Gly Pro Lys Phe Leu Asp Ser Gly Asp Ala Ala Ile
                325                 330                 335

Val Asp Met Val Pro Gly Lys Pro Met Cys Val Glu Ser Phe Ser Asp
            340                 345                 350

Tyr Pro Pro Leu Gly Cys Phe Ala Val Arg Asp Met Arg Gln Thr Val
        355                 360                 365

Ala Val Gly Val Ile Lys Ala Val Asp Lys Lys Ala Ala Gly Ala Gly
    370                 375                 380

Lys Val Thr Lys Ser Ala Gln Lys Ala Gln Lys Ala Lys
385                 390                 395
```

( 2 ) INFORMATION FOR SEQ ID NO:20:

( i ) SEQUENCE CHARACTERISTICS:
        ( A ) LENGTH: 1819 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:20:

| | | | | | | |
|---|---|---|---|---|---|---|
| CGGACCGAGC | TCCGTTGCAT | TTTGATGAAT | CCATAGTCAA | ATTAGCGAGA | CACGTTGCGA | 60 |
| ATTGAAACAT | CTTAGTAGCA | ACAGGAAAAG | AAAATAAATA | ATGATTTCGT | CAGTAGTGGC | 120 |
| GAGCGAAAGC | GAAAGAGCCC | AAACCTGTAA | AGGGGGGTTG | GTAGGACATC | TTACATTGAG | 180 |
| TTACAAAATT | TTATGATAGT | AGAAGAAGTT | GGGAAAGCTT | CAACATAGAA | GGTGATATTC | 240 |
| CTGTATACGA | AATCATAAAA | TCTCATAGAT | GTATCCTGAG | TAGGGCGGGG | TACGTGAAAC | 300 |
| CCTGTCTGAA | TCTGCCCGGG | ACCACCCGTA | AGGCTAAATA | CTAATCAGAC | ACCGATAGTG | 360 |
| AACTAGTACC | GTGAGGGAAA | GGTGAAAAGA | ACCCGAGAGG | GGAGTGAAAT | AGATTCTGAA | 420 |
| ACCATTTACT | TACAAGTAGT | CAGAGCACGT | TAAAGTGTGA | TGGCGTACAT | CTTGCAGTAT | 480 |
| GGGCCGGCGA | GTTATGTTAA | TATGCAAGGT | TAAGCACGAA | AAAAGCGGAG | CCGTAGGGAA | 540 |
| ACCGAGTCTG | AATAGGGCGA | CTTTAGTATA | TTGGCATATA | CCCGAAACCA | GGTGATCATC | 600 |
| CATGAGCAGG | TTGAAGCTTA | GGTAAAACTA | AGTGGAGGAC | CGAACCGTAG | TACGCTAAAA | 660 |
| AGTGCCCGGA | TGACTTGTGG | ATAGTGGTGA | AATTCCAATC | GAACCTGGAG | ATAGCTGGTT | 720 |
| CTCTTCGAAA | TAGCTTTAGG | GCTAGCGTAT | AGTACTGTTT | AATGGGGGTA | GAGCACTGAA | 780 |
| TGTGGAATGG | CGGCATCTAG | CTGTACTGAC | TATAATCAAA | CTCCGAATAC | CATTAAAATT | 840 |
| AAGCTATGCA | GTCGGAACGT | GGGTGATAAC | GTCCACGCTC | GCGAGGGAAA | CAACCCAGAT | 900 |
| CCGTCAGCTA | AGGTCCCAAA | AATGTGTTAA | GTGAGAAAGG | TTGTGGAGAT | TCATAAACA | 960 |
| ACTAGGAAGT | TGGTTTAGAA | GCAGCCACCT | TTTAAAGAGT | GCGTAATTGC | TCACTAGTCA | 1020 |
| AGAGATCTTG | CGCCAATAAT | GTAACGGGAC | TCAAACACAA | TACCCAAGCT | ACGGGCACAT | 1080 |
| TATGTGCGTT | AGGAGAGCGT | TTTAATTTCG | TTGAAGTCAG | ACCGTGAGAC | TGGTGGAGAG | 1140 |
| ATTAAAAGTT | CGAGAATGCC | GGCATGAGTA | ACGATTCGAA | GTGAGAATCT | TCGACGCCTA | 1200 |
| TTGGGAAAGG | TTTCCTGGGC | AAGGTTCTCC | ACCCAGGGTT | AGTCAGGGCC | TAAGATGAGG | 1260 |
| CAGAAATGCA | TAGTCGATGG | ACAACAGGTT | AATATTCCTG | TACTTGGTAA | AAGAATGATG | 1320 |
| GAGTGACGAA | AAAGGATAGT | TCTACCACTT | CCACTATGTC | CTATCAATAG | GAGCTGTATT | 1380 |
| TGGCATCATA | GGAGGCTTCA | TTCACTGATT | TCCCCTATTC | TCAGGCTACA | CCCTAGACCA | 1440 |
| AACCTACGCC | AAAATCCATT | TCACTATCAT | ATTCATCGGC | GTAAATCTAA | CTTTCTTCCC | 1500 |
| ACAACACTTT | CTCGGCCTAT | CCGGAATGAC | CCGACCCGAC | GTTACTCGGA | CTACCCCGAT | 1560 |
| GCATACACCA | CATGAAACAT | CCTATCATCT | GTAGGCTCAT | TCATTTCTCT | AACAGCAGTA | 1620 |
| ATATTAATAA | TTTTCATGAT | TTGAGAAGCC | TTCGCCTTCG | AAGCGAAAAG | TCCTAATAGT | 1680 |
| AGAAGAACCC | TCCATAAACC | TGGAGTGACT | ATATGGATGC | CCCCACCCTA | CCTCACATTC | 1740 |
| GAAGAACCCG | TATACATAAA | ATCTAGACAA | AAAAGGAAGG | AAGTGAACGC | CCCACAAAAA | 1800 |
| AAAAAAAAAA | AAAAAAAA | | | | | 1819 |

( 2 ) INFORMATION FOR SEQ ID NO:21:

( i ) SEQUENCE CHARACTERISTICS:
( A ) LENGTH: 1869 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:21:

| | | | | | |
|---|---|---|---|---|---|
| AACTAAGTGG | AGGACCGAAC | CGTAGTACGC | TAAAAAGTGC | CCGGATGACT | TGTGGATAGT | 60 |
| GGTGAAATTC | CAATCGAACC | TGGAGATAGC | TGGTTCTCTT | CGAAATAGCT | TTAGGGCTAG | 120 |
| CGTATAGTAT | TGTTTAATGG | GGGTAGAGCA | CTGAATGTGG | AATCGGCGGC | ATCTAGCTGT | 180 |
| ACTGACTATA | ATCAAACTCC | GAATACCATT | AAAATTAAGC | TATGCAGTCG | GAACGTGGGT | 240 |
| GATAACCTCC | ACTCTCGCGA | GGGAAACAAC | CCAGATCGTC | AGCTAAGGTC | CCAAAATTGT | 300 |
| GTTAAGTGAG | AAAGGTTGTG | AGATTTCATA | AACAACTAGG | AAGTTGGCTT | AGAAGCAGCC | 360 |
| ACCTTTTAAA | GAGTGCGTAA | TTGCTCACTA | GTCAAGAGAT | CTTGCGCCAA | TAATGTAACG | 420 |
| GGACTCAAAC | ACAATACCGA | AGCTACGGGC | ACATTATGTC | GGTTAGGAGA | GCGTTTTAAT | 480 |
| TTCGTTGAAG | TCAGACCGTG | AGACTGGTGG | AGAGATTAAA | AGTTCGAGAA | TGCCCGGCAT | 540 |
| GAGTAACGAT | TCGAAGTGAG | AATCTTCGAC | GCCTATTGGG | AAAGGTTTCC | TGGGCAAGGT | 600 |
| TCGTCCACCC | AGGGTTAGTC | AGGGCCTAAG | ATGAGGCAGA | AATGCATAGT | CGATGGACAA | 660 |
| CAGGTTAATA | TTCCTGTACT | TGGTAAAAGA | ATGATGGAGT | GACGAAAAAG | GATAGTTCTA | 720 |
| CCACTTACTG | GATTGTGGGG | TAAGCAACAA | GAGAGTTATA | TAGGCAAATC | CGTATAGCAT | 780 |
| AATCTTGAGT | TGTGATGCAT | AGTGAAGACT | TCGGTCGAGT | AACGAATTGA | ATCGATTTCA | 840 |
| TGTTTCCAAG | AAAAGCTTCT | AGTGTTAATT | TTTTATCAAC | CTGTACCGAG | AACGAACACA | 900 |
| CGTTCCCAAG | ATGAGTATTC | TAAGGCGAGC | GAGAAAACCA | ATGTTAAGGA | ACTCTGCAAA | 960 |
| ATAACCCCGT | AAGTTCGCGA | GAAGGGGCGC | CTATTTTAA | TAGGCCACAG | AAAATAGGGG | 1020 |
| GGCAACTGTT | TATCAAAAAC | ACAGCTCTCT | GCTAAGTTGT | AAAACGACGT | ATAGAGGGTG | 1080 |
| AAGCCTGCCC | AGTCCCGAAG | TTAAACGGAG | ATGTTAGCTT | ACGCAAAGCA | TTAAAGTGAA | 1140 |
| GCCCGGGTGA | ACGGCGGCCG | TAACTATAAC | GGTCCTAAGG | TAGCGAAATT | CCTTGTCAAC | 1200 |
| TAATTATTGA | CCTGCACGAA | AGGCGCAATG | ATCTCCCTAC | TGTCTCAACA | TTGGACTCGG | 1260 |
| TGAAATTATG | GTACCAGTGA | AAACGCAGGT | TACCCGCATC | AAGACGAAAA | GACCCCGTGG | 1320 |
| AGCTTTACTA | TAACTTCGTA | TTGAAAATTG | GTTAGCATG | TGTAGGATAG | GCGGGAGACT | 1380 |
| TTGAAGCTGG | GACGCTAGTT | CTAGTGGAGT | CAACCTTGAA | ATACCACCCT | TGCTAAATTG | 1440 |
| ATTTTCTAAC | CCGTTCCCCT | TATCTGGAAG | GAGACAGTGC | GTGGTGGGTA | GTTTGACTGG | 1500 |
| GCGGTCGCCT | CCTAAAGTGT | AACGGAGGCG | TTCAAAGCTA | CACTCAATAT | GGTCAGAAAC | 1560 |
| CATATGCAGA | GCACAAAGGT | AAAAGTGTGG | TTGACTGCAA | GACTTACAAG | TCGAGCAGGT | 1620 |
| GCGAAAGCAG | GACTTAGTGA | TCCGGCGGTA | CATTGTGGAA | TGGCCGTCGC | TCAACGGATA | 1680 |
| AAAGTCACCC | CGGGGATAAC | AGGCTAATCT | TCCCCAAGAG | ATCACATCGA | CGGGAAGGTT | 1740 |
| TGGCACCTCG | ATGTCGGCTC | ATCGCATCCT | GGAGCTGGAG | TCGGTTCCAA | GGGTTTGCTG | 1800 |
| TTCGCCAATT | AAAGCGGTAC | GTGAGCTGGG | TTCAGAACGT | CGTGAGACAG | TTCGGTCCTC | 1860 |
| CACTTAGTT | | | | | | 1869 |

( 2 ) INFORMATION FOR SEQ ID NO:22:

( i ) SEQUENCE CHARACTERISTICS:
        ( A ) LENGTH: 3850 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:22:

| | | | | | | |
|---|---|---|---|---|---|---|
| CGGCACGAGC | GGCACGAGAG | AAGAGACTCC | AATCGACAAG | AAGCTGGAAA | AGAATGATGT | 60 |
| TGTCCTTAAA | CAACCTACAG | AATATCATCT | ATAACCGGT | AATCCCGTTT | GTTGGCACCA | 120 |
| TTCCTGATCA | GCTGGATCCT | GGAACTTTGA | TTGTGATACG | TGGGCATGTT | CCTAGTGACG | 180 |
| CAGACAGATT | CCAGGTGGAT | CTGCAGAATG | GCAGCAGCGT | GAAACCTCGA | GCCGATGTGG | 240 |
| CCTTTCATTT | CAATCCTCGT | TTCAAAAGGG | CCGGCTGCAT | TGTTTGCAAT | ACTTTGATAA | 300 |
| ATGAAAAATG | GGGACGGGAA | GAGATCACCT | ATGACACGCC | TTTCAAAAGA | GAAAAGTCTT | 360 |
| TTGAGATCGT | GATTATGGTG | CTGAAGGACA | AATTCCAGGT | GGCTGTAAAT | GGAAAACATA | 420 |
| CTCTGCTCTA | TGGCCACAGG | ATCGGCCCAG | AGAAAATAGA | CACTCTGGGC | ATTTATGGCA | 480 |
| AAGTGAATAT | TCACTCAATT | GGTTTTAGCT | TCAGCTCGGA | CTTACAAAGT | ACCCAAGCAT | 540 |
| CTAGTCTGGA | ACTGACAGAG | ATAGTTAGAG | AAAATGTTCC | AAAGTCTGGC | ACGCCCAGC | 600 |
| TTAGCCTGCC | ATTCGCTGCA | AGGTTGAACA | CCCCCATGGG | CCCTGGACGA | ACTGTCGTCG | 660 |
| TTCAAGGAGA | AGTGAATGCA | AATGCCAAAA | GCTTTAATGT | TGACCTACTA | GCAGGAAAAT | 720 |
| CAAAGGATAT | TGCTCTACAC | TTGAACCCAC | GCCTGAATAT | TAAAGCATTT | GTAAGAAATT | 780 |
| CTTTTCTTCA | GGAGTCCTGG | GGAGAAGAAG | AGAGAAATAT | TACCTCTTTC | CCATTTAGTC | 840 |
| CTGGGATGTA | CTTTGAGATG | ATAATTTATT | GTGATGTTAG | AGAATTCAAG | GTTGCAGTAA | 900 |
| ATGGCGTACA | CAGCCTGGAG | TACAAACACA | GATTTAAAGA | GCTCAGCAGT | ATTGACACGC | 960 |
| TGGAAATTAA | TGGAGACATC | CACTTACTGG | AAGTAAGGAG | CTGGTAGCCT | ACCTACACAG | 1020 |
| CTGCTACAAA | AACCAAAATA | CAGAATGGCT | TCTGTGATAC | TGGCCTTGCT | GAAACGCATC | 1080 |
| TCACTGGTCA | TTCTATTGTT | TATATTGTTA | AAATGAGCTT | GTGCACCATT | AGGTCCTGCT | 1140 |
| GGGTGTTCTC | AGTCCTTGCC | ATGACGTATG | GTGGTGTCTA | GCACTGAATG | GGGAAACTGG | 1200 |
| GGGCAGCAAC | ACTTATAGCC | AGTTAAAGCC | ACTCTGCCCT | CTCTCCTACT | TGGCTGACT | 1260 |
| CTTCAAGAAT | GCCATTCAAC | AAGTATTTAT | GGAGTACCTA | CTATAATACA | GTAGCTAACA | 1320 |
| TGTATTGAGC | ACAGATTTTT | TTTGGTAAAT | CTGTGAGGAG | CTAGGATATA | TACTTGGTGA | 1380 |
| AACAAACCAG | TATGTTCCCT | GTTCTCTTGA | GCTTCGACTC | TTCTGTGCGC | TACTGCTGCG | 1440 |
| CACTGCTTTT | TCTACAGGCA | TTACATCAAC | TCCTAAGGGG | TCCTCTGGGA | TTAGTTATGC | 1500 |
| AGATATTAAA | TCACCCGAAG | ACACTAACTT | ACAGAAGACA | CAACTCCTTC | CCCAGTGATC | 1560 |
| ACTGTCATAA | CCAGTGCTCT | GCCGTATCCC | ATCACTGAGG | ACTGATGTTG | ACTGACATCA | 1620 |
| TTTTCTTTAT | CGTAATAAAC | ATGTGGCTCT | ATTAGCTGCA | AGCTTTACCA | AGTAATTGGC | 1680 |
| ATGACATCTG | AGCACAGAAA | TTAAGCCAAA | AAACCAAAGC | AAAACAAATA | CATGGTGCTG | 1740 |
| AAATTAACTT | GATGCCAAGC | CCAAGGCAGC | TGATTTCTGT | GTATTGAAC | TTACCCGAAA | 1800 |
| TCAGAGTCTA | CACAGACGCC | TACAGAAGTT | CAGGAAGAG | CCAAGATGCA | TTCAATTTGT | 1860 |
| AAGATATTTA | TGGCCAACAA | AGTAAGGTCA | GGATTAGACT | TCAGGCATTC | ATAAGGCAGG | 1920 |
| CACTATCAGA | AAGTGTACGC | CAACTAAGGG | ACCCACAAAG | CAGGCAGAGG | TAATGCAGAA | 1980 |
| ATCTGTTTTG | TTCCCATGAA | ATCACCAATC | AAGGCCTCCG | TTCTTCTAAA | GATTAGTCCA | 2040 |
| TCATCATTAG | CAACTGAGAT | CAAAGCACTC | TTCCACTTTA | CGTGATTAAA | ATCAAACCTG | 2100 |
| TATCAGCAAG | TTAAATGGTT | CCATTTCTGT | GATTTTCTA | TTATTTGAGG | GGAGTTGGCA | 2160 |
| GAAGTTCCAT | GTATATGGGA | TCTTTACAGG | TCAGATCTTG | TTACAGGAAA | TTTCAAGGT | 2220 |

-continued

| | | | | | | |
|---|---|---|---|---|---|---|
| TTGGGAGTGG | GGAGGGAAAA | AAGCTCAGTC | AGTGAGGATC | ATTCCACATT | AGACTGGGGC | 2280 |
| AGAACTCTGC | CAGGATTTAG | GAATATTTTC | AGAACAGATT | TTAGATATTA | TTTCTATCCA | 2340 |
| TATATTGAAA | AGGAATACCA | TTGTCAATCT | TATTTTTTTA | AAAGTACTCA | GTGTAGAAAT | 2400 |
| CGCTAGCCCT | TAATTCTTTT | CCAGCTTTTC | ATATTAATGT | ATGCAGAGTC | TCACCAAGCT | 2460 |
| CAAAGACACT | GGTTGGGGGT | GGAGGGTGCC | ACAGGGAAAG | CTGTAGAAGG | CAAGAAGACT | 2520 |
| CGAGAATCCC | CCAGAGTTAT | CTTTCTCCAT | AAAGACCATC | AGAGTGCTTA | ACTGAGCTGT | 2580 |
| TGGAGACTGT | GAGGCATTTA | GGAAAAAAAT | AGCCCACTCA | CATCATTCCT | TGTAAGTCTT | 2640 |
| AAGTTCATTT | TCATTTTACG | TGGAGGAAAA | AAATTTAAAA | AGCTATTAGT | ATTTATTAAT | 2700 |
| GAATTTTACT | GAGACATTTC | TTAGAAATAT | GCACTTCTAT | ACTAGCAAGC | TCTGTCTCTA | 2760 |
| AAATGCAAGT | TGGCCTTTTG | CTTGCCACAT | TTCTGCATTA | AACTTCTATA | TTAGCTTCAA | 2820 |
| AGGCTTTTAA | TCTCAATGCG | AACATTCTAC | GGGATGTTCT | TAGATGCCTT | TAAAAGGGG | 2880 |
| GCAAGATCTA | ATTTTATTTG | AACCCTCACT | TTCCAACTTT | CACCATGACC | CAGTACTAGA | 2940 |
| GATTAGGGCA | CTTCAAAGCA | TTGAAAAAAA | TCTACTGATA | CTTACTTTCT | TAGACAAGTA | 3000 |
| GTTCTTAGTT | AACCACCAAT | GGAACTGGGT | TCATTCTGAA | TCCTGGAGGA | GCTTCCTCGT | 3060 |
| GCCACCCAGT | GTTTCTGGGC | CCTCTGTGTG | AGCAGCCAGG | TGTGAGCTGT | TTTAGAAGCA | 3120 |
| GCGTGTTGCC | TTCATCTCTC | CCGTTCCCA | AAAGAACAAA | GGATAAAGGT | GACAGTCACA | 3180 |
| CTCCTGGGTT | AAAAAAAGCA | TTCCAGAACC | ACTTCTCTTT | ATGGGCACAA | CAACAAAGAA | 3240 |
| GCTAAGTTCG | CCTACCCAAA | TGAAAGTAGG | CTTTACAGTC | AAGTACTTCT | GTTGATTGCT | 3300 |
| AAATAACTTC | ATTTTCTTGA | AATAGAGCAA | CTTTGAGTGA | AATCTGCAAC | ATGGATACCA | 3360 |
| TGTATGTAAG | ATACTGCTGT | ACAGAAGAGT | TAAGGCTTAC | AGTGCAAATG | AGGCGTCAGC | 3420 |
| TTTGGGTGCT | AAAATTAACA | AGTCTAATAT | TATTACCATC | AATCAGGAAG | AGATAATAAA | 3480 |
| TGTTTAAACA | AACACAGCAG | TCTGTATAAA | AATACGTGTA | TATTTACTCT | TTCTGTGCAC | 3540 |
| GCTCTATAGC | ATAGGCAGGA | GAGGCTTATG | TGGCAGCACA | AGCCAGGTGG | GGATTTTGTA | 3600 |
| AAGAAGTGAT | AAAACATTTG | TAAGTAATCC | AAGTAGGAGA | TATTAAGGCA | CCAAAAGTAA | 3660 |
| CATGGCACCC | AACACCCAAA | AATAAAAATA | TGAAATATGA | GTGTGAACTC | TGAGTAGAGT | 3720 |
| ATGAAACACC | ACAGAAAGTC | TTAGAAATAG | CTCTGGAGTG | GCTCTCCCAG | GACAGTTTCC | 3780 |
| AGTTGGCTGA | ATAGTCTTTT | GGCACTGATG | TTCTACTTCT | TCACATTCAT | CTAAAAAAAA | 3840 |
| AAAAAAAAAA | | | | | | 3850 |